US011246893B2

(12) United States Patent
Madsen, II et al.

(10) Patent No.: US 11,246,893 B2
(45) Date of Patent: Feb. 15, 2022

(54) BACTERIOCIN PRODUCTION, COMPOSITIONS AND METHODS OF USE

(71) Applicant: ISOThrive Inc., Healdsburg, CA (US)

(72) Inventors: Lee Madsen, II, Manassas, VA (US); Jack Oswald, Healdsburg, CA (US); Sarah Stanley, Arlington, VA (US); Yvonne Lorraine Kapila, Greenbrae, CA (US)

(73) Assignee: ISOThrive Inc., Healdsburg, CA (US)

( * ) Notice: Subject to any disclaimer, the term of this patent is extended or adjusted under 35 U.S.C. 154(b) by 35 days.

(21) Appl. No.: 16/347,407

(22) PCT Filed: Nov. 7, 2017

(86) PCT No.: PCT/US2017/060417
§ 371 (c)(1),
(2) Date: May 3, 2019

(87) PCT Pub. No.: WO2018/089368
PCT Pub. Date: May 17, 2018

(65) Prior Publication Data

US 2020/0055905 A1    Feb. 20, 2020

Related U.S. Application Data

(60) Provisional application No. 62/419,123, filed on Nov. 8, 2016, provisional application No. 62/419,145, filed on Nov. 8, 2016.

(51) Int. Cl.
| | |
|---|---|
| *A01N 63/00* | (2020.01) |
| *A61K 35/741* | (2015.01) |
| *A61P 35/00* | (2006.01) |
| *C07K 14/315* | (2006.01) |
| *A61K 38/00* | (2006.01) |

(52) U.S. Cl.
CPC ............ *A61K 35/741* (2013.01); *A61P 35/00* (2018.01); *C07K 14/315* (2013.01); *A61K 38/00* (2013.01)

(58) Field of Classification Search
None
See application file for complete search history.

(56) References Cited

U.S. PATENT DOCUMENTS

| 5,705,160 A | 1/1998 | Bruce et al. | |
|---|---|---|---|
| 2006/0223161 A1* | 10/2006 | Stern .................... | C07K 14/315 435/253.4 |
| 2007/0178054 A1 | 8/2007 | Srinivasa et al. | |
| 2011/0236359 A1* | 9/2011 | Lacroix ............... | A23L 3/34635 424/93.45 |

FOREIGN PATENT DOCUMENTS

| EP | 3405500 | 11/2018 |
|---|---|---|
| WO | 2018023003 | 2/2018 |
| WO | WO-2018089368 A1 | 5/2018 |
| WO | WO-2018089368 A4 | 5/2018 |

OTHER PUBLICATIONS

"International Application Serial No. PCT/US2017/060417, International Search Report dated Mar. 28, 2018", 4 pgs.
"International Application Serial No. PCT/US2017/060417, Invitation to Pay Additional Fees and Partial Search Report dated Jan. 26, 2018", 2 pgs.
"International Application Serial No. PCT/US2017/060417, Written Opinion dated Mar. 28, 2018", 6 pgs.
Dobson, Alleson, et al., "Bacteriocin Production: a Probiotic Trait?", Applied and Environmental Microbiology, 78(1), (Jan. 2012), 6 pgs.
Lin, Jun, "Novel Approaches for Campylobacter Control in Poultry", Foodborne Pathogens and Disease, vol. 6, No. 7, (2009), pp. 755-765.
McFarland, LV, "Can *Saccharomyces boulardii* prevent antibiotic-associated diarrhea in children?", Nature Clinical Practice Gastroenterology & Hepatology vol. 2 No. 6, (Jun. 2005), pp. 262-263.
Pascual, Monica, et al., "Lactobacillus salivarius CTC2197 Prevents *Salmonella enteritidis* Colonization in Chickens", Applied and Environmental Microbiology, vol. 65, No. 11, (1999), pp. 4981-4986.
Saint-Cyr, Manuel Jimmy, et al., "Evaluation of the anti-Campylobacter activity of Lactobacillus salivarius SMXD51, a bacteriocin-producing lactic bacteria, in broiler chickens", 1 pg.
Shin, J. M., et al., "Biomedical applications of nisin", Journal of Applied Microbiology ISSN 1364-5072, (2015), pp. 1449-1465.
Yang, Liying, et al., "Microbiome in Reflux Disorders and Esophageal Adenocarcinoma", Cancer J. 2014 ; 20(3): doi:10.1097/PPO. 0000000000000044, (2015), 10 pgs.
Yang, Liying, et al., "Molecular Pathways: Pathogenesis and Clinical Implications of Microbiome Alteration in Esophagitis and Barrett Esophagus", Clin Cancer Res; 18(8), (Apr. 15, 2012), pp. 2138-2144.
"European Application Serial No. 17868733.1, Extended European Search Report dated Sep. 7, 2020", 11 pgs.
"International Application Serial No. PCT US2017 060417, International Preliminary Report on Patentability dated May 23, 2019", 8 pages.
"European Application Serial No. 17868733.1, Partial supplementary European search report dated Jun. 3, 2020", 12 pages.

* cited by examiner

*Primary Examiner* — Jana A Hines
*Assistant Examiner* — Khatol S Shahnan Shah
(74) *Attorney, Agent, or Firm* — Schwegman Lundberg & Woessner, P.A.

(57) ABSTRACT

Methods are described herein for generating beneficial compounds and/or materials such as bacteriocins that include contacting 'challenger' microbes with the 'protagonist' microorganisms. The challenger microbes do not directly manufacture the beneficial compounds and/or materials and instead stimulate the protagonist microorganisms to produce beneficial compounds and materials. The protagonist and/or challenger microorganisms can be administered to a subject so the beneficial compounds and/or materials can be made in vivo. Compositions and methods of using beneficial compounds and/or materials are also described herein.

11 Claims, 25 Drawing Sheets

Specification includes a Sequence Listing.

|  | %/BRIX: |
|---|---|
| BRIX | 63.01 |
| MANNITOL | 6.23 |
| GLUCOSE | 0.85 |
| FRUCTOSE | 0.16 |
| SUCROSE | 1.86 |
| MALTOSE | 4.29 |
| MIMO | 84.77 |
| LACTATE | 0.00 |
| GLYCEROL | 0.41 |
| FORMATE | 0.00 |
| ACETATE | 0.00 |
| TOTAL, %: | 98.58 |
| PURITY, %: | 86.00 |
| MWD, Da: | 776.47 |

| DP: | %/BRIX: |
|---|---|
| MIMO-DP3 | 14.89 |
| MIMO-DP4 | 22.19 |
| MIMO-DP5 | 23.66 |
| MIMO-DP6 | 15.23 |
| MIMO-DP7 | 5.75 |
| MIMO-DP8 | 2.48 |
| MIMO-DP9 | 0.58 |

|  | α-1,6), %: | α-1,3), %: |
|---|---|---|
| HPLC, %: | 90.34 | 10.12 |
| NMR, %: | 95.65 | 4.35 |

FIG. 13

SEQUENCE LISTING

```
<160> NUMBER OF SEQ ID NOS: 11

<210> SEQ ID NO 1
<211> LENGTH: 57
<212> TYPE: PRT
<213> ORGANISM: Lactococcus lactis

<400> SEQUENCE: 1

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys His Cys Ser Ile His Val Ser Lys
    50                  55

<210> SEQ ID NO 2
<211> LENGTH: 57
<212> TYPE: PRT
<213> ORGANISM: Lactococcus lactis

<400> SEQUENCE: 2

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys Asn Cys Ser Ile His Val Ser Asn
    50                  55

<210> SEQ ID NO 3
<211> LENGTH: 57
<212> TYPE: PRT
<213> ORGANISM: Lactococcus lactis
```

```
<400> SEQUENCE: 3

Met Ser Thr Lys Asp Phe Asn Leu Asp Leu Val Ser Val Ser Lys Thr
1               5                   10                  15

Asp Ser Gly Ala Ser Thr Arg Ile Thr Ser Ile Ser Leu Cys Thr Pro
                20                  25                  30

Gly Cys Lys Thr Gly Val Leu Met Gly Cys Asn Leu Lys Thr Ala Thr
            35                  40                  45

Cys Asn Cys Ser Val His Val Ser Lys
        50                  55

<210> SEQ ID NO 4
<211> LENGTH: 57
<212> TYPE: PRT
<213> ORGANISM: Lactococcus lactis

<400> SEQUENCE: 4

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
                20                  25                  30

Gly Cys Lys Thr Gly Ala Leu Met Gly Cys Asn Met Lys Thr Ala Thr
            35                  40                  45

Cys Asn Cys Ser Val His Val Ser Lys
        50                  55

<210> SEQ ID NO 5
<211> LENGTH: 5
<212> TYPE: PRT
<213> ORGANISM: Artificial Sequence
<220> FEATURE:
<223> OTHER INFORMATION: A consensus sequuence

<400> SEQUENCE: 5

Tyr Gly Asn Gly Val
1               5

<210> SEQ ID NO 6
<211> LENGTH: 34
<212> TYPE: PRT
<213> ORGANISM: Lactococcus lactis

<400> SEQUENCE: 6

Ile Thr Ser Ile Ser Leu Cys Thr Pro Gly Cys Lys Thr Gly Ala Leu
1               5                   10                  15

Met Gly Cys Asn Met Lys Thr Ala Thr Cys Asn Cys Ser Ile His Val
                20                  25                  30

Ser Lys

<210> SEQ ID NO 7
<211> LENGTH: 541
<212> TYPE: PRT
<213> ORGANISM: Lactococcus lactis

<400> SEQUENCE: 7

Met Asn Ser His Leu Asn Gly Val Val Asn Met Lys Glu Asn Trp Trp
1               5                   10                  15

Gln Lys Thr Val Val Tyr Gln Ile Tyr Pro Arg Ser Phe Met Asp Ala
                20                  25                  30

Asn Gly Asp Gly Val Gly Asp Leu Gln Gly Ile Ile Ser Lys Leu Asp
            35                  40                  45
```

```
Tyr Leu Glu Lys Leu Gly Ile Gly Ala Ile Trp Leu Ser Pro Val Tyr
     50                  55                  60

Gln Ser Pro Met Asp Asp Asn Gly Tyr Asp Ile Ser Asp Tyr Gln Ala
 65              70                  75                  80

Ile Ala Asp Val Phe Gly Thr Met Ser Asp Met Asp Glu Leu Leu Leu
                 85                  90                  95

Glu Ala Lys Lys Arg Asn Ile Gln Ile Val Met Asp Leu Val Val Asn
            100                 105                 110

His Thr Ser Asp Glu His Lys Trp Phe Val Glu Ala Arg Lys Ser Lys
            115                 120                 125

Asp Asn Ala Tyr Arg Asp Tyr Tyr Ile Trp Ala Asp Glu Pro Asn Ala
        130                 135                 140

Leu Gln Ser Thr Phe Ser Gly Ser Ala Trp Glu Phe Asp Glu Glu Ser
145                 150                 155                 160

Gly Gln Tyr Phe Leu His Leu Phe Ser Lys Arg Gln Pro Asp Leu Asn
                165                 170                 175

Trp Glu Asn Pro Gln Val His Gln Glu Val Tyr Asp Met Met Asn Phe
            180                 185                 190

Trp Ile Asp Lys Gly Ile Gly Gly Phe Arg Met Asp Val Ile Asp Leu
        195                 200                 205

Ile Gly Lys Glu Ile Asp Gln Glu Ile Thr Gly Asn Gly Pro Lys Leu
    210                 215                 220

His Glu Tyr Leu His Glu Met Asn Gln Ala Thr Phe Gly Gln Lys Asn
225                 230                 235                 240

Leu Leu Thr Val Gly Glu Thr Trp Gly Ala Thr Pro Glu Ile Ala Glu
                245                 250                 255

Leu Tyr Ser Asp Pro Lys Arg Gln Glu Leu Ser Met Val Phe Gln Phe
            260                 265                 270

Glu His Ile Thr Asn Ala Tyr Leu Asp Glu Gly Glu Lys Trp Asp Lys
        275                 280                 285

Lys Glu Phe Ser Val Ser Lys Leu Lys Glu Ile Leu Ala Lys Trp Gln
    290                 295                 300

Ala Leu Glu Lys Gly Trp Asn Ser Leu Phe Trp Asn Asn His Asp Leu
305                 310                 315                 320

Pro Arg Ile Val Ser Asn Trp Gly Asn Asp Gly Lys Tyr Arg Leu Lys
                325                 330                 335

Ser Ala Lys Ala Phe Ala Ile Leu Leu His Leu Met Lys Gly Thr Pro
            340                 345                 350

Tyr Ile Tyr Gln Gly Glu Glu Leu Gly Met Thr Asn Tyr Pro Phe Glu
        355                 360                 365

Ser Ile Glu Glu Val Asn Asp Ile Glu Ser Arg Asn Met Phe Ala Glu
    370                 375                 380

Arg Leu Ala Ala Gly His Ser Glu Asn Glu Ile Met Asp Ser Ile Arg
385                 390                 395                 400

Arg Val Gly Arg Asp Asn Ala Arg Thr Pro Met Gln Trp Thr Ala Gly
                405                 410                 415

Glu Asn Ala Gly Phe Thr Asp Gly Lys Pro Trp Leu Ala Val Asn Pro
            420                 425                 430

Asn His Glu Glu Ile Asn Ala Asp Gln Ala Met Ser Asp Pro Asp Ser
        435                 440                 445

Val Phe Tyr Thr Tyr Gln Lys Leu Ile Glu Leu Arg Lys Gln His Asp
    450                 455                 460
```

Trp Val Ile Tyr Gly Gly Phe Lys Leu Ile Asp Ser Glu Ala Asp Val
465                 470                 475                 480

Phe Ala Tyr Leu Arg Thr Tyr Lys Gly Lys Tyr Leu Val Val Ala
            485                 490                 495

Asn Leu Ser Asp Glu Glu Asn Gln Phe Lys Thr Gly Phe Val Cys Arg
            500                 505                 510

Asp Leu Leu Ile His Asn Glu Asn Phe Leu Pro Glu Leu Ser Gln Ile
                515                 520                 525

Lys Leu Lys Ala Trp Glu Ala Phe Ala Cys Glu Val Glu
530                 535                 540

<210> SEQ ID NO 8
<211> LENGTH: 57
<212> TYPE: PRT
<213> ORGANISM: Lactococcus lactis

<400> SEQUENCE: 8

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys His Cys Ser Ile His Val Ser Lys
    50                  55

<210> SEQ ID NO 9
<211> LENGTH: 566
<212> TYPE: PRT
<213> ORGANISM: Bacillus subtilis

<400> SEQUENCE: 9

Met Arg Leu Thr Ile Ser Arg Lys Phe Ser Leu Val Phe Leu Thr Leu
1               5                   10                  15

Ile Leu Ile Asn Leu Leu Val Gly Gly Ile Gly Ala Phe Asn Met Gln
            20                  25                  30

His Ile Ile Gln Lys Thr Asp Glu Ile Asn Thr Lys Trp Ile Asp Gly
        35                  40                  45

Ile Lys Glu Ile Thr Ser Ile Asn Tyr Leu Thr Glu His Leu Ser Ser
    50                  55                  60

Lys Glu Lys Asp Phe Leu Ile Phe Thr Asp Lys Ser Lys Met Asp Thr
65                  70                  75                  80

Leu Asp Gln Glu Met Asn Gln Ile Leu Glu Asp Ile Asn Gln Lys Leu
                85                  90                  95

Asp Ser Tyr Glu Lys Thr Ile Ser Asn Asp Lys Glu Gln Lys Leu Phe
            100                 105                 110

Glu Glu Leu Gln Asn Glu Val Asn Thr Tyr Ala Asp Ile His Ala Gln
        115                 120                 125

Ile Ile Glu Ser Gly Arg Thr Asn Asp Met Asp Lys Ala Arg Gly Leu
    130                 135                 140

Leu Val Gln Thr Glu Ala Ser Phe Glu Asn Met Lys Lys Ser Val Thr
145                 150                 155                 160

Gln Leu Val Asp Phe Asn Lys Glu Gly Ser Asn Thr Ala Val Lys Glu
                165                 170                 175

Thr Lys Asp Val Tyr His Lys Gly Leu Ile Tyr Thr Ala Ser Leu Val
            180                 185                 190

Ala Ala Ser Ile Ile Ser Ile Phe Ile Trp Leu Tyr Ile Thr Arg
            195                 200                 205

Asn Ile Val Lys Pro Ile Ile Arg Met Lys Glu Ser Ala Asn His Ile
210                 215                 220

Ala Glu Gly Asp Leu Ser Ser Asp Ile Glu Pro Leu Asn Ser Lys Asp
225                 230                 235                 240

Glu Leu Gly Asp Leu Asn Glu Ala Leu Gln Lys Met Val Gly Asn Leu
                245                 250                 255

Arg Asp Ile Val Gly Tyr Ser Lys Glu Ile Ser Ser Arg Val Leu Ser
                260                 265                 270

Ser Ser Gln Val Leu Ala Thr Ala Thr Asn Glu Thr Arg Ser Gly Ser
            275                 280                 285

Lys His Ile Thr Glu Thr Met Asn Glu Met Ala Glu Gly Ser Glu Gln
            290                 295                 300

Gln Ala Gln Asp Ala Val Thr Ile Ala Glu Ser Met Asn Glu Phe Thr
305                 310                 315                 320

Glu Ser Ile Asp Lys Ala Tyr Asn His Gly Ile Thr Ile Ser Asp Thr
                325                 330                 335

Ser Gln Asn Val Leu Glu Leu Ala Val Ser Gly Asn Glu Asn Met Asp
                340                 345                 350

Thr Ser Leu Gln Gln Met Lys Thr Ile His His Ile Val Gln Glu Ala
            355                 360                 365

Val His Lys Val Arg Ser Leu Glu Gln His Ser Gln Asp Ile Asn Lys
            370                 375                 380

Leu Val Gln Val Ile Asn Gly Ile Ala Glu Gln Thr Asn Leu Leu Ser
385                 390                 395                 400

Leu Asn Ala Ala Ile Glu Ala Ala Arg Ala Gly Glu Ser Gly Lys Gly
                405                 410                 415

Phe Ala Val Ala Glu Glu Val Arg Lys Leu Ala Asp Gly Val Ser
                420                 425                 430

Asp Ser Val Gln Asp Ile Thr Arg Ile Val Asn Gly Thr Gln Gln Glu
            435                 440                 445

Ile Tyr Thr Val Ile Glu Tyr Leu Glu Ser Ser Phe Thr Glu Val Glu
450                 455                 460

Lys Gly Thr Glu Asn Leu Thr Asp Thr Gly Gln Ala Met Gln His Ile
465                 470                 475                 480

Lys Gln Ser Val Thr His Val Ala Asp Ser Ile Lys Glu Val Thr Asp
                485                 490                 495

Gly Leu Lys Gln Leu Thr Asn Gln Ser Ile Thr Ile Asn Gln Ser Ile
                500                 505                 510

Glu Asn Ile Ala Ser Val Ser Glu Gly Ser Ala Ala Gly Ile Glu Glu
            515                 520                 525

Thr Phe Ser Ile Thr Glu Gln Ser Ala His Ser Met Asp Gln Val Leu
530                 535                 540

Gln Asn Ala Glu Glu Leu Glu Gln Leu Ala Lys Glu Leu Asn Glu Lys
545                 550                 555                 560

Met Asn Gln Phe Thr Ile
                565

<210> SEQ ID NO 10
<211> LENGTH: 62
<212> TYPE: PRT
<213> ORGANISM: Pediococcus acidilactici

<400> SEQUENCE: 10

```
Met Lys Lys Ile Glu Lys Leu Thr Glu Lys Glu Met Ala Asn Ile Ile
1               5                   10                  15

Gly Gly Lys Tyr Tyr Gly Asn Gly Val Thr Cys Gly Lys His Ser Cys
            20                  25                  30

Ser Val Asp Trp Gly Lys Ala Thr Thr Cys Ile Ile Asn Asn Gly Ala
        35                  40                  45

Met Ala Trp Ala Thr Gly Gly His Gln Gly Asn His Lys Cys
    50                  55                  60

<210> SEQ ID NO 11
<211> LENGTH: 33
<212> TYPE: PRT
<213> ORGANISM: Lactococcus lactis
<220> FEATURE:
<221> NAME/KEY: SITE
<222> LOCATION: 2
<223> OTHER INFORMATION: Xaa = didehydroaminobutyric acid
<221> NAME/KEY: SITE
<222> LOCATION: 5,33
<223> OTHER INFORMATION: Xaa = didehydroalanine
<221> NAME/KEY: SITE
<222> LOCATION: 8,13,23,25
<223> OTHER INFORMATION: Xaa = aminobutyric acid

<400> SEQUENCE: 11

Ile Xaa Ala Ile Xaa Leu Ala Xaa Pro Gly Ala Lys Xaa Gly Ala Leu
1               5                   10                  15

Met Gly Ala Asn Met Lys Xaa Ala Xaa Ala His Ala Ser Ile His Val
            20                  25                  30

Xaa
```

BACTERIOCIN PRODUCTION, COMPOSITIONS AND METHODS OF USE

CROSS REFERENCE TO RELATED APPLICATIONS

This application is a U.S. national stage application filed under 35 U.S.C. § 371 from International Application Serial No. PCT/US2017/060417, filed on Nov. 7, 2017, and published as WO 2018/089368 on May 17, 2018, which claims the benefit of priority to the filing dates of U.S. Provisional Application Ser. No. 62/419,123, filed Nov. 8, 2016, and U.S. Provisional Application Ser. No. 62/419,145, filed Nov. 8, 2016, the contents of which applications are specifically incorporated herein by reference in their entities.

BACKGROUND

Intestinal microtlora have a role in the health of human hosts (Hawrelak. J. A., & Myers, S. P. (2004). The causes of intestinal dysbiosis: a review. *Altern Med Rev,* 9(2), 180-197). Intestinal (or gut) flora (microbiota) can include a set of microorganisms resident in the alimentary tube, and in an adult man, can include about $10^{13}$ to $10^{14}$ bacteria with only about 150-400 species of different bacteria. There is evidence that a greater diversity of microorganisms in the gut, for example 1000 or more species of microorganisms, would be beneficial.

Some researchers assert that probiotics can positively modulate the intestinal flora of host animals, for example, by restoring the balance of microorganisms in the gut. Such probiotics include non-pathogenic and non-toxic living organisms that can provide health benefits to the host. Examples of probiotic microorganisms that can be beneficial include Lactic bacteria (LAB, Lactic Acid Bacteria), for the most part lactobacilli (order Lactobacillales), and bifidobacteria (order Bifidobacteriales). It should be noted, however, that these organisms are not representative of the whole of the bacterial community residing in or beneficial to the colon. For example, some bacteria in the microbiome can include the orders Bacteroidetes and Clostridiales. Also, the benefits of adding probiotic bacteria to the gut may not be realized because many of the bacteria in probiotic formulations are flushed out of the host within a few days.

A better understanding of the types and activities of microorganisms that can reside and flourish in the intestines of animals can provide insights into the balance of microorganisms useful for optimal probiotic compositions.

SUMMARY

The present invention relates to 'challenger' microbes useful for simulating 'protagonist' microorganisms to make beneficial compounds and materials. The challenger microbes can be contacted with protagonist microorganisms either in in vitro or in vivo to stimulate production of useful compounds or materials.

For example, the challenger microbes can be administered to a subject to stimulate various 'protagonist' microorganisms to synthesize useful compounds or beneficial materials within the gastrointestinal tract of a subject. In other cases, the challenger microbes can be cultured with protagonist microorganisms to produce larger amounts of useful compounds or materials than would be produced without the challenger microbes.

As described and illustrated herein, challenger microbes are microbes that can stimulate protagonist microorganisms to produce higher levels of useful compounds such as one or more lantibiotics, nutrients, anti-proliferative compounds, anti-cancer compounds, or anti-microbial compounds than the protagonist microorganisms would produce in the absence of the challenger microbes. Challenges can occur via commensal and/or agonistic mechanisms, or both, to facilitate the up-regulation of production of one or more beneficial compound or material. Challenges can take place in a selected community of microorganisms, for example, in a gastrointestinal system of an animal.

Compositions that include one or more types of challenger microbes are also described herein. Probiotic compositions that include one or more types of protagonist microorganism are also described. Such probiotic compositions can include, in some cases, one or more types of challenger microbe. In many cases, a challenger probiotic composition without protagonist microorganisms can be prepared and/or administered. However, there may be cases where a protagonist microorganism is included in a probiotic composition with the challenger microbe, or the probiotic composition can contain the protagonist without the challenger microbe. For example, when a challenger microbe is detected in the gut of a subject, the protagonist microorganism can be present in the probiotic formulation without the need to add the challenger microbe to the probiotic composition. In another example, when a protagonist microbe is detected in the gut of a subject, the challenger microbe can be provided in a probiotic formulation that does not contain the protagonist microorganism.

In some methods a prebiotic is included in an administration regimen. For example, a prebiotic can be administered to foster the activity and/or growth of a protagonist microorganism. Such a prebiotic can be administered with the probiotic formulation, or in other cases the prebiotic can be administered separately from the probiotic composition. For example, in some cases it may be helpful to administer a prebiotic composition that can foster the growth of one or more types of protagonist microorganisms that are present in the gut of the subject before administering a probiotic composition that contains one or more types of challenger microbes.

The timing of administration of a probiotic composition and/or a prebiotic formulation can be varied to optimize production of useful compounds and materials by the protagonist microorganism. If a population of protagonist microorganisms is present in the gut of a subject (e.g., endogenously or because a probiotic composition containing the protagonist microorganisms has already been administered) a prebiotic formulation can be administered at various times, for example, to 'feed' the population of protagonist microorganisms and thereby foster the growth of the protagonist microorganisms. A healthy population of protagonist microorganisms can stimulate production of useful compounds and materials when the challenger microbes are administered. When a population of protagonist microorganisms is present in the gastrointestinal system of a subject (e.g., endogenously or because a probiotic composition has already be administered) a probiotic composition containing one or more challenger probiotic microbes can be administered, optionally with a prebiotic formulation, at various times to repeatedly stimulate the population of protagonist microorganisms to produce useful compounds and materials. For example, it may be beneficial to selectively feed challenger microbe(s) by administering a carbon sources in a prebiotic composition with, or at a time following administration of the challenger probiotic composition. Stimulation of challenger microbe growth or metabolism can enhance the challenge (or stress) placed on the protagonist organism(s) so that greater amounts of beneficial compounds or materials are made by the protagonist microorganisms.

The compositions and methods described herein can deliver or induce the production in situ of beneficial compounds and materials to the gastrointestinal system, for example, to any of the following parts of the gastrointestinal system: the mouth, sinus, esophagus, stomach, small intestine, large intestine, colon, bladder, vagina, and combinations thereof.

Another aspect of the invention is a method of manufacturing one or more beneficial compounds or materials that can involve contacting at least one type (species) of challenger microbe with at least one type (species) of protagonist microorganism to form a mixture, and incubating the mixture in a culture medium for a time and under conditions sufficient to manufacture the beneficial compound or material product.

DESCRIPTION OF THE FIGURES

FIG. 9A shows that broth from *Lactococcus lactis* and *Lactobacillus gasseri* cultures reduced HCT-15 colon cancer cell proliferation in a dose-dependent manner relative to control culture media. Proliferation of cells was reduced by 60% at the maximum dose tested indicating a dose of appx. 1.3 µg/g equivalent nisin A. Broth produced using *L. gasseri* demonstrated a clear threshold of effect equivalent to appx. 0.65 µg/g nisin A. FIG. 9B shows that broth from *Lactococcus lactis* and *Lactobacillus gasseri* cultures reduced DLD-1 colon cancer cell proliferation in a dose-dependent manner relative to control culture media. Antiproliferative activity was similar to that observed vs. HCT-15 cells. Again, broth produced with *Lactobacillus gasseri* demonstrated a dose threshold of approximately half of the equivalent dose of Nisin A. The left-most bar in each cluster shows cancer cell growth with no intervention. The second bar (from the left) shows cancer cell growth in the presence of 100 µg/ml of intervention broth indicated as either from *Lactococcus lactis* or *Lactobacillus gasseri*. The third bar (from the left) shows cancer cell growth in the presence of 200 µg/ml control broth. The fourth bar (from the left) shows cancer cell growth in the presence of 400 µg/ml control broth. The fifth bar (from the left or the rightmost bar) shows cancer cell growth in the presence of 800 µg/ml control broth.

FIG. 9C shows a schematic diagram of the structure of nisin A. FIG. 9D shows a comparison of sequences for nisin A (SEQ ID NO:1). nisin Z (SEQ ID NO:2), nisin Q (SEQ ID NO:3), and nisin F (SEQ ID NO:4). As illustrated, nisins can have some uncommon amino acids such as lanthionine (Lan), methyllanthionine (MeLan), didehydroalanine (Dha), and didehydroaminobutyric acid (Dhb). FIG. 9E graphically illustrates inhibition of HCT-15 and DLD-1 colorectal cancer cell proliferation and IC50 values obtained for nisins A and Z. The plot is representative of four triplicate tests including two each for HCT-15 and DLD-1 cells. Note that Nisin A began to precipitate at concentrations >400 µg/mL.

FIG. 10A graphically illustrates that nisin Z inhibits proliferation of DLD-1 colorectal cancer cells. The DLD-1 cells were treated for 24 hours with nisin Z. control cell culture media, or broth from *Lactococcus lactis* and *Lactobacillus gasseri* cultures (base) using 0, 100, 200, 400, or 800 μg/ml total protein diluted with cell culture media. FIG. 10B graphically illustrates that nisin Z produced by *Lactococcus lactis* and *Lactobacillus gasseri* when challenged by *W. viridescens* NRRL B-1951 inhibits proliferation of DLD-1 colorectal cancer cells. Cells were treated for 24 hours with nisin Z. control cell culture media, or broth from *Lactococcus lactis* and *Lactobacillus gasseri* cultures challenged by *W. viridescens* NRRL B-1951 (challenged) using 0, 100, 200, 400, or 800 μg/ml total protein diluted with cell culture media. FIG. 10C graphically illustrates that nisin Z inhibits proliferation of HCT-15 colorectal cancer cells. The HCT-15 cells were treated for 24 hours with nisin Z, control cell culture media, or broth from *Lactococcus lactis* and *Lactobacillus gasseri* cultures (base) using 0, 100, 200, 400, or 800 μg/ml total protein diluted with cell culture media. FIG. 10D graphically illustrates that nisin Z produced by *Lactococcus lactis* and *Lactobacillus gasseri* when challenged by *W. viridescens* NRRL B-1951 inhibits proliferation of HCT-15 colorectal cancer cells. The HCT-15 cells were treated for 24 hours with nisin Z, control cell culture media, or broth from *Lactococcus lactis* and *Lactobacillus gasseri* cultures challenged by *W. viridescens* NRRL B-1951 (Challenged) using 0, 100, 200, 400, or 800 μg/ml total protein diluted with cell culture media. FIG. 10E graphically illustrates average inhibition of DLD-1 and HCT-15 colorectal cancer cell proliferation by *Lactococcus lactis* subsp. *lactis* NRRL B-1821 culture media (Base) and by challenger culture media where *Lactococcus lactis* subsp. *lactis* NRRL B-1821 production of nisins was induced by challenge with *W. viridescens* NRRL B-1951 (Chal). FIG. 10F graphically illustrates average inhibition of DLD-1 and HCT-15 colorectal cancer cell proliferation by *Lactobacillus gasseri* ATCC 4962 culture media (Base) and by challenger culture media where *Lactobacillus gasseri* ATCC 4962 production of nisins was induced by challenge with *W. viridescens* NRRL B-1951 (Chal).

FIG. 11A graphically illustrates inhibition of *Weissella viridescens* NRRL B-1951 growth in the presence of known amounts of nisin A. Note the bimodal distribution where a plateau of tolerance can be observed between 0.46 and 1.54 nanomoles. $R^2$ values express modeled growth % plotted over measured growth %. FIG. 11B graphically illustrates the average activities of nisins A and Z against *W. viridescens* NRRL B-1951 as measured by percent growth of *W. viridescens*. $R^2$ expresses modeled growth % plotted over measured growth %. FIG. 11C illustrates that growth of a susceptible organism is inhibited to a greater extent by a cell-free broth produced by incubation of a challenger microbe (*Weissella viridescens*) with a beneficial microorganism (*Lactococcus lactis*) ("challenged" broth), than by a cell-free broth produced by incubation of the beneficial microorganism alone (*L. lactis* control). Growth of the susceptible organism (*Weissella viridescens*) was detected by a tube assay where fresh *Weissella viridescens* cells were incubated with cell-free broth from a *Lactococcus lactis* culture (dashed line) or a cell-free challenger broth generated by incubation of *Lactococcus lactis* with the challenger microbe, *Weissella viridescens*. FIG. 11D graphically illustrates an increase of antimicrobial activity by the challenger broth in a dose-dependent fashion relative to the control (base broth).

FIG. 12A illustrates a manufacturing method for one or more of beneficial compound and/or material (e.g., one or more bacteriocin). FIG. 12B illustrates a purification method for isolation of one or more of beneficial compound and/or material (e.g., one or more bacteriocin).

DETAILED DESCRIPTION

Figure 1:
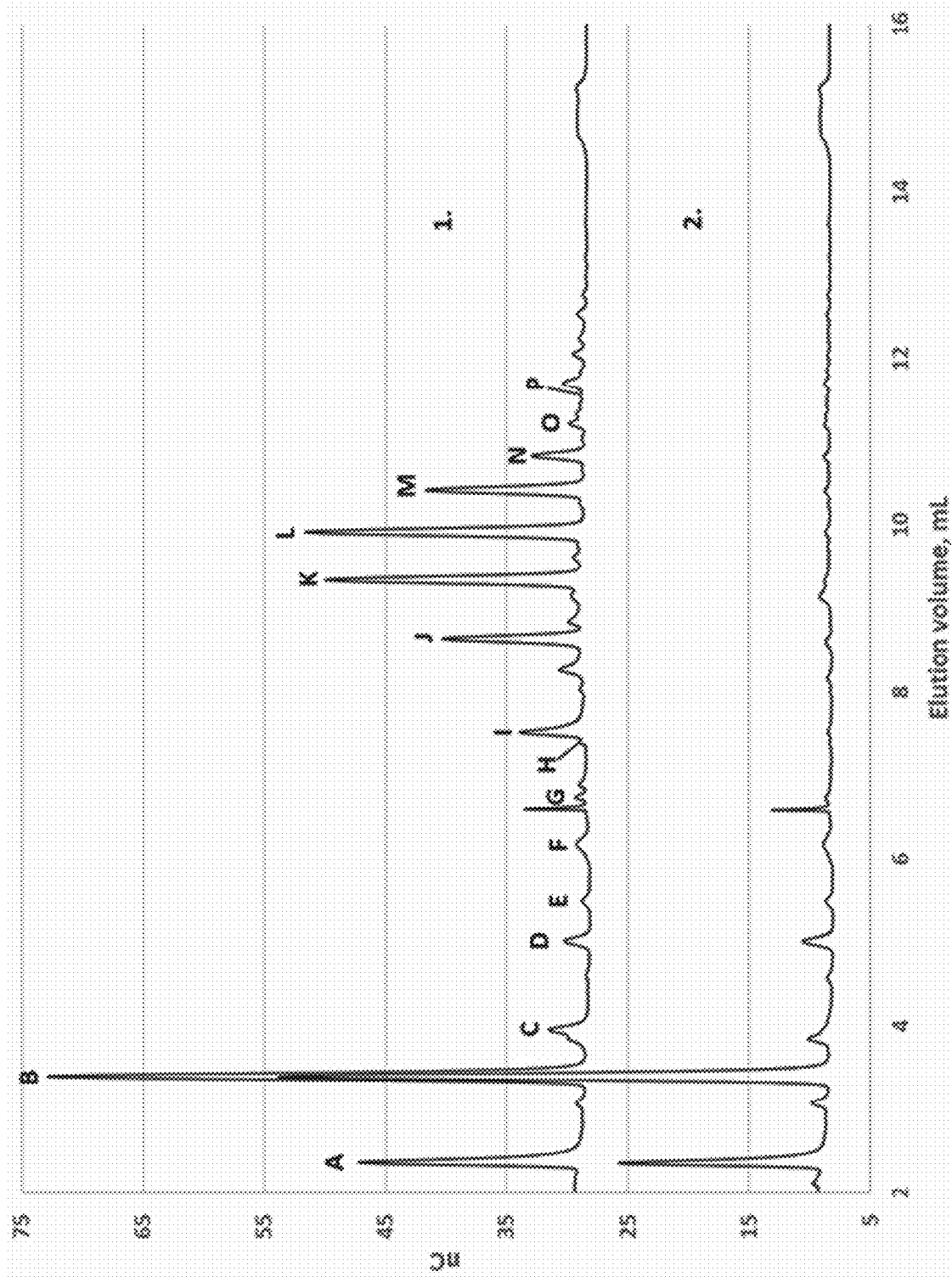
FIG. 1 graphically illustrates consumption of maltosyl-isomaltooligosaccharides (MIMOs; ISOThrive™) as a sole-carbon source of *L. lactis* subsp. *lactis* NRRL B-1821. The graph shows a carbohydrate profile (as detected by HPAEC-PAD showing the relative numbers of different oligosaccharide chain lengths (nC at different elution times) of *L. lactis* subsp. *lactis* NRRL B-1821 after growth in media containing ISOThrive™ MIMO as a sole carbon source. Trace 1: Pre-inoculum media. Trace 2: Media after 21 Hr fermentation. The detected peaks were: A, mannitol; B, L-arabinose (IS); C, glucose; D. unknown DP 2; E. leucrose; F. isomaltose; G, isomaltotriose; H, isomaltotetraose; I, maltose; J. panose (MIMO DP 3); and K-P, MIMO DP 4-9.

This application describes compositions and methods of increasing the production of beneficial compounds or materials by beneficial microorganism. Such beneficial microorganisms can be probiotic microorganisms. As described herein, beneficial 'protagonist' microorganisms can synthesize useful compounds or materials while in culture and also in the gastrointestinal system of an animal. As also described herein, other types of microorganisms can induce such 'protagonist' microorganisms to produce even ore of the useful compounds or materials.

For example, a 'challenger' probiotic composition can be administered to a subject where the 'challenger' probiotic composition includes challenger microbes that (1) stimulate 'protagonist' microorganisms to synthesize useful compounds or materials; (2) produce nutrients or intermediates that can be used by protagonist microorganisms to make useful compounds or materials. The useful compounds or materials made by the protagonist microorganisms can be made in situ, within the gut of the subject and can improve the health of the subject. Hence while the challenger microbes may synthesize intermediates or nutrients for the protagonist microorganisms, the challenger does not directly synthesize beneficial compounds/materials. Instead, the challenger microbes can stimulate protagonist microorganisms to make such beneficial compounds/materials.

Useful compounds and materials can also be manufactured by culturing combinations of 'protagonist' microorganisms and 'challenger' microorganisms, for example, in fermentation vessels or other cell culture systems.

Such methods can, for example, generate one or more anti-cancer, anti-proliferative, and/or anti-microbial compounds in significant quantities. When ingested, or otherwise administered (e.g., via enema or catheter), combinations of 'protagonist' microorganisms and 'challenger' microorganisms can produce such useful compounds or materials within the gastrointestinal system, or other areas, of the body of the subject to combat cancer and infections. For example, production of nisin by various microorganisms can inhibit or kill of tough-to-kill germs such as Methicillin-resistant *Staphylococcus aureus* (MRSA), Carbapenem-resistant Enterobaceriaceae (CRE) and *Clostridium difficile*. Moreover. the risk of developed resistance to the in situ produced beneficial compounds (such as nisin) is small.

In some cases. challenger microbes may be microbe types or species that respond to (e.g., are inhibited by) the beneficial compounds/materials generated by the protagonist microorganisms. Without limiting the scope of challenger microbe species/types, from an evolutionary perspective, protagonist microorganisms may have evolved to produce beneficial compounds/materials to inhibit the growth or activity of challenger microbes that may compete for resources. Hence. in some cases challenger microbes can in some cases be any microbe type or species that exhibits reduced growth/activity in the presence of beneficial compounds/materials produced by protagonist microorganisms.

Beneficial Compounds/Materials Produced by Protagonist Microorganisms

Some strains of protagonist microorganisms that can be present in animal (including human) intestines, or that can be provided in a probiotic mixture, can produce beneficial compounds. materials, and other agents that can improve the health of the host. Challenger microbes can induce such protagonist microorganism to produce such beneficial compounds, materials, and other agents. Hence, even when the challenger microbes do not appear to be directly producing anything of value to a subject they may stimulate other (protagonist) microorganisms to make compounds and materials that can protect the host subject from disease and infection by pathogens, or otherwise improve the health of the subject. Even dead or attenuated challenger microbes can in some cases stimulate the protagonist microorganisms to make compounds and materials that can benefit the subject.

Such protagonist microorganism-produced beneficial compounds or materials can include but are not limited to lantibiotics, bacteriocins, antibacterial compounds, anti-cancer agents. nutrients, vitamins (e.g., B vitamins), short chain fatty acids (SCFAs), hydrogen peroxide. neuromodulators, neurotransmitters (e.g, gamma-aminobutyric acid (GABA)), co-factors (e.g., NAD, cAMP, etc.), and combinations thereof. As described herein, protagonist microorganisms can produce higher amounts of such beneficial compounds or materials in the presence of a challenger microbe than when the challenger microbe is not present.

The microorganism that produces at least one compound or material that is beneficial to the subject is a protagonist microorganism. The microbe that stimulates the protagonist microorganism to do so is a challenger microorganism. However, the roles of the various organisms in the gastrointestinal system of the subject can vary, so that an organism that serves as a challenger microbe in one situation or environment, may serve as a protagonist in another situation or environment. The definition of which microbe to administer to a subject as a challenger microbe can be determined by the condition or disease that a subject may have, or by the balance of organisms that are already within the gastrointestinal system of the subject. The types of protagonist microorganisms that make beneficial compounds and materials are described herein and can be identified by those of ordinary skill in the art. Similarly, the types of challenger microbes that can stimulate a protagonist to make a selected beneficial compound or material are also described herein and can be identified by those of ordinary skill in the art. In addition. as described herein, fecal samples obtained from the subject can be evaluated to determine which microbes or microorganisms are present within a subject and which should be included in a probiotic composition to be administered to the subject. And in many cases the probiotic composition is formulated to include specific types of challenger microbes that will stimulate production of specific beneficial compounds or materials by particular protagonist microorganisms.

For example, a method of administration can involve one or more of the following steps:

1. Administer a probiotic composition containing one or more challenger microbes that may induce production or increased production of beneficial compounds or materials by a protagonist.
2. Administer a probiotic composition containing one or more challenger microbes that produce intermediates that are used by the protagonist to make beneficial compounds or materials.
3. Administer a probiotic composition containing one or more types of protagonist microorganism, where these protagonist microorganisms are typically expelled within a few days.

Hence, the beneficial compounds or materials that are useful to the subject can determine which protagonist and accordingly which challenger microbes are administered. The following describes some of the beneficial agents that can be produced by protagonist microorganisms, and the types of microorganisms that produce them. For example, in some cases, the more desirable protagonist microorganisms produce bacteriocins, antibacterial compounds, anti-cancer agents, or combinations thereof.

Bacteriocins

Bacteriocins are peptides or small proteins, or quaternary structures thereof, that exhibit antimicrobial, antiproliferative, and other useful properties. In some cases, bacteriocins are more active when complexed with other compounds, including other bacteriocins.

The first bacteriocin was discovered by Gratia in 1925 while studying *E. coli*. The bacteriocin produced by *E. coli* was dubbed "colicin." This naming convention became canon, and so hence others are similarly named, e.g. *B. subtilis*=subtilin, *P. acidilactici*=pediocin, and so on.

There are five classes of bacteriocins, which are further subdivided by their molecular definition, their properties, or their activities.

Class I: lantibiotics characterized by the presence of unusual amino acids such as lanthionine or β-methyllanthione. Such unusual amino acids can arise from post-translational modification of the precursor peptide. They are thermostable and resistant to acidic pH. Some are cyclic peptides. A new class of quaternary dual-peptide lantibiotics has been recently discovered, but is not yet classified. Examples include lichenicidin and lacticin 3147. See website at bmcmicrobiol.biomedcentral.com/articles/10.1186/1471-2180-13-212.

Class II: Thermostable non-lantibiotic peptides.
  IIa: Single peptide bacteriocins, for example, exemplified by the pediocins which all exhibit a conserved N-terminal consensus sequence of YGNGV (SEQ ID NO:5; Papagianni and Anastasiadou, 2009).
  IIb: two-peptide bacteriocins, for example, exemplified by lactoccin G/3147, et al. (*Lactococcus lactis* subsp *lactis*; McAuliffe, et al. 1998) and plantaricin E/423/ZJ5/NC8/W. et al. (*Lactobacillus plantarum*, Maldonado. et al. 2004; plantaricin W, and others. are actually a two-peptide lantibiotics and should be re-classified as Class Ib, which isn't yet codified. Holo, et al. 2001).
  IIc: sec (signal peptide)-dependent secreted bacteriocins, of which enterocin P, from *Lactococcus lactis*, is a member (Herranz and Driessen, 2005).

Class III: Heat labile proteins exemplified by helveticin J and caseicin 80.

Class IV: Complex lipoproteins/glycoproteins.

Class V: Cyclic bacteriocins where the amino and carboxy ends are linked. Examples include bacteriocin AS-48 (see website at researchgate.net/publication/8181557_Peptide-_AS-48_prototype_of_a_new_class_of_cyclic_bacteriocins), gassericin A, circularin, and lugdunin (e.g., from *Staphylococcus lugdunesis*, thiazolidine containing; and found to control MRSA in co-culture in-vivo, see website at nature.com/nature/journal/v535/n7613/abs/nature18634.html).

Examples of a highly useful anti-microbial, anti-proliferative, and/or anti-cancer bacteriocins include nisins.

Nisins are lantibiotics, which are a class of ribosomally synthesized, post-translationally modified peptides containing unusual amino acids, such as dehydrated and lanthionine residues. Some lantibiotics are synthetic (e.g., engineered), while some are produced naturally. Lantibiotics are typically bridged by lanthionine residues. Modifications that can be present in lantibiotics (including nisins) include, but are not limited to, glycation, addition of lipid (e.g. phosphatidylcholine, etc.), methylation, and bridging molecules.

Nisin is a lantibiotic bacteriocin produced by *Lactococcus lactis* (*creamoris*, subsp. *lactis*, et al.). It was discovered in 1930, and has been marketed as a food-safe preservative (designated E234) under the trade-name "Nisaplin" by Beaminster (now DuPont) since the 1950s (Jones et al., 2005). Nisin is also available from Handary S. A. (Brussels Belgium). Nisin was named for its activity, "Group N Streptococci Inhibitory Substance," (Zorn and Czermak, 2014).

As the lantiobiotic classification implies, nisin can include a 34-residue peptide (3,353 Da) that can contain the unusual lanthionine, methyllanthionine, didehydroalanine, and didehydroaminobutyric acid residues. There are variants of nisin. For example, nisin can be variant nisin A, variant nisin Z, variant nisin Q, variant nisin F, variant nisin U, or combinations thereof. Some types of nisin are class-one lantibiotic bacteriocins produced by a number of bacterial strains of *Lactococcus lactis* subsp. *lactis*. The A and Z forms of nisin differ only by the residue at the $27^{th}$ position which is either histidine (HIS, A) or asparagine (ASN, Z). Other forms of nisin exist (nisin Q, F, U). An example of a nisin sequence is as follows with the $27^{th}$ position highlighted: ITSISLCTPG CKTGALMGCN MKTATC<u>N</u>CSI HVSK (SEQ ID NO:6). As illustrated, nisins can have some uncommon amino acids such as lanthionine (Lan), methyllanthionine (MeLan), didehydroalanine (Dha), and didehydroaminobutyric acid (Dhb). FIG. 9C shows a schematic diagram of the structure of nisin A. FIG. 9D shows a comparison of sequences for nisin A (MSTKDFNLDLVSVSKKDSGASPRITSISLCTPGCKTGALMGCNMKTATCHCSIHVSK; SEQ ID NO:1), nisin Z (MSTKDFNLDLVSVSKKDSGASPRITSISLCTPGCKTGALMGCNMKTATCNCSIHVSN; SEQ ID NO:2), nisin Q (MSTKDFNLDLVSVSKTDSGASTRITSISLCTPGCKTGVLMGCNLKTATCNCSVHVSK; SEQ ID NO:3), and nisin F (MSTKDFNLDLVSVSKKDSGASPRITSISLCTPGCKTGALMGCNMKTATCNCSVHVSK; SEQ ID NO:4).

Nisins are often post-translationally modified. For example, nisins can include glycosylated moieties as well as post-translationally added amino acids. Nisins can also be post-translationally crosslinked together and form complexes with various types of nisins and other compounds. Hence, the molecular weights of nisins can vary depending upon the extent of such modifications.

Unlike many other bacteriocins, which are remarkably specific with respect to the organisms they attenuate (Reeves, 1979), nisin can exhibit a broad spectrum of activities at very low doses, for example, in the parts per billion (ppb) range. Nisins also are typically thermally stable. Many nisins are also most soluble and stable at acidic pH. Hence, nisins can be autoclaved, for example, at 115° C. and/or subjected to pH 2 conditions for extended periods of time.

Nisins can be active against *Bacillus, Clostridium, Staphylococcus, Streptococcus*, and *Listeria* spp. (Fox, et al. 2000). Nisins can also be effective against gram negative organisms (e.g. *Salmonella* spp.) especially when co-administered with EDTA to prevent binding of the nisin molecules to the peptidoglycan outer coat of the pathogenic species (Stevens, et al. 1991). In some cases, nisin may also be effective against *Campylobacter* spp. As illustrated herein, nisins are also active against *Weissella* spp., such as *Weissella viridescens*.

Some forms of nisin, for example, nisin Z, may be more active than other forms. While some gram negative microorganisms are resistant to bacteriocins, nisin Z will typically exhibit some activity against gram negative microorganisms.

Recently, nisin has been demonstrated to reduce tumorigenesis (head and neck) in mice (Kamarajan, et al. 2015-mouse study; Shin, et al. 2015). For example, researchers have found that nisin Z, a class I lantibiotic bacteriocin, can reduce tumorigenesis in mice (Kamarajan, et al. 2015 PLoS One. 107): 20 pp), presumably via CHAC1 (Joo, et al. 2012 Cancer Medicine 1 (3). pp. 295-305), and that other bacteriocins have been noted to have activity against a variety of cancer cell lines (Kaur and Kaur, 2015). Hence, increasing the population of the organism(s) and/or increasing the metabolic activity of such organisms can increase the quantity of bacteriocin(s) in situ that can exert a positive effect on cancerous/pre-cancerous lesions in the colon (and elsewhere).

TABLE 1

Examples of bacteriocins that can inhibit various cancer types

| Bacteriocin | Organism Producing Bacteriocin | Class | Bacteriocin Size (kDa) | Cancer Cell Type |
| --- | --- | --- | --- | --- |
| Colicin E3 | *E. coli* | III | 9.8 | P388 (lymphoma), HeLa (cervical cancer), HS913T (fibrosarcoma) |
| Colicin A | *E. coil* | III | >20 | HS913T (fibrosarcoma), SKUT-1 (uterine leiomyosarcoma), BT474 (breast cancer), ZR75 (breast cancer), SKBR3 (breast cancer), MRC5 |
| Colicin E1 | *E. coil* | III | 57 | MCF7 (breast cancer), HS913T (fibrosarcoma) |
| Microcin E492 | *K. pneumoniae* | IIa | 7.9 | HeLa (cervical cancer), Jurkat (leukemia), RJ2.25 (B cell line) |

TABLE 1-continued

Examples of bacteriocins that can inhibit various cancer types

| Bacteriocin | Organism Producing Bacteriocin | Class | Bacteriocin Size (kDa) | Cancer Cell Type |
|---|---|---|---|---|
| Pediocin PA-1 | *P. acidilactici* PAC1.0 | IIa | 3.5 | A-549 (lung cancer, adenocarcinomic human alveolar basal epithelial cells), DLD-1 (colon cancer) |
| Pediocin K2a2-3 | *P. acidilactici* K2a2-3 | IIa | 4.6 | HT29 (human colon adenocarcinoma), HeLa (human cervical carcinoma |
| Pediocin CP2 | *P. acidilactici* | IIa | | HeLa (cervical cancer), MCF7 (breast cancer), HepG2 (liver cancer) |
| Pyocin S2 | *P. aeruginosa* 42A | III | 74 | HepG2 (liver cancer), Im9 (myeloma), HeLa (human cervical carcinoma), AS-II (ovarian carcinoma), mKS-A TU-7 (transformed kidney cells) |
| Nisin | *L. lactis* | I | 3.5 | MCF7 (breast cancer), HepG2 (liver cancer) |
| Bovicin HC5 | *S. bovis* HC5 | I | 2.4 | MCF7 (breast cancer), HepG2 (liver cancer) |
| Smegmatocin | *M. smegmatis* 14468 | III | 75 | HeLa (cervical cancer), HGC-27 (gastric cancer), mKS-A TU-7 (transformed kidney cells) |
| Plantaricin A | *L. plantarum* C11 | II | 2.4 | Jurkat (leukemia), $GH_4$ (pituitary cancer), Reh (leukemia), Jurkat (leukemia), PC12 (adrenal chromaffin tumor), N2A (spinal cord tumor), $GH_4$ (pituitary cancer) |

Many types of bacteriocins are produced that can inhibit growth or other functions of a variety of organisms. For example, *Lactobacillus salivarius* (e.g., strain NRRL B-30514) can inhibit the growth of *Campylobacter* spp., such as *Campylobacter jejuni*, *E. coli*, and *Salmonella* spp. Such species of *Campylobacter* and *Salmonella* can colonize the gastrointestinal systems of animals (e.g., humans and poultry) and cause deleterious effects. Fostering the growth and activity of *Lactobacillus salivarius* by including it in a probiotic composition or by providing endogenous *Lactobacillus salivarius* populations with prebiotic compositions suited for growth of *Lactobacillus salivarius* can help control or inhibit *Campylobacter* and *Salmonella* infections. *Lactobacillus salivarius* can in some cases inhabit the oral cavity, nasal cavity, and esophagus so it may be an ideal protagonist for treatment or inhibition of diseases associated with *Campylobacter* and *Salmonella*, such as GERD/chronic acid reflux.

Other examples of bacterial species that can produce bacteriocins are provided in Table 2. Any of the bacteria listed in the second column of Table 2 can be protagonist microorganisms.

TABLE 2

Bacterial species that produce bacteriocins with broad spectrum activity

| Bacteriocin | Bacteria | References |
|---|---|---|
| Microcin S (inhibits *E. coli*), Microcin E492 (e.g., inhibits *Escherichia coli*, *Klebsiella*, *Salmonella*, *Citrobacter*, *Enterobacter*, and *Erwinia*) | *Escherichia coli* G3/10; *Klebsiella pneumoniae* | Zschuttig, et al. 2012; Hetz, et al. 2002. |
| Pediocin A; PA-1 (e.g., inhibits *Listeria monocytogenes*) | *Pediococcus pentosaceus* FBB61, NCDC 273; *Pediococcus acetolactici* PAC1.0 | Piva, et at. 1994; Simha, et al. 2012; Chikindas, et al. 1993; Rodriguez, et al. 2002 |
| Nisin A; Z; ZP; H; U (e.g., inhibits *Weissella* | *Lactococcus lactis* subsp. *cremoris* M104; *Lactococcus lactis* subsp. *lactis* | Lianou and Samelis, 2014; Delves-Broughton, 1990; de Vos, et al. 1993; |

TABLE 2-continued

Bacterial species that produce bacteriocins with broad spectrum activity

| Bacteriocin | Bacteria | References |
|---|---|---|
| *viridescens*; inhibit cancer cell growth) | NIZO 22186; *Streptococcus hyointestinalis* DPC6484; *Streptococcus uberis* strain 42 | Shin, et al. 2016; O'Connor, et al. 2015; Wirawan, et al. 2006 |
| Subtilin (e.g., inhibits *Pseudomonas*, *Bacillus*, *Streptococcus* and, *Listeria monocytogenes*) | *Bacillus subtilis* ATCC6633 | Entian and de Vos. 1996 |
| Plantaricin A; EF; JK; S; W; ZJ5; ST31; K25 (e.g., inhibits *Lactobacillus plantarum* NCDO 965) | *Lactobacillus plantarum* C11, NC8, ZJ5; ST31 | Diep et al, 1994; Maldonado, et al. 2004; Holo, et al. 2001; Song, et al. 2014; Todorev et al, 2004; Lim et al. 2016; Zacharof and Lovitt, 2012 |
| Sakacin A; G; P; C2 (e.g., inhibits *Listeria ivanovi* BUG 496) | *Lactobacillus sakei* Lb706; 2512; Lb674; C2 | Holck, et al. 1992; Simon et al. 2002; Mathiesen et al. 2005; Gao et al 2011 |
| Lactacin B; F (e.g., inhibits *Lactobacillus leichmannii*, *Lactobacillus bulgaricus*, *Lactobacillus helveticus*, and *Lactobacillus lactis*) | *Lactobacillus acidophilus* N2; *Lactobacillus johnsonii* spp.; *Lactobacillus acidophilus* 11088 (NCK88); *Lactobacillus acidophilus* La-5 | Barefoot and Klaenhammer, 1983; Zacharof and Lovitt, 2012; Muriana and Klaenhammer, 1991; Tabasco et al, 2009 |
| Lactocin 27; 160; 705; S (e.g., Lactocin 705 inhibits *Lactobacillus plantarum* CRL691) | *Lactobacillus helveticus* LP27; *Lactobacillus rhamnosus* 160; *Lactobacillus casei* CRL705; *Lactobacillus sake* L45 | Upreti and Hinsdill, 1975; Turovskiy, et al. 2009; Zacharof and Lovitt, 2012; Castellano, et al. 2003; Mortvedt-Abildgaard, et al. 1995. |
| Lactoccin G (e.g., inhibits *Lactococcus lactis*, *Lactococcus* sp. LMGT-2077). | *Lactococcus lactis* spp. | Zacharof and Lovitt, 2012 |
| Lactococcin MN (e.g., inhibits *Listeria monocytogenes*) | *Lactococcus lactis* subsp. *cremoris* | Zacharof and Lovitt, 2012 |
| Leucosin A; A-UAL 187; B-KM432Bz; H; B-Ta11 a (e.g., inhibits *Listeria monocytogenes*) | *Leuconostoc gelidum* UAL 187; *Leuconostoc pseudomesenteroides* KM432Bz; *Leuconostoc carnosum* Ta11a | Hastings, et al. 1991; Zacharof and Lovitt, 2012; Makhloufi et al. 2013; Felix, et al. 1994 |
| Entianin (e.g., inhibits *Staphylococcus aureus* and *Enterococcus faecalis*) | *Bacillus subtilis* subsp. *spizizenii* DSM 15029 | Fuchs, et al. 2011 |
| Gassericin (e.g., inhibits *Listeria monocytogenes*, *Bacillus cereus*, and *Staphylococcus aureus*). | *Lactobacillus gasseri* | |
| Bacteriocin PJ4 (e.g., inhibits *Escherichia coli*, *Bacillus subtilis*, *Pseudomonas aeruginosa*, *Enterococcus faecalis*, and | *Lactobacillus helveticus* PJ4 | Jena, et al. 2013 |

TABLE 2-continued

Bacterial species that produce bacteriocins with broad spectrum activity

| Bacteriocin | Bacteria | References |
|---|---|---|
| *Staphylococcus aureus*). Unnamed | *Lactobacillus delbrueckii* subsp. *Bulgaricus* GLB44 | Tufail, et al. 2011; Michaylova, et al. 2007 |
| Epidermin (e.g., inhibits *Lactococcus lactis*) | *Staphylococcus epidermidis* Tu 3298 | Bierbaum, et al. 1996; Gotz, et al. 2014; Bonelli et al, 2006 |
| Gallidermin e.g., inhibits *Micrococcus flavus* DSM 1790 (A), *Staphylococcus simulans* 22 (B), and *Lactococcus lactis* HP). | *Staphylococcus gallinarum* Tu 3928 (F16/P57) | Bierbaum, et al. 1996; Gotz, et al. 2014; Bonelli et al, 2006; Kellner, et al. 1988 |
| Epilancin K7; 15X (e.g., inhibits *Staphylococcus carnosus* TM300) | *Staphylococcus epidermis* 15X154 | Bierbaum, et al. 1996; Velasquez et al, 2011 |
| Mersacidin (e.g., inhibits *Clostridium perfringens*, *Propionibacterium acnes*, and *Streptococcus pneumoniae*). | *Bacillus cereus* T; *Bacillus* sp. strain HIL Y-85,54728 | Brotz, et al. 1997; Altena, et al. 2000 |
| Bacteriocin Abp118 (e.g., inhibits *Listeria monocytogenes*) | *Lactobacillus salivarius* (e.g., strain NRRL B-30514) | Riboulet-Bisson et al., 2012 |

Antibiotics

Microorganisms are the original source of many antimicrobial compounds. For example, *Bacillus brevis* makes gramicidin, which is one of the first antibiotics to be manufactured commercially. It is a heterogeneous mixture of six antibiotic compounds, all of which are obtained from the soil bacterial species *Bacillus brevis*.

As illustrated herein, *Lactococcus lactis* produces various nisins that inhibit the growth of a challenger microbe (e.g., *Weissella viridescens*).

*Streptomyces* is the largest antibiotic-producing genus, producing antibacterial, antifungal, and antiparasitic drugs, as well as a wide range of other bioactive compounds, such as immunosuppressants. *Streptomyces* species produce over two-thirds of the clinically useful antibiotics of natural origin. For example, members of the *Streptomyces* genus are the source for numerous antibacterial agents such as Chloramphenicol (from *S. venezuelae*), Lincomycin (from *S. lincolnensis*), Neomycin (from *S. fradiae*), and Tetracycline (from *S. rimosus* and *S. aureofaciens*). Further, *S. mediterranei* (renamed *Amycolatopsis rifamycinica* in 2004) was found to produce rifamycin. a broad spectrum antibiotic with few cross tolerances. It is effective against HIV-related tuberculosis, and for the treatment of traveler's diarrhea. An orally active form of rifampicin may reduce the number of advanced glycation end products (AGEs). Incubation with rifampicin can also increase the lifespan of *Caenorhabditis elegans* by up to 60% (Golegaonkar. et al. Aging Cell 14(3): 463-73 (2015). Rifamycin SV demonstrated similar activity. Rifamycin has further been noted to be cytotoxic to ascites tumors (Hughes et al., Oncology 35(2): 76-82 (1978); Hughes & Calvin. Cancer Lett, August 1978), see webpage at digital.library.un.edu/ark:/67531/metadc833842/m2/1/high_res_d/1014065.pdf). In addition, some *Pseudomonas* spp. may produce compounds antagonistic to other soil microbes, such as phenazine-type antibiotics.

Vitamins

Although perhaps 39% of the western population is deficient in some types of vitamins. vegans or vegetarians can be particularly vulnerable to vitamin deficiencies (Pawlak. et al. 2013) because some nutrients required for complete nutrition are typically sourced from meat, for example, cyanocobalamin or vitamin B12. Because meat is expensive and is avoided by vegan/vegetarians, acceptable alternative sources would be beneficial. For example, Table 3 lists bacterial species that may be present in the gut, and that may biosynthesize dietary vitamins.

TABLE 3

Bacteria that Biosynthesize Vitamins

| Vitamin | Bacteria | References |
|---|---|---|
| Riboflavin, vitamin B2 | *Bacillus subtilis*, *Clostridium butylicum* *Clostridium acetobutylicum*, | Lim, et al. 2001; LeBlanc, et al. 2013; Perkins and Pero, 2002; |
| Cobalamin, vitamin B12 | *Propionibacterium freudenreichii*\*, *Lactobacillus reuteri* CRL 1098, *Bacillus megaterium* ATCC 13693, *Nocardia rugosa* DSM43194, *Clostridium thermoaceticum* | LeBlanc, et al, 2013; Martens, et al. 2002; Taranto, et al. 2003; Hollreigl, et al. 1982 |
| Niacin/thiamin/ pyridoxine, vitamins B3, B1, and B6 | *Streptococcus thermophilus* ST5\*\*, *Lactobacillus helveticus* R0052, *Bifidobacterium longum* R0175 | LeBlanc, et al. 2013; B3/B6: Alm, 1982; Shahani and Chandan, 1979; B1/B6: Champagne, et al. 2010 |

TABLE 3-continued

Bacteria that Biosynthesize Vitamins

| Vitamin | Bacteria | References |
|---|---|---|
| Folate, vitamin B9 | Lactobacillus plantarum JDM1, WCFS1; Bifidobacterium adolescentis ATCC 15703; Bifidobacterium dentium Bd1; Streptococcus thermophilus; Lactococcus lactis subsp lactis/creamoris; Lactobacillus delbrueckii subsp. bulgaricus; Propionibacterium thoenii; Propionibacterium acidipropionici; Propionibacterium jensenii; Bifidobacterium pseudocatenulatum; Leuconostoc lactis; Leuconostoc paramesenteroides | Rossi, et al. 2011; LeBlanc, et al. 2007. |
| Menaquinone series, vitamin K1-11 | Lactococcus lactis subsp lactis/creamoris; Leuconostoc Lactis; Brochontrix thermosphacta; Staphylococcus xylosus; Staphylococcus equorum; Bacillus subtilis; Arthrobacter nicotinae | Walter, et al. 2013 |

*Dependent on co-fermentation with L. helveticus which provides essential amino acids (McCarthy, 2004), and has been noted to possibly lower incidence of colon cancer (in rats, Lan, 2008) ostensibly via action of SCFA on cellular mitochondria. (Jan, 2002).
**Commonly associated and synergistic with L. delbrueckii subsp. bulgaricus which is a proteolytic organism (Courtin and Rul. 2003), of which several strains are known to produce bacteriocins (GLB44, BB18, Simova., et al. 2008), and at least one strain, VSL3, is useful (in combination with conventional treatment) in treatment of ulcerative colitis (Ghouri, et al. 2014) via reduction in colonic inflammation (see also L. fermentum, Hegazy and El. Bedewy, 2010).

Short Chain Fatty Acids

Short-chain fatty acids (SCFAs) are one of the metabolites produced in the gut through fermentation of dietary fibers by the anaerobic intestinal microbiota. Such SCFAs have been shown to exert multiple beneficial effects on animal (e.g., mammalian and/or avian) energy metabolism. Three phyla of microorganisms: the Bacteroidetes (gram-negative), the Firmicutes (gram-positive), and the Actinobacteria (gram-positive) are the most abundant in the intestine. The bacterial species in the Bacteroidetes phylum mainly produce acetate and propionate, whereas some members of the Firmicutes phylum have butyrate as its primary metabolic end product.

Different intestinal microorganisms exert a strong impact on energy storage and interact with the host lipoprotein lipase (LPL)-mediated process for triglyceride storage in adipocytes. For example, microorganisms can suppress the intestinal epithelium expression of the LPL-inhibitor fasting-induced adipose factor, while promoting the absorption of polysaccharides from the gut lumen (Backhed et al., 2004). Intestinal microorganisms can also increase glucose uptake in the host intestine and produce a substantial elevation in serum glucose and insulin, stimulating the hepatic lipogenesis.

However, such effects can be modulated by fostering the growth of the types of microorganisms that produce short chain fatty acids such as acetate, propionate, and butyrate as their primary metabolic end products. Gut microbiota can enhance energy yields of what would otherwise be indigestible fibers by processing the indigestible dietary polysaccharides to SCFAs. For example, the SCFAs can constitute a fundamental energy source for human colonic epithelium by providing up to as 85% of the energy requirements of the epithelial cells of the colon. This can be about 5 to 15% of the total energy requirements of some subjects. In some cases up to 30% of dietary calories can be made for the host by the microbial species in the gut. In addition. SCFAs can signal upregulation of serotonin via interaction with the vagus nerve, and may alleviate mood disorders. Some of the benefits of microbial SCFA production in the colon are described in Table 4.

TABLE 4

Health Benefits of Short Chain Fatty Acids in the Colon

| SCFA | Specific Effect | Benefit |
|---|---|---|
| Total SCFA | Lowering of pH | Diminished bioavailability of alkaline cytotoxic compounds. Inhibition of growth of pH sensitive organisms. |
| Acetate | Possible increase in Ca and Mg absorption. Relaxation of resistance vessels. | Diminished fecal loss of Ca and Mg. Greater colonic and hepatic portal venous blood flow. |
| Propionate | Enhanced colonic muscular contraction. Relaxation of resistance vessels. Stimulation of colonic electrolyte transport. Colonic epithelial proliferation. Modulation of gut hormones, e.g., leptin. | Easier laxation, relief of constipation. Greater colonic and hepatic portal venous blood flow. Greater ion and fluid absorption, prevention of diarrhea. Greater absorptive capacity. Protection against diet-induced obesity. |
| Butyrate | Relaxation of resistance vessels. Metabolism by colonocytes. Maintenance of normal colonocyte phenotype. Stimulation of colonic electrolyte transport Modulation of gut hormones, e.g., leptin, | Greater colonic and hepatic portal venous blood flow. Maintenance of mucosal integrity, repair of diversion and ulcerative colitis, colonocyte proliferation. Diminished risk of malignancy. Greater ion and fluid absorption, prevention of diarrhea. Protection against diet-induced obesity. |

The pH of the gastrointestinal system can vary. For example, the pH typically changes from highly acid in the stomach to about pH 6 in the duodenum. The pH can gradually increase in the small intestine from pH 6 to about pH 7.4 in the terminal ileum. However. the pH can drop to about 5.7 in the caecum, then gradually increase to reach about pH 6.4-7.0 in the rectum, or about pH 6.5-6.7 in the rectum. See, e.g., the website at gut.bmj.com/content/29/8/1035. Numerous "micro-climates" of lower pH can also exist that can, for example, surround individual bacteria or clusters of bacteria, and that can produce various acids such that the immediate environment around these organisms may have a lower pH.

Studies of human fecal microbial communities indicate that at pH 5.5 a butyrate-producing bacteria of the Firmicutes phylum such as *Roseburia* spp., *Clostridium acetylbutylicum, Clostridium butylirum, Clostridium beijerinkii, Fuecalibacterium prausnitzii*, or combinations thereof, can make up a substantial percentage (e.g., 20% or more) of the total population of intestinal microorganisms. In some cases, a pH below 5.5 is desirable to improve the activities of various enzymes.

However, when fermentable dietary fibers become limiting in the more distal parts of the large intestine, the luminal pH can increase to 6.5-6.6, and the bacteria that typically produce butyrate tend to stop doing so. Acetate and propionate production, for example by Bacteroidetes-related bacteria, can become dominant in such a higher pH environment. See, e.g., Chakraborti, *World J. Gastrointest Pathophysiol* 6(4): 110-119 (November 2015).

Studies of the interaction between two members of the two major divisions of the human intestinal microbiota: the Bacteroidetes (e.g., *B. thetaioaomicron*) and the Firmicutes (e.g., *E. rectale*) illustrate the syntrophic relationship and interplay between these microorganisms (see, e.g., Mahowald et al., 2009). Syntrophism has been characterized by comparing the whole genome transcriptional profiling of each species in monoassociated and biassociated gnotobiotic mice. According to Mahowald et al. (Proc. Natl Acad Sci USA 106(14): 5859-5864 (2009)), *B. thetaiotaomicron* adapts to the presence of *E. rectale* by the upregulation of polysaccharide utilization loci that confer to the microorganism the capacity to increase the variety of glycan substrates utilized, including those derived from the host and that *E. rectale* is unable to access. *E. rectale* can respond to *B. thetaiotaomicron* with down-regulation of glycoside hydrolases and the up-regulation of three simple sugar transport systems for cellobiose, galactoside and arabinose/lactose, as well as peptide and amino acid transporters. Moreover, the *E. rectale* enzymes involved in the production of butyrate are the most highly expressed in mice having both types of microorganisms in their guts. Taken together, these observations indicate that *E. rectale* is better able to access nutrients in the presence of *B. thetaiotaomicron* and utilizes the *B. thetaiotaomicron*-derived acetate to generate increasing amounts of butyrate in mouse colon. Hence, when acetate is beneficial to the subject, *B. thetaioaomicron* can be a protagonist microorganism that supplies such acetate to the subject. However, when the beneficial compound is butyrate, in the context of the compositions and methods described herein, the *B. thetaiotaomicron* can be a challenger microbe that stimulates *E. rectale* to make SCFAs such as butyrate.

For example, in response to a standard polysaccharide-rich chow diet *B. thetaiotaomicron* upregulates several polysaccharide utilization genetic loci involved in the degradation of dietary plant polysaccharides (e.g., soluble hemicelluloses and some celluloses) and *E. rectale* responds with the concomitant upregulation of sugar transporters and glycoside hydrolases. The final result is a balanced syntrophic metabolism where *B. thetaiotaomicron* processes complex plant polysaccharides and distributes the products of digestion to *E. rectale*, which in turn synthesizes butyrate.

This nutrient interchange between Bacteroidetes and Firmicutes is dramatically interrupted when mice were fed with a high-fat and high-sugar Western-type diet. The highly adaptive *B. thetaiotaomicron* responds to this change in diet by the up-regulation of polysaccharide utilization loci specific for the degradation of the host mucus polysaccharides. While mucolysis is part of the natural mechanism for turn-over of the colonic lining (Corfield et al., Front Biosci 6: D1321-57 (October 2001)), excessive degradation of host mucus polysaccharides can be a cause of inflammation leading to intestinal problems for the host. Completely devoid of glycoside hydrolases that can process host glycans, *E. rectale* responds to the high-fat and high-sugar Western-type diet with the down-regulation of several glycoside hydrolases and sugar transporters, with an overall marked reduction in gut *E. rectale* colonization levels and a lower butyrate production. These data are in agreement with the observations that human subjects fed with diets deficient in complex polysaccharides harbor low levels of butyrate producer Firmicutes, such as *E. rectale* (Duncan et al. 2007) in their gastrointestinal tracts.

The proper balance to avoid these intestinal problems can be achieved by ingestion of the prebiotic compositions described herein that can, for example, contain complex plant polysaccharides that *B. thetaiotaomicron* (a challenger microbe) can process to foster *E. rectale* (a protagonist) synthesis of butyrate.

These interrelationships indicate that microorganisms can form commensal relationships where a first organism provides one type of nutrient or useful compound to a second microorganism who provides a different type of nutrient or useful compound to the first organism. In an example, *Lactobacillus delbrueckii* subsp. *bulgaricus*-*Streptococcus thermophilus* have a synergistic relationship where *L. delbrueckii* subsp. *bulgaricus* can supply peptides and amino acids to *S. thermophilus* and, in turn, with *S. thermophilus* producing folate, formic acid and carbon dioxide. Because *L. delbrueckii* does not make folate, the presence of the compounds made by *S. thermophilus* can benefit *L. delbrueckii*, just as production of peptides and amino acids *L. delbrueckii* can benefit *S. thermophilus*. As described herein, subjects can benefit from such relationships by administering probiotic compositions containing challenger microbes that stimulate endogenous microorganisms (or administered microorganisms) to produce beneficial compounds and materials.

Microorganisms

Examples of microorganisms that can populate animal intestines can include bacterial species, yeast species, and combinations thereof. For example, probiotic compositions can include one or more of *Lactobacillus acidophilus, Lactobacillus bulgaricus, Lactococcus lactis* (subsp. *lactis/creamoris*), *Lactobacillus delbrueckii, Lactobacillus fermentum, Lactobacillus gasseri, Lactobacillus helveticus, Lactobacillus johnsonii, Lactobacillus plantarum, Lactobacillus paracasei, Lactobacillus reuteri, Lactobacillus rhamnosus, Lactobilhus sakei, Leuconostoc gelidum, Leuconostoc pseudomesenteroides, Leuconostoc carnosum, Arthrobacter nicotinae, Bacteroides thetaiotaomicron, Bifidobacterium adolescentis, Bifidobacterium bifidum, Bifidobacterium dentium, Bifidobacterium infantis, Bifidobacterium longum, Bacillus rereus, Bacillus roagulans, Bacillus megaterium, Bacillus subtilis, Bacillus subtilis* ATCC6633, *Brochontrix thermosphacta, Clostridium butylicum, Clostridium acetobutylicum, Clostridium thermoaceticum, Escherichia coli* strain G3110, *Escherichia coli* strain G12, *Escherichia coli* strain G4/9. *Escherichia coli* strain GS, *Escherichia coli* strain G6/7, *Escherichia coli* strain G8, *Eubacterium rectale, Eubacterium eligens, Klebsiella pneumoniae, Mycobacterium smegmatis, Nocardia restricta, Nocardia rugosa, Nocardia salmonicida, Pediococcus acidilactici, Pediococcus pentosaceus* FBB61, *Propionibacterium acidipropionici, Propionibacterium freudenreichii, Propionibacterium jensenii, Propionibacterium thoenii, Saccharomyces* sp., *Saccharomyces boulardii, Staphylococcus aureus, Staphylococcus epidermidis, Staphylococcus equorum, Staphylococcus gallinarum, Staphylococcus lugdunensis, Staphvlococcus nepalensis, Streptococcus salivarius, Staphylococcus surcinus, Staphylococcus xylnsus, Streptococcus hyointestinalis* DPC6484, *Streptococcus uberis* strain 42, *Streptococcus thermophilus*, and *Weissella viridescens*. Any of these microorganisms, as well as any other microorganisms described herein or known to those of ordinary skill in the art can be included in the probiotic compositions.

In some cases, the challenger microbes can be living microbes. But in other cases the challenger microbes can be dead or attenuated microbes. For example, the challenger microbes can in some cases stimulate protagonist microorganisms to make beneficial compounds and materials even when the challenger microbes are no longer alive.

While many of the bacterial species and strains thereof described in this application can act as beneficial probiotic microorganisms that provide challenger and/or protagonist microorganism functions, some of the mentioned microorganisms can have negative health effects. In general, a disease-causing microorganism or a microorganism that causes various adverse reactions or conditions in a subject may not be a challenger or protagonist microorganism that is included in the probiotic composition administered to a subject. However, such disease-related microbes can in some cases be included in a probiotic composition, for example, when the disease-related microbe is dead or attenuated (e.g., not capable of reproduction).

Some types of microorganisms that can be found in the intestines of animals and that can have negative effects on the health of an animal subject, include but are not limited to: *Clostridium difficile, Clostridium perfringens, Campylobacter* spp., *Porphyromonas asaccharolytica, Listeria monocytogenes, Leuconostoc* pseudomesenteroides (urinary tract infections), enterohemorrhagic *E. coli* (EHEC), enteroinvasive *E. coli* (EIEC), *Pseudomonas aeruginosa, Salmonella enterica, Salmonella typhi, Salmonella paragyphi* A, *Salmonella schottmuelleri, Salmonella hirschfeldii, Streptococcus bovis, Yersinia enterocolitica*, and combinations thereof. These types of microbes can be examples of disease-related microbes that can be included in the probiotic compositions as challenger microbes, for example, when the disease-related microbes are dead or attenuated (e.g., not capable of reproduction).

In addition, many negative health effects related to gut microorganisms are a result of a host diet that lacks the diversity and/or sufficient quantities of prebiotic carbohydrates to provide energy sources for the diversity of microorganisms in the gut. When gut microorganisms do not have access to the types of carbohydrates they can thrive on. the microorganism can turn to digestion of gut wall components, including mucins and intestinal wall coatings that would protect the intestine from erosion, irritation, inflammation, and disease. For example, microorganisms such as *Bacteroides thetaioaomicron* exhibit hierarchical sugar and carbohydrate preferences (see, e.g., Degnan & Macfarlane, Anaerobe 1(1): 25-33 (1995)).

Hence, at least some of the adverse effects of certain microorganisms can be ameliorated by administration of a prebiotic composition that contains the types of carbohydrates that are preferred by desirable gut microorganisms, such as the protagonist microorganisms described herein.

Moreover, the response of a subject (e.g., a human or animal) to various microorganisms can be affected by the health (or lack of health) of the subject, as well as by the ratios of the amounts of the different types of microorganisms administered to the subject or to which the subject is exposed. Hence, some microorganisms may cause a condition or disease in one subject but not in another. Thus, in some cases a type of microorganism that may be associated with some types of conditions or diseases in one subject can be a challenger or protagonist microorganism that is included in a probiotic composition for another subject.

Microorganisms that produce quorum sensing peptides can also be included in the probiotic compositions. for example, as challenger microbes. Quorum sensing peptides are signaling molecules that in some instances can stimulate or respond to population. Microorganisms can use quorum sensing to coordinate certain behaviors such as bacteriocin synthesis, antibiotic resistance, leader cleavage, chaperone protein synthesis, biofilm formation, and virulence, for example, based on the local density of the bacterial population. Quorum sensing can occur within a single bacterial species as well as between diverse species. A variety of different molecules can be used as signals including oligopeptides produced by Gram-positive bacteria, N-acyl homoserine lactones (AHL) in Gram-negative bacteria, and a family of autoinducers known as autoinducer-2 (AI-2) in both Gram-negative and Gram-positive bacteria. Any such quorum sensing microorganisms can be included in the probiotic compositions.

When such quorum sensing microorganisms are disease-related, the quorum sensing microorganisms can be included in the probiotic compositions as dead or attenuated challenger microbes.

Testing to evaluate the types and relative abundance of each type of microorganism present in a subject's fecal sample can facilitate the design of optimized prebiotic compositions with the objective of gently and effectively rebalancing the gut or another area of the body with microbiota that improve the health of such a subject. See, U.S. application Ser. Nos. 62/368,851 (filed Jul. 29, 2016) and 62/375,345 (filed Aug. 15, 2016), which are specifically incorporated by reference herein in their entireties.

In some cases, a population of challenger microbes can be included in probiotic compositions along with a population of protagonist microorganisms. In other cases, a population of challenger microbes can be included in probiotic compositions without a population of protagonist microorganisms. For example, a challenger probiotic composition can be developed and administered with or without a protagonist probiotic composition. Similarly, a protagonist probiotic composition can be administered with or without a challenger probiotic composition. A decision to administer probiotic compositions that contain challenger and/or protagonist microorganisms can be made based on testing that determines what types of gut microorganisms are present in the intestines of a subject. Moreover, a balanced probiotic composition can be administered to a subject based upon an understanding of the types of conditions or diseases (or the absence of such conditions and diseases) that a subject may have.

The probiotic compositions can be administered according to a regimen that benefits the health of the subject. For example, the probiotic compositions can be administered every day, or every two days, or every three days, or twice per week, or once per week, or once per two weeks, or once per month, or combinations thereof. For example, dosages of the probiotic composition containing about $10^9$-$10^{11}$ CFU microbes/microorganisms can be administered.

Methods for Selecting Probiotics and/or Prebiotics for Administration

Methods of identifying optimal prebiotic formulations and/or probiotic compositions for the individual needs of a subject can involve one or more of the following steps.

One or more fecal samples can be obtained from an animal (e.g., a mammalian or avian) subject. The diversity of microorganisms in the sample(s) can be determined. For example, RNA can be isolated from a sample and the ribosomal RNA sequences (e.g. 16S or 23S rRNA sequences) can be determined to identify what types of microorganisms reside in the gut of the subject who provided the sample. The types of microorganisms in the samples can also be determined by available microbiological methods, and/or from sequencing other types of RNA or via sequencing of selected genomic genes. Whole genomic sequencing can also be employed, for example, using shotgun (de novo) methods. In some cases, the numbers or proportions of types/classes of microorganisms can be determined by quantifying the classes of glycolytic enzymes encoded by the population of microorganisms in a sample. The types and proportions of the carbohydrate metabolizing enzymes in the population of sample microorganisms not only facilitates design of the prebiotic composition, but also can help with definitive identification of the species and strains of microorganisms in the sample. If further information is desired on the types of microorganisms in a sample, sample can be diluted, the microorganisms can be separated and then subcultured to evaluate what agents (e.g., bacteriocins, short chain fatty acids, vitamins, anti-cancer agents, antibiotics, hydrogen peroxide. neuromodulators, neurotransmitters (e.g, gamma-aminobutyric acid (GABA)), co-factors, or combinations thereof) the microorganisms can produce.

In some cases, the method can involve: (1) acquiring a fecal sample, (2) sequencing to identify what types of microorganisms are in the sample (e.g., using one or more of the methods noted above), (3) identifying what enzymes break down carbohydrates for one or more (sometimes most) of the microorganisms in the sample. and identifying which carbohydrates are preferred by which microorganisms; (4) identifying transport mechanisms to determine which carbohydrate break down residues may be used for metabolism. (5) identify what agents each organism is capable of producing.

One or more microorganisms is selected for growth or for inhibition of growth in the subject's gut based upon one or more of its properties. One factor that is considered is an ability to synthesize helpful or unhelpful compounds or materials. Another factor is the physiological state of the subject. For example, the selection of a naturally present microorganism to increase or decrease the growth thereof can relate to analysis of whether the subject has one or more diseases or conditions, and a determination of which functions, properties, or agents a microorganism detected in the sample may provide to the subject.

For example, subjects may have one or more diseases or conditions. Examples of diseases or conditions can include cancer, pre-cancerous condition(s) or cancerous propensities, diabetes (e.g., type 2 diabetes, or type 1 diabetes), autoimmune disease(s), vitamin deficiencies, mood disorder(s), degraded mucosal lining(s), ulcerative colitis, digestive irregularities (e.g., Irritable Bowel Syndrome, acid reflux, constipation, or a combination thereof), inflammatory bowel disease, ulcerative colitis, Crohn's disease, gastroesophageal reflux disease (GERD), infectious enteritis, antibiotic-associated diarrhea, diarrhea, colitis, colon polyps, familial polyposis syndrome. Gardner's Syndrome, *Helicobacter pylori* infection, irritable bowel syndrome, and intestinal cancers. Protagonist microorganisms can produce beneficial compounds and materials to ameliorate such diseases and conditions. For example, as illustrated herein, fostering the growth and activity of certain types of bacteria (e.g., *L. lactis* strains) leads to the production of various types of bacteriocins (e.g., nisins) that can act as anti-cancer agents and/or as anti-microbial agents.

Fostering the growth and activity of protagonist microorganisms can therefore provide multiple benefits to a subject. As illustrated herein, the presence of a challenger microbe stimulates a protagonist microorganism to produce even more bacteriocin (e.g., nisin) than it otherwise would.

However, protagonist microorganisms also need to be fed to provide optimal production of useful compounds and materials. For example, intestinal wall inflammation is a common health problem that is often related to microbial irritation of the intestinal wall, or even microbial digestion of intestinal wall components. If gut microorganisms do not have preferred substrates for growth they can digest secondary or less preferred substrates. For example, gut microorganisms can digest mucins that line the intestinal wall when preferred carbohydrate substrates are not available. Such digestion of mucins can weaken the intestinal wall, and even lead to exposure of intestinal wall proteins and bacterial proteins to the immune system. which can initiate rounds of immune reactions and inflammation. Such problems can be reduced or obviated by ingestion of an appropriate prebiotic composition that contains one or more of the carbohydrates that are preferred by each intestinal microorganism.

The properties of the various microorganisms in the sample can be determined to identify which microbial functions/metabolites can be upregulated or downregulated to optimally serve the subject from which the sample was obtained. The properties of the various microorganisms in the samples are identified, for example, by reference to the teachings herein or other information. For example, the properties of the different microorganisms can include an ability to synthesize bacteriocins, short chain fatty acids (SCFAs), vitamins, anti-cancer agents, antibiotics, hydrogen peroxide, neuromodulators, neurotransmitters (e.g, gamma-aminobutyric acid (GABA) and/or serotonin), co-factors, or combinations thereof. These properties can be determined by reference to the genomic sequences of the microorganisms.

Carbohydrate preferences of one or more selected microorganisms (that has or have been detected in the sample) are identified. This can be done by identifying specific types of enzymes that are encoded by the genome(s) of the one or more microorganism(s). Because the identities of microorganisms in fecal samples can be identified with certainty, and the genomic sequences of such microorganisms are available, the identities of enzymes that digest one or more carbohydrates can be identified with certainty.

Carbohydrate preferences can be dictated by the ability of one or more microorganisms to synthesize enzymes that degrade those carbohydrates, and also by the enzymes or proteins that can transport certain carbohydrates into the microbial cell. An enzyme can be synthesized in response to the presence of a given substrate or in the absence of a preferred substrate. Glucose and glucose-containing oligosaccharides are often a preferred substrate for many microbial metabolic enzymes.

Carbohydrate preferences of a community of microorganisms can be predicted by identification of intracellular, extracellular, or periplasmic space enzymes that digest complex carbohydrate prebiotics to generate simpler saccharides that are readily used by various members of the microbial community. For example, carbohydrates can be processed in the periplasmic space of some bacteria by a variety of enzymes that can signal carbohydrate preferences. A potential for such periplasmic space processing can be identified by interrogating whether carbohydrate transporters are encoded by the genome of the subject organism(s).

Examples of enzymes that can signal carbohydrate preferences include glycoside hydrolases (GH), glycosyl transferases, polysaccharide lyases (PL), carbohydrate esterases, dehydrogenases, carbohydrate transporters, and combinations thereof. The website at www.cazy.org lists types of carbohydrate active enzymes as well as providing information about the enzymes, such as which species has such enzymes, structural information about the enzymes, enzyme activities, substrate preferences, co-factor requirements. For example, the carbohydrate preferences of one or more selected microorganisms can be identified by determining whether one or more of the following types of enzymes are encoded by the genome(s) of the selected microorganism(s): alpha-glucosidases, beta-glucosidases, fructosidases, galactosidases, sucrases, sucrose-isomaltases, invertases, glucuronidases, glucose oxidases, maltases, amylases, isoamylases, beta-phosphoglucomutases, dextranases, pullulanases, mutanases, sialidases, glucosaminase, galactosaminases, xylanases, cellulases, pectinases, and others. The carbohydrate preferences of one or more selected microorganisms can also be identified by determining whether carbohydrate transport proteins such as phosphoenolpyruvate: carbohydrate phosphotransferase system (PTS) are encoded by the genome(s) of the selected microorganism(s).

Methods for identifying the carbohydrate preferences of one or more selected microorganisms can include identification of particular enzyme sequences encoded within the genomes of those selected microorganisms by use of various databases of sequence information. Examples of databases with useful information include the databases and tools available from the National Center for Biotechnology Information (see website at www.ncbi.nlm.nih.gov/), the databases and tools available from UniProt (see website at www.uniprot.org/), the databases and tools available from ExPASY (see website at web.expasy.org), the databases and tools available from Swiss-Prot (see website at web.expasy.org/docs/swiss-prot), the databases and tools available from bacteria.ensembl.org. the databases and tools available from green genes (see website at greengenes.lbl.gov), the databases and tools available from the Microbial Genome Database (see website at mbgd.genome.ad.jp), or a combination thereof.

Some microorganisms can metabolize more than one type of carbohydrate, but there is typically a distinct hierarchy of carbohydrate preferences, where in the presence of two or more carbohydrates, the organism will shift to consuming the most preferred carbohydrate. By way of example, as a survival mechanism, a variety of bacteria have evolved to consume part of the gut mucosal lining when their preferred energy sources (specific types of carbohydrates. frequently containing mostly glucose) are not available. But when presented with a preferred type of carbohydrate, the bacteria shift to metabolizing the preferred carbohydrate source and away from the mucosal lining. One example is *Bacteroides thetaiotaomicron*, which is commonly found in the human colon and which can degrade many different complex carbohydrates (glycans). Although *Bacteroides thetaioaomicron* can and will digest mucins that are found in the human intestine. it will also repress expression of genes involved in degrading lower priority carbohydrates (glycans) when higher priority (preferred) types of carbohydrates (glycans) are available. See, Rogers et al., Molec Microbiol 88(5): 876-90 (2013). *Bacteroides thetaiotaomicron* preferentially express the enzymes that degrade amylopectin and pectin galactin, but amylopectin is its more preferred carbohydrate source.

In addition. some microorganisms encode enzymes that degrade certain carbohydrates yet lack the intracellular transport mechanisms to utilize the breakdown products as an energy source. Such enzymes can be extracellular enzymes that are secreted into the surrounding environment. The products of such enzymatic action can feed other gut bacteria. In effect, the microorganisms that encode such enzymes are factories that behave as 'chefs' or 'prep cooks' for other bacteria that can make use of these breakdown products. For example, prebiotic compositions can be designed for these microorganism 'prep cooks.' which can then breakdown carbohydrates in administered prebiotic compositions so the breakdown products can feed other gut microorganisms. Hence, if one type of gut microorganism produces useful products for a host subject, but if that microorganism does not encode the types of carbohydrate-metabolizing enzymes that can readily digest the carbohydrates in a prebiotic composition. the prebiotic composition can be designed to provide carbohydrates to a 'prep cook' microorganism that supplies the enzymes to breakdown the carbohydrates and produce products that feed, and thus increase the population and/or metabolic activity of other selected microorganisms.

Hence, different types of microorganisms can engage in competition, syntrophy, or cross-feeding with other types of microorganisms.

With consideration for the hierarchy of carbohydrate preferences in the subpopulations of microorganisms selected for modulation, a specific carbohydrate profile is identified for a prebiotic composition that when delivered to the gut will increase the population and/or robustness of the targeted organism(s), or alternatively, will reduce the carbohydrate availability to organisms populations we wish to reduce (and/or in some cases, accomplish both at the same time to achieve a desired outcome).

While certain organisms are carbohydrate 'finicky,' and others are more carbohydrate 'omnivorous.' A carbohydrate preference hierarchy can be determined so that a preferred formulation of prebiotic carbohydrates can be manufactured that targets one or more gut microorganisms with specificity. The carbohydrate 'finicky' microorganisms can be provided with the types of carbohydrates that foster their metabolism and growth, while other carbohydrates in the formulation are available for the carbohydrate 'omnivorous' microorganisms. If inhibition of one or more microorganism is desired, the types of carbohydrates that would normally be metabolized by those microorganisms can be reduced or eliminated from the formulation. Hence, the growth or activities of different organisms can be manipulated by providing optimized, individualized prebiotic compositions to a subject.

The prebiotic carbohydrate compositions can be formulated to target specific health issues of individuals. For example, vegetarians often need vitamin B12 supplements due to the lack of meat consumption in their diet. The needs of such vegetarians can be served by ingestion of a prebiotic carbohydrate formulation that can upregulate the activity or growth of microorganisms in the gut with the capability of producing vitamin B12. For a specific individual host subject, identifying the organisms present in the gut that are capable of producing vitamin B12. as well as the carbohydrate preference hierarchy of those organisms and any energy transporters that may facilitate growth and metabolism by those organisms, determines the blend of prebiotic carbohydrates that would not only optimally foster microorganisms for vitamin B12 production, but would also balance the population of microorganisms in the gut. For example, there may also be a need to increase butyrate production to inhibit or reduce "leaky gut" syndrome and the inflammatory conditions that are often associated with intestinal and other disease states. The prebiotic formulation can also provide carbohydrates to specific types of microorganisms that are capable of producing both vitamin B12 as well as short chain fatty acids (SCFAs) such as butyrate. Hence, the methods and formulation described herein can be tailored to the needs of each unique individual.

In another example, vitamin B12 deficiencies may be addressed in populations of vegetarians/vegans by analysis of collected bacterial populations from a wide swath of vegetarians/vegans so that the types of bacteria found in these vegetarians/vegans are determined and a blend of carbohydrates is made that would target the potential vitamin B12 producing bacteria that are likely to exist in any given host. This approach is less individualized yet can still be effective at achieving an amelioration of a targeted condition.

In addition, such formulations can be adjusted from time to time to meet newly developing health issues. For example, in the event of a diagnosis of colon cancer, the prebiotic compositions can be formulated to foster the growth and/or metabolic activity of specific microorganisms that can produce bacteriocin(s) and other useful factors. Such bacteriocins and other factors can treat or inhibit the growth and metastasis of specific cancer(s). Once the cancer had been eradicated, the portion of the prebiotic composition that was intended to produce higher than normal levels of bacteriocins, could be reduced to provide a lower maintenance level of cancer preventative protection.

As illustrated in the Examples provided herein, *Lactococcus lactis* is present at low levels and is stable in the baseline average population of microbiota in the human gut. The population of *Lactococcus lactis* in a human test group (N=133 increased by a factor of ten within 6-12 weeks of a trial where the human subjects consumed a specific type of prebiotic—maltosyl-isomaltooligosaccharides (MIMOs, not to be confused with IMOs, or fermented IMOs). The enhanced growth of this organism was predicted to occur by virtue of its genealogical encoding for the expression of DexA and DexB encoding for oligo-1,6-glucosidase and 1,6-glucosidase. The expression of oligo-1,6-glucosidase and 1,6-glucosidase was confirmed via in vitro fermentation by *Lactococcus lactis* subsp. *lactis* NRRL B-1821 using MIMO (ISOThrive™) as a sole carbon source. Analysis described herein shows that *Lactococcus lactis* has a weighted prebiotic index (Prbl) for MIMO of at least 60, or at least 83. The utility of such a prebiotic index was demonstrated because MIMO did in fact stimulate the growth of *Lactococcus lactis* in the gut by ten-fold. Broth from fermentation of *Lactococcus lactis* subsp. *lactis* NRRL B-1821 contains beneficial bacteriocins, as illustrated by antimicrobial activity assays, and as observed via various assays (see the Examples).

These and other experimental results show that the methods described herein identify which organisms are natively present in the human gut, as well as which of these organisms can consume a given prebiotic (e.g., based on genes encoding the appropriate hydrolase enzymes). This application also demonstrates that the population of the bacteria natively present in the gut can be manipulated in a predetermined way via introduction (administration) of an individualized prebiotic composition. The prebiotic composition can be selected to favor specific groups of bacteria that naturally produce particular types of beneficial agents (e.g., bacteriocins, vitamins, anti-cancer agents, antibiotics, short chain fatty acids (SCFAs), hydrogen peroxide, neuromodulators, neurotransmitters (e.g, gamma-aminobutyric acid (GABA)), antioxidants, co-factors, and combinations thereof). The population of the bacteria present in the gut can be monitored during the course of intervention so that the prebiotic composition can be tailored to balance the types of bacteria in the gut as desired. Similarly, the prebiotic composition may be a tailor-made cocktail of various prebiotic compositions that is specific for the microbiome of an individual person.

In some cases the methods for providing an optimized prebiotic composition to a subject can involve: identifying what health issues a subject may have (e.g. B12 deficiency, biopsied and thus identified colon cancer, *Clostridium difficile* overgrowth, etc.; sequence nucleic acids from the subject's fecal sample; identify microbial species in the sample (and optionally identify the relative numbers or ratios of different types of microbial species in the sample); cross-reference identified species vs. genes that can produce the agent(s) that can ameliorate the subject's health issues; provide at least one prebiotic composition that can foster (growth and/or metabolism of) microbial species that can produce the agents that can ameliorate the subject's health issues.

The prebiotic composition can be administered to the subject. After ingestion of the prebiotic composition for at least a week, or at least two weeks, or at least three weeks or at least a month, or at least five weeks, or at least 6 weeks, or at least two months, another sample can be evaluated to identify what microbial species are present and in what amounts (ratios). Any changes in the types. diversity, or ratios of microbial species can be correlated with the health or clinical status of the subject.

The amounts or types of carbohydrates in the prebiotic compositions can also be varied to address any new health issues or to improve the composition formulation in any way.

In some cases, the methods for selecting an optimized prebiotic carbohydrate composition can include a step-wise design of a prebiotic composition to include carbohydrate substrates that will first obviate common intestinal problems and then address the particular needs of a subject. For example, (1) a baseline formulation can be identified that includes substrates for organisms that can consume mucin or gut lining components. (2) then carbohydrate substrates are identified that address specific health concerns (e.g., by including substrates for gut microbes that can produce bacteriocins, vitamins, short chain fatty acids (SCFAs), anti-cancer agents, neuromodulators, neurotransmitters (e.g. gamma-aminobutyric acid (GABA)), co-factors (e.g., NAD, cAMP, etc.), and combinations thereof), (3) identify preferred carbohydrate substrates for each organism detected in a subject's fecal sample, and (4) evaluate a proposed prebiotic composition against the balance of the bacterial population in a subject's sample and adjust the types and amounts of carbohydrates in the composition to reduce and/or minimize carbohydrate competition for the organisms targeted for activity change. These steps are described in more detail below Identification of a Baseline Formulation A baseline healthful mixture would include substrates in sufficient quantities to match no less than the second to least preferred substrate so that all organisms would refrain from mucin consumption and gut barrier degradation. This assumes, and is backed by DNA sequence analysis, that all commensal bacteria have gut mucin as their least preferred substrate.

Health Changes by Activity Modification

After determining what health conditions can be adjusted by specific organism metabolites, the organisms that need modification of population sire and/or metabolic activity can be chosen. The choice of prebiotic carbohydrate formulation to achieve a change in outcome is determined by (a) sorting all bacteria in order of the fewest encoded enzymes (i.e. "most carbohydrate finicky") to the most encoded enzymes (i.e. "most carbohydrate omnivorous) and then by their preferred substrates from most to least preferred. Next, the subset of organisms that need activity adjustment are (a) sorted in order of the fewest encoded enzymes (i.e. "most carbohydrate finicky") to the most encoded enzymes (i.e. "most carbohydrate omnivorous) and then by their preferred substrates from most to least preferred.

Draft Carbohydrate Mix

When increasing activity is desired, an initial draft carbohydrate mix is determined and would include the most preferred substrate for each organism whenever possible. When doing so would create a conflict between organisms because of an overlap of preferred substrate, additional amounts of the common substrate would be included in the mix. Alternatively, in the event that one or more organisms are more "omnivorous" a substrate that is less than the most preferred can be substituted so that each organism is able to perform at a sufficient level of efficiency.

Final Carbohydrate Mix

The draft mix is evaluated against the balance of the bacterial population and adjusted as needed so as to reduce and/or minimize carbohydrate competition for the organisms targeted for activity change. In general, for all organisms that are more omnivorous and whenever it is possible to include a more preferred substrate, these organisms will be "distracted" and not compete for the energy sources targeted for the organisms be manipulated.

The relative amounts of each substrate can be calculated by using (a) the starting relative populations and (b) rate of metabolic activity of each organism and these amounts can be modified to include projected increases/decreases in population of the organisms targeted to achieve a desired change in microbial gut activity. This process is illustrated in the charts shown below.

| *Bacterium* A Carbohydrate Consumption Preference Table | |
| --- | --- |
| Enzyme Encoding | Carbohydrate Energy Source |
| Enzyme 1 | Carbohydrate 1 |
| Enzyme 2 | Carbohydrate 2 |
| Enzyme 3 | Carbohydrate 3 |
| Enzyme 4 | Carbohydrate 4 |
| Enzyme 5 | Carbohydrate 5 |
| Enzyme 6 | Carbohydrate 6 |
| Enzyme 7 | Carbohydrate 7 |

| *Bacterium* B Carbohydrate Consumption Preference Table | |
| --- | --- |
| Enzyme Encoding | Carbohydrate Energy Source |
| Enzyme 3 | Carbohydrate 3 |
| Enzyme 1 | Carbohydrate 1 |
| Enzyme 2 | Carbohydrate 2 |

| *Bacterium* C Carbohydrate Consumption Preference Table | |
| --- | --- |
| Enzyme Encoding | Carbohydrate Energy Source |
| Enzyme 5 | Carbohydrate 5 |
| Enzyme 6 | Carbohydrate 6 |

| *Bacterium* D Carbohydrate Consumption Preference Table | |
| --- | --- |
| Enzyme Encoding | Carbohydrate Energy Source |
| Enzyme 7 | Carbohydrate 7 |

Desire to Increase Activity of Bacterium C and Bacterium D

The carbohydrate mix would include Carbohydrates 5 and 7 for the targeted bacteria as well as 3 and 1. In this case, although Bacterium A is capable of consuming any of Carbs 1-7, it prefers 1, B prefers 3, etc.

Prebiotic Compositions

Prebiotic compositions are described herein. Such prebiotic compositions can be administered in a regimen that fosters the growth and/or activity of challenger and/or protagonist probiotic compositions.

A "prebiotic" includes one or more substances that, when ingested, is neither digested nor absorbed by the host (an animal or human), but is capable of stimulating the growth and/or the activity of bacteria of the intestinal flora, conferring benefits on health (Gibson G R, Roberfroid M B. Dietary modulation of the human colonic microbiota: introducing the concept of prebiotics. J Nutr. 1995 June; 125(6): 1401-12. PMID).

To date, attempts to positively impact the gut microbial community have mainly been based on trial and error. Product manufacturers and researchers have treated the gut microbiota community as a type of "black box," where a prebiotic may be administered with only a hopeful feeling that it may be beneficial. The compositions and methods described herein are designed to optimize the benefits of probiotic formulations by supplying one or more types of microbes that challenge other microorganisms to produce beneficial compounds or materials.

The challenger microbe can be present in the probiotic formulation and/or can be endogenously present in the subject receiving the probiotic formulation. The prebiotic compositions can foster the growth and/or metabolism of the challenger microbe and/or the microorganism that generates the beneficial compounds or materials.

The prebiotic compositions typically contain one or more types of carbohydrates that are not significantly digested in the saliva, stomach or small intestine. In particular, the prebiotic is intended to be digested or fermented in the large intestine, and should be resistant to digestion in the upper digestive tract. The prebiotic compositions can also contain one or more quorum sensing peptides.

Quorum sensing peptides are signaling molecules that in some instances can stimulate or respond to population. For example, bacteria can use quorum sensing to coordinate certain behaviors such as biofilm formation, virulence, and antibiotic resistance, based on the local density of the bacterial population. Quorum sensing can occur within a single bacterial species as well as between diverse species. A variety of different molecules can be used as signals. Common classes of signaling molecules are oligopeptides in Gram-positive bacteria, N-acyl homoserine lactones (AHL) in Gram-negative bacteria, and a family of autoinducers known as autoinducer-2 (AI-2) in both Gram-negative and Gram-positive bacteria. Any such quorum sensing peptides can be included in the prebiotic compositions.

The carbohydrates in the prebiotic compositions can contain two or more sugar (monosaccharide) residues. For example, the carbohydrates can contain three or more sugar (monosaccharide) residues, or four or more sugar (monosaccharide) residues, or five or more sugar (monosaccharide) residues.

A variety of different sugar residues can be included in the carbohydrates. For example, the sugar residues can include any of the isomers of triose, tetrose, pentose, hexose, heptose, or octose monosaccharides, as wells as combinations thereof. In some cases, the sugar residues can include any of the α or β anomeric forms and/or any of the keto-forms, aldo-forms, furanose forms, pyranose forms, and/or linear forms of monosaccharides such as glucose, fructose, galactose, mannose, sorbose, psicose, fucose, allose, altrose, idose, gulose, talose, ribose, ribulose, xylose, xylulose, deoxyglucose, deoxyfructose, deoxygalactose, deoxymannose/rhamnose, deoxysorbose, deoxypsicose, deoxyallose, deoxyaltrose, deoxyidose, deoxygulose, deoxytalose, deoxyribose, deoxyribulose, deoxyxyulose, tagatose, hemicellulosic fractions, and combinations thereof.

The monosaccharides or sugars can be linked together by alpha or beta linkages. For example, the monosaccharides or sugars can be linked together by 1,2-linkages, 1,3-linkages, 1,4-linkages, 1,5-linkages, 1,6-linkages, 2,3-linkages, 2,4-linkages, 2,5-linkages, 2,6-linkages, or combinations thereof.

The composition can include one or more fructo-oligosaccharides; beta-(2,6) oligofructan (levan); inulin; beta-(2,1) oligofructan; beta-1,2 terminated with glucose; beta-(1,3)-galactooligosaccharides; beta-(1-4)-galactooligosaccharides: beta-(1,6) galactooligosaccharides; beta-(1,4) xylooligosaccharides; hemicelluloses; arabinoxylan; guar gum; acacia gum; arabinogalactan, or combinations thereof.

However, the prebiotic compositions described herein are generally metabolized by microorganisms that reside in the large intestine. Hence, the carbohydrates in the prebiotic compositions include oligosaccharides that are structurally designed to resist significant digestion by carbohydrate cleaving enzymes in the saliva, stomach, and small intestine of animals. For example, the percentage of linkages that can be cleaved by animal digestive enzymes in the saliva, stomach and small intestine can be less than 40%, or less than 30%, or less than 20%, or less than 10%, of the total linkages between the monosaccharides of the carbohydrates.

Examples of enzymes that can be found in animal saliva, animal stomachs, and animal small intestines include amylase, maltase, lactase, lysozyme, and sucrase-isomaltase. Amylase hydrolyzes alpha 1,4-linkages between starches and dextrins. Maltase (also called alpha-glucosidase, gluco-invertase, glucosidosucrase, maltase-glucoamylase, alpha-glucopyranosidase, glucosidoinvertase, alpha-D-glucosidase, alpha-glucoside hydrolase, alpha-1,4-glucosidase. glucoamylase, and alpha-D-glucoside glucohydrolase) converts maltose to glucose by cleaving the alpha-(1,4) linkages between the two glucose subunits. Lactase (also known as lactase-phlorizin hydrolase) cleaves the beta-(1,4) linkage of lactose to generate glucose and galactose. Lysozyme hydrolyzes 1,4-beta-linkages between N-acetylmuramic acid and N-acetyl-D-glucosamine residues in a peptidoglycans. Sucrase-isomaltase is a digestive enzyme present in the intestine, in particular from the brush border of the small intestine. Dissacharidase, sucrase-isomaltase enzymes catalyze both the hydrolysis of the beta-(1,2) linkages of sucrose to yield fructose and glucose, and the hydrolysis of alpha-(1,6) linkages of oligosaccharides that are sufficiently small, in particular, isomaltose, isomaltotriose, and isomaltotetraose to yield glucose. The ability of this enzyme to catalyze the hydrolysis of isomaltooligosaccharides decreases with the increase of substrate molecular weight.

Hence, while the prebiotic carbohydrate may have a low number of alpha-1,4-linkages, most of the linkages in the prebiotic carbohydrate are not alpha-1,4-linkages.

For example, the prebiotic carbohydrates that are selected for inclusion in prebiotic compositions by the methods described herein can have structures like those shown in Formula I.

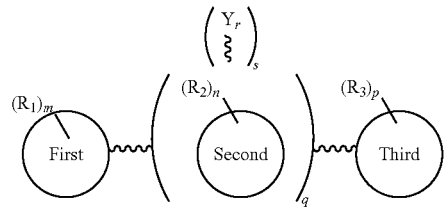

where:
each First, Second, and Third ring is separately a three-atom, four-atom, live-atom, or six-atom heterocyclic ring with one or two oxygen, sulfur, or nitrogen heteroatoms;
each Y is an optional monosaccharide or oligosaccharide with r monosaccharides, where each Y has a linkage ( ~~~ ) to a Second ring;
each ~~~ is separately a linkage between First, Second, and Third ring subunits, as well as linkages between each Y monosaccharide or Y oligosaccharide and a Second ring;
each m, n, and p is an integer separately selected from any of 2-5;
q is an integer selected from any of 1-100;
each r is an integer separately selected from 0-10;
s is an integer selected from 0-20; and
each $R_1$, $R_2$, and $R_3$ is separately selected from any of hydrogen, hydroxy, alkoxy, amino, carboxylate, aldehyde (CHO), phosphate or sulfate.

In some cases, one or more of the First, Second, or Third rings of Formula I is selected from a five-atom, or six-atom heterocyclic ring. In some cases, one or more of the First, Second, or Third rings of Formula I has an oxygen or nitrogen heteroatom. In some cases, one or more of the First, Second, or Third rings of Formula I has an oxygen heteroatom. In some cases, the Third ring can be a monosaccharide. For example, the Third ring can be a reducing monosaccharide. In some cases. the Third ring can be a glucose.

The linkages ( ~~~ ) between rings or monosaccharides of the carbohydrates of Formula I can be alpha or beta linkages. The linkages can be between different ring carbons of the such as 1,2-linkages, 1,3-linkages, 1,4-linkages, 1,5-linkages, 1,6-linkages, 2,1-linkages, 2,2-linkages, 2,3-linkages, 2,4-linkages. 2,5-linkages. 2,6-linkages, 3,1-linkages, 3-2, linkages, 3,3-linkages, or combinations thereof. However, the percentage of linkages in the carbohydrates of the prebiotic compositions that can be cleaved by animal digestive enzymes in the saliva, stomach and small intestine is less than 20%, or less than 10%, of the total linkages between the First ring, Second rings, Third rings and Y groups. For example, the percentage of linkages in the carbohydrates of the prebiotic compositions that are alpha-(1,4) linkages can be less than 20%, or less than 10% of the total linkages between the First ring, Second rings. Third rings and Y groups.

In some cases, each m, n, or p can be an integer separately selected from any of 3-5. For example, for some carbohydrates of Formula I or II, each m, n, or p can be an integer separately selected from any of 4-5.

In some cases, the q variable is an integer is selected from any of 1-20. In some cases, the q variable is an integer is selected from any of 1-15, or 1-10.

In various cases, the value of q is typically larger than s. For example, in some cases the variable q can be an integer of from 2 to 15, or of from 2 to 10, or of from 2 to 7. However, in some cases s can be an integer of from 1 to 5, or of from 1 to 3, or of from 1 to 2.

The r variable defines the number of monosaccharides in the optional Y monosaccharide or oligosaccharide. For example, in some cases, the r variable can vary from about 0 to 10, or from about 0 to 7, or from about 0 to 5, or from about 0 to 3, or from about 0 to 1.

In some cases, the prebiotic compositions include maltosyl-isomaltooligosaccharides (MIMOs). "Maltosyl-isomaltooligosaccharides," or MIMOs, or, by convention, "isomaltosyl-maltooligosaccharides" (IMOMs) refer to an oligosaccharide, an isomaltooligosaccharide glucan. In some cases, the MIMOs can have less than 40 degrees of polymerization, less than 30 degrees of polymerization, less than 20 degrees of polymerization, or less than 10 degrees of polymerization. MIMOs have a majority of α-(1-6) linkages but they can be terminated with an α-(1→4) linkage at the reducing-end (D-glucose). The α-(1→4) terminal group is comprised of maltose. Hence, a MIMO is called a maltosyl-isomaltooligosaccharide, or MIMO, as per IUPAC convention. MIMOS can be produced by an acceptor reaction with either maltose or other isomaltooligosaccharide. An example of an MIMO with a single maltosyl linkage [—O-α-(1,4)-] linkage at the reducing end is maltosyl-isomaltotriose has the following chemical structure:

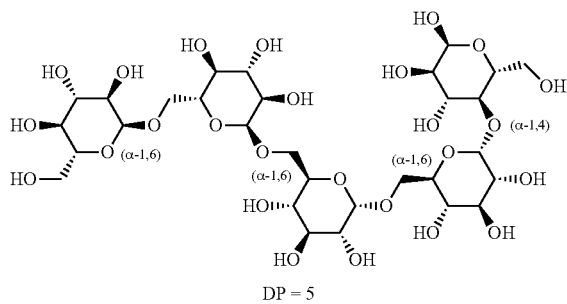 [SMILES: OC[C@H]1O[C@H](OC[C@H]2O[C@H](OC[C@H]3O[C@H](OC[C@H]4O[C@H](O[C@H]5[C@H](O)[C@@H](O)[C@@H](O)O[C@@H]5CO)[C@H](O)[C@@H](O)[C@@H]4O)[C@H](O)[C@@H](O)[C@@H]3O)[C@H](O)[C@@H](O)[C@@H]2O)[C@H](O)[C@@H](O)[C@@H]1O]

DP = 5

The prebiotic compositions can, for example, include maltosyl-isomaltooligosaccharides with a mass average molecular weight distribution of about 640 to 10,000 daltons. In some cases, the mas % s average molecular weight distribution of the maltosyl-isomaltooligosaccharides can be about 730 to 900 daltons. The maltosyl-isomaltooligosaccharides in the compositions can contain more α-(1-6) glucosyl linkages than α-(1,2), α-(1,3), or α-(1,4) glucose linkages. In general, maltosyl-isomaltooligosaccharides in the compositions can contain about one α-(1,4)-linkage, for example at the terminus of the oligosaccharide chain.

The prebiotic compositions can have some mannitol in them. For example, the compositions can have more than 3%/brix mannitol, or more than 4% %/brix mannitol, or more than 5% %/brix mannitol as detected by refractive HPAEC-PAD or HPLC-RID. For example, the amount of mannitol in the compositions can be less than 30%/brix mannitol, or less than 20%/brix mannitol, or less than 15%/brix mannitol or less than 12%/brix mannitol, or less than 10%/brix mannitol, or less than 9%/brix mannitol, or less than 8%/brix mannitol (e.g., 5-6%/brix) as detected by HPAEC-PAD or HPLC-RID.

When the compositions contain maltosyl-isomaltooligosaccharides there are generally no more than about 17 glucosyl units, or no more than about 16 glucosyl units, or no more than about 15 glucosyl units, or no more than about 14 glucosyl units, or no more than about 13 glucosyl units as detected by HPAEC-PAD or HPLC-RID.

In some cases, the compositions can have less than 2%/brix isomaltose, or less than 1%/brix isomaltose, or less than 0.5%/brix isomaltose, or less than 0.2%/brix isomaltose, or less than 0.1%/brix isomaltose as detected by HPAEC-PAD or HPLC-RID. In some cases, the compositions have no isomaltose, or levels below the detection limit (for example, as detected by HPAEC-PAD or HPLC-RID).

The compositions also can have less than 5%/brix glucose, or less than 4%/brix glucose, or less than 3%/brix glucose, or less than 2%/brix glucose, or less than 1%/brix glucose as detected by HPAEC-PAD or HPLC-RID.

The compositions also can have less than 5%/brix sucrose, or less than 4%/brix sucrose, or less than 3%/brix sucrose, or less than 2%/brix sucrose as detected by HPAEC-PAD or HPLC-RID.

The compositions also can have less than 4%/brix fructose, or less than 3%/brix fructose, or less than 2%/brix fructose, or less than 1%/brix fructose, or less than 0.5%/brix fructose, or less than 0.25%/brix fructose as detected by HPAEC-PAD or HPLC-RID.

The compositions can contain small or non-detectable quantities of organic acids such as lactic acid, acetic acid or formic acid. For example, the compositions can have less than 16%/brix lactic acid, acetic acid and formic acid; less than 3%/brix lactic acid, acetic acid and formic acid; less than 2%/brix lactic acid, acetic acid and formic acid; or less than 1%/brix lactic acid, acetic acid, and formic acid; or less than 0.5%/brix lactic acid, acetic acid, and formic acid; or less than 0.2%/brix lactic acid, acetic acid, and formic acid; or less than 0.1%/brix lactic acid, acetic acid, and formic acid as detected by HPAEC-PAD or HPLC-RID. In some cases, the compositions can have no organic acids such as lactic acid, acetic acid or formic acid, as measured by HPAEC-PAD or HPLC-RID.

In some cases, the prebiotic compositions can be any of those described in U.S. Ser. No. 62/280,026 filed Jan. 18, 2016, which is incorporated herein by reference in its entirety.

The prebiotic compositions can also include plant dietary polysaccharide, including soluble polysaccharides, such as soluble hemicelluloses and celluloses that some types of microorganisms can metabolize. The breakdown products of such plant polysaccharides often feed beneficial microorganisms. For example, *B. thetaiotaomicron* can process some plant polysaccharides to provide products that foster *E. rectale* synthesis of butyrate.

In some cases, the prebiotic compositions can be designed for the individual needs of a subject. Assay methods are also described herein for identifying individualized prebiotic compositions that can optimally balance the probiotic microorganism mixture within subjects. In some cases, prebiotic compositions are provided for populations of subjects that all have similar health issues (e.g., vegetarians/vegans who may have vitamin B12 deficiencies, subjects with cancerous or precancerous conditions, or subjects with irritable bowel syndrome).

TABLE 5

Examples of Prebiotic Compositions
to Foster Protagonist Microorganism Growth and Activity

| Prebiotic | Protagonist (Beneficial) Probiotic Bacteria | Bacteriocin | Cell line to attack | Demonstration of Stressed versus non-stressed |
|---|---|---|---|---|
| ISOThrive ™ | Lactococcus lactis subsp. lactis NRRL B-1821 | Class I; Nisin A | MCF7, HepG2, HCT-15, DLD-1, HSC-3, and 14A. | Dose dependent response evident with head and neck cell line HSC-3; induction noted in 14A, Effect of base broth evident on HCT-15 and DLD-1 colon cancer lines. Organism antagonized via Weissella viridescens NRRL B-1951 demonstrated activity significantly higher than the Base broth. |
| ISOThrive ™ | Lactobacillus gasseri ATCC 4962 | Class V; Gassericin A (putative) | HCT-15, DLD-1, HSC-3, and 14A. | Dose dependent response of base broth noted against head and neck cell line HSC-3; induction noted in 14A. More effective than unchallenged broth containing nisin A. Effect of base broth evident on HCT-15 and DLD-1 colon cancer lines. |
| ISOThrive ™ | Lactobacillus plantarum NRRL B-4496 | Class II; Plantaricin A (putative) | Jurkat, GH4, Reh (Kaur et al), suggest MDST 8 and HCA-2. | Base broth had no significant effect on either HSC-3 or 14A cell lines. Effect of broth via antagonist |
| α-GOS (alpha-galacto-oligo-saccharides, e.g., Olygose ™) | Pediococcus acidilactici NRRL B-5627 | Class IIa; pediocin PA-1 (putative) | A-549, HCT-15, DLD-1, HSC-3, and 14A. | Fermentation of base broth and antagonist Lactobacillus sakei DSM 20017 (ATCC 15521). |
| XOS (xylooligo-saccharides, e.g., PreticX ™); scFOS (short-chain fructooligo-saccharides)/ Inulin (fructan poly-saccharides), Prebiotin ™ (oligo-fructose- | Pediococcus pentosaceus ATCC 43200 | Class IIa; pediocin A (putative) | HCT-15, DLD-1, MCF7, HeLa, HepG2, HSC-3, and 14A. | Fermentation of base broth and antagonist lactobacillus helveticus ATCC 15009. |

TABLE 5-continued

Examples of Prebiotic Compositions
to Foster Protagonist Microorganism Growth and Activity

| Prebiotic | Protagonist (Beneficial) Probiotic Bacteria | Bacteriocin | Cell line to attack | Demonstration of Stressed versus non-stressed |
|---|---|---|---|---|
| enriched-Inulin) ISOThrive ™; scFOS, Advanta-FOS ™ | *Lactobacillus plantarum* LD1 | Class I, IIa, nisin A and plantaricin LD1. | HCT-15, DLD-1, HSC-3, and 14A | Fermentation of base broth and antagonist *Lactococcus lactis* subsp. *lactis* NRRL B-1821. |
| ISOThrive ™ | *Lactococcus lactis* subsp. *lactis* biovar diacetylactis UL 719 | Class I, nisin Z and (putative) pediocin PA-1 | HCT-15, DLD-1, HSC-3, and 14A | Fermentation of base broth and antagonist *Pediococcus acidilactici* UL5 are pending. |

*Hoseinifar et al., Effects of galactooligosaccharide and *Pediococcus acidilactici* on antioxidant defense and disease resistance of rainbow trout, *Oncorhynchus mykiss*, Annals Animal Sci (2016) DOI: 10.1515/aoas-2016-0024

Key to Cell Lines:
MCF7:Named for Frances Mallon (1970), breast cancer, invasive breast ductal carcinoma.
HepG2: Human liver cancer, 15 a Caucasian male, well differentiated hepatocellular carcinoma.
HCT-15: Human colonic epithelium, adherent, Dukes' type C colorectal cancer (male).
DLD-1: Human colonic epithelium, adherent, Dukes' type C colorectal cancer (adult male); differentiated from HCT-15 because they originate from totally different chromosomal aberrations within the same parent cell line.
HSC-3: Human oral squamous cell carcinoma.
14A:UM-SCC-14A, genotyped University of Michigan 2010; oral cavity squamous cell carcinoma. See website at www.ncbi.nlm.nih.gov/pmc/articles/PMC3292176/.
Jurkat: T-cell leukemia, human 2003, acute T cell leukemia.
GH4: Pituitary epithelial tumor, growth hormone secreting, rat,
Reh: Human acute lymphocytic leukemia (non T; non B).
MDST8: human colon carcinoma.
HCA-2: Human sigmoid colon adenocarcinoma.

Administration Regimens

The probiotic compositions can be administered on a regimen that benefits the health of the subject to which they are administered. For example, as described above, the probiotic compositions can be administered every day, or every two days, or every three days, or twice per week, or once per week, or once per two weeks, or once per month, or combinations thereof. For example, dosages of the probiotic composition containing about $10^6$-$10^{11}$ CFU microbes/microorganisms can be administered. In some cases, probiotic composition containing about $10^7$-$10^{11}$ CPU microbes/microorganisms can be administered.

Probiotic compositions can contain challenger and protagonist microorganisms. However, in some cases, the probiotic compositions can contain challenger microbes without protagonist microorganisms. Instead, the subject may either already have protagonist microorganisms in his or her gut, or the subject may benefit from separate administration of protagonist probiotic compositions. Alternatively, the subject may already have challenger microorganisms in his or her gut and may not need administration of a challenger probiotic composition, but the subject may benefit from administration of protagonist probiotic compositions. Hence, the challenger microbes can be provided and/or administered in one probiotic composition while the protagonist microorganisms can be provided and/or administered in a separate probiotic composition. One or the other of the challenger or protagonist compositions may not be administered for some period of time and then administration of one or the other of the challenger or protagonist compositions may then be initiated or resumed.

Challenger and protagonist probiotic compositions can therefore be administered together or separately on the same or on different administration regimens. For example, a protagonist probiotic composition can be administered every day, or every two days, or every three days, or twice per week, or once per week, or once per two weeks, or once per month, or combinations thereof; while a challenger probiotic composition can be administered on the same days as the protagonist probiotic composition, or on days when the protagonist probiotic composition is not administered. Thus, the challenger probiotic composition can also be administered every day, or every two days, or every three days, or twice per week, or once per week, or once per two weeks, or once per month, or combinations thereof. However, the timing of administration of the challenger probiotic composition can be different from that of the protagonist probiotic compositions.

The challenger and protagonist probiotic compositions can be administered in different amounts such that the amounts of challenger microbes and/or protagonist microorganisms in the probiotic composition can vary. For example, amounts of challenger microbes and/or protagonist microorganisms in the probiotic composition can vary from about $10^6$ to about $10^{13}$ CFU microbes/microorganisms, or from about $10^7$ to about $10^{12}$ CFU microbes/microorganisms, or from about $10^8$ to about $10^{12}$ CFU microbes/microorganisms, or from about $10^9$ to about $10^{12}$ CFU microbes/microorganisms, or from about $10^6$ to about $10^{11}$ CFU microbes/microorganisms, or from about $10^6$ to about $10^{10}$ CFU microbes/microorganisms, or from about $10^6$ to about $10^9$ CFU microbes/microorganisms. In some cases, probiotic composition can contain about $10^9$-$10^{11}$ CFU microbes/microorganisms.

Definitions

The term "about" as used herein is intended to reflect a variation of 10% of the value it is attached to. For example, a concentration of "about 20%" is reflective of a concentration ranging from 18% to 22%. As another example, a quantity of "about $10^8$" is reflective of a range of $0.9\times10^8$ to $1.1\times10^8$. In some cases the term "about" as used herein is intended to reflect a variation of 5% of the value it is attached to.

As used herein, the terms "subject" or "patient" refers to any animal, such as a domesticated animal, a zoo animal, or a human. The "subject" or "patient" can be an animal such as a dog, cat, bird, poultry, livestock, zoo animal, endangered species animal, or a human. Specific non-limiting examples of livestock that can be tested and/or treated as described herein include cattle, dairy cows, pigs. sheep, goats, horses, mules, donkeys, asses, buffalo, rabbits, chickens, turkeys, ducks, geese, Cornish game hens, guinea fowl, squabs, pigeons, and the like. Experimental animals can also be tested and/or treated as described herein. For example, such experimental animals can include rats, mice, guinea pigs, and any of the other animals listed above. Hence, the subject or patient can be any mammal, avian animal, or other creature.

Manufacturing of Beneficial Compounds/Materials

As illustrated herein, significantly greater amounts of beneficial compounds such as nisin are generated when a challenger microbe is present in the incubation mixture with one or more protagonist microorganism(s). Hence, a method is provided herein for improving the manufacture of a product that involves incubation of a substrate for the product, a manufacturing microorganism (e.g., a protagonist microorganism) that can manufacture the product, and a challenger microbe that stimulates the manufacturing microorganism to manufacture more product than when the challenger microbe is not present.

For such manufacturing methods, the challenger microbe typically does not manufacture the product. Instead, the challenger microbe stimulates the manufacturing microorganism (e.g., a protagonist microorganism) to manufacture the product.

The substrate, manufacturing microorganism, and challenger microbe can be incubated together in a culture medium. The culture medium can be any convenient cell culture medium. Examples of culture media that can be employed include De-Man, Rogosa and Sharpe (MRS) media (available from Difco). LB liquid media, M17 medium (available from Sigma). For bacteria, the media in some cases can contain peptone, lactose and yeast extract.

In some cases the media for *Lactococcus lactis* (e.g., challenged with a *Weissella viridescens*) can include peptone (meat. Sigma). bacteriological yeast extract (Marcor), maltosyl-isomaltooligosaccharides (MIMOs)J, $MnSO_4$—$H_2O$ (J. T. Baker), $MgSO_4$ (Amresco), $FeSO_4$.$7H_2O$ (Amresco), $KH_2PO_4$ (Alfa Aesar), NaCl (BDH), and $CaCl_2$-$2H_2O$ (Alfa Aesar).

When the manufacturing microorganism is yeast, the yeast cells may be grown in any convenient medium used for yeast. In some cases the yeast are cultured or fermented in a rich media, YPD media, or minimum media conventionally used in the field. YPD medium contains about 1% yeast extract, 2% peptone and 2% dextrose. Yeast minimum media typically contains 0.67% of yeast nitrogen base ("YNB") without amino acids supplemented with appropriate amino acids or purine or pyrimidine bases. An amount of sugar, typically 2% unless otherwise indicated, may be used as carbon source, including glucose (dextrose), galactose, maltose or L-arabinose, among others.

In some cases, the incubation is performed in a fermentation apparatus.

The ratio of manufacturing microorganism (e.g., a protagonist microorganism) to the challenger microbe in the incubation can vary. In some cases, the ratio of manufacturing microorganism (e.g., a protagonist microorganism) to the challenger microbe in the incubation can be:

about 10 manufacturing microorganisms: 1 challenger microbe; or about 50 manufacturing microorganisms: 1 challenger microbe: or about 100 manufacturing microorganisms: 1 challenger microbe; or about 1000 manufacturing microorganisms: 1 challenger microbe; or about 10 manufacturing microorganisms: 2 challenger microbes; or about 10 manufacturing microorganisms: 3 challenger microbes; or about 10 manufacturing microorganisms: 4 challenger microbes; or about 10 manufacturing microorganisms: 5 challenger microbes; or about 10 manufacturing microorganisms: 6 challenger microbes: or about 10 manufacturing microorganisms: 7 challenger microbes; or about 10 manufacturing microorganisms: 8 challenger microbes; or about 10 manufacturing microorganisms: 9 challenger microbes; or about 1 manufacturing microorganism: 1 challenger microbe; or about 1 manufacturing microorganism: 2 challenger microbes.

The number of manufacturing microorganisms and challenger microbes can be estimated from the cell density of an inoculate microorganism measured, for example, by the absorbance of a cell suspension at 600 nm, or by determining the colony forming units (cfu)). In some cases the amounts of manufacturing microorganisms and challenger microbes can be estimated roughly, for example, by generating log-phase cultures of manufacturing microorganisms and challenger microbes, and then simply adding the weight: weight ratio of manufacturing microorganisms to challenger microbes to the culture medium.

In some cases. the challenger microbe(s) can be added as an inoculum of late-log challenger microbes at about 1-2% of the protagonist broth, or about 1.3% of the protagonist broth volume. In some cases, the challenger microbe(s) can be added to a late log-phase protagonist culture.

The manufacturing microorganisms with or without the challenger microbes can be incubated for various times and under various conditions. For example, the manufacturing microorganisms with or without the challenger microbes can be incubated for at least 6 hours, or at least 8 hours, or at least 10 hours, or at least 12 hours, or at least 14 hours, or at least 16 hours, or at least 20 hours, or at least 24 hours, or at least 48 hours. In some cases, the incubation can be continuous, with fresh nutrients added periodically and product removed at various intervals. In other cases, broths can be recycled over immobilized cell cultures with or without added nutrients to improve yields.

The temperature of incubation can vary with the types of microorganisms incubated. For example, yeast cells can in some cases be incubated at somewhat lower temperatures than bacteria. Examples of temperatures for incubation of the microorganisms (with or without the challenger microbes) can include temperature ranges of about 15° C. to about 45° C., or about 20° C. to about 42° C., or about 22° C. to about 40° C., or about 25° C. to about 37° C. In some cases, *Lactococcus lactis* can be incubated with *Weissella viridescens* at a temperature of about 35° C. to about 37° C.

In some cases, good results can be obtained by incubating a protagonist microorganism (e.g., *Lactococcus lactis*) for 24 hour in a media with a defined carbon source (e.g., MIMOs such as IsoThrive™, which is useful for *Lactococcus lactis*). The protagonist microorganisms generally will deplete the media after about 24 hours of incubation. At that time, the media can be replenished with additional carbon source (e.g., MIMOs such as IsoThrive™) to stimulate growth for another 2-4 hours.

At this time the protagonist microorganism are typically in log phase. An inoculum of log phase challenger microbes (e.g., *Weissella viridescens*) can be added to the log phase protagonist microorganism (e.g., *Lactococcus lactis*). The combined protagonist/challenger mixture can then be incubated for another day or so. for example, for about 48 hours. Such a process can stimulate production of a desirable product, such as one or more types of nisin, by at least 2-fold, or at least 3-fold, or at least 5-fold, or at least 7-fold, or at least 10-fold. For example, in experiments with *Lactococcus lactis* as a protagonist microorganism, at least 5-fold more nisin was produced when the challenger microbe, *Weissella viridescens*, was present than when this challenger microbe was not present.

In some cases, the protagonist microorganisms can be immobilized, for example, in a column to facilitate production of useful products. Selected media can be circulated or recycled through the column, where the media can have a carbon source such as particular carbohydrates (e.g., MIMOs) that support the growth of the protagonist microorganisms. When recycling the media, components of the media (e.g., the carbon source) can be replenished periodically. The challenger microbes can be added to the column of immobilized protagonists to stimulate production of the desired product. Alternatively, the challenger microbes can be immobilized in a second column and then the media from incubation of the challenger microbes, or some portion of the challenger microbes can be circulated through the first column containing the immobilized protagonist microorganism. The desired product can be removed from the recycling media either continuously or periodically. In this manner, the production of desirable products can be automated.

Figure 12A:
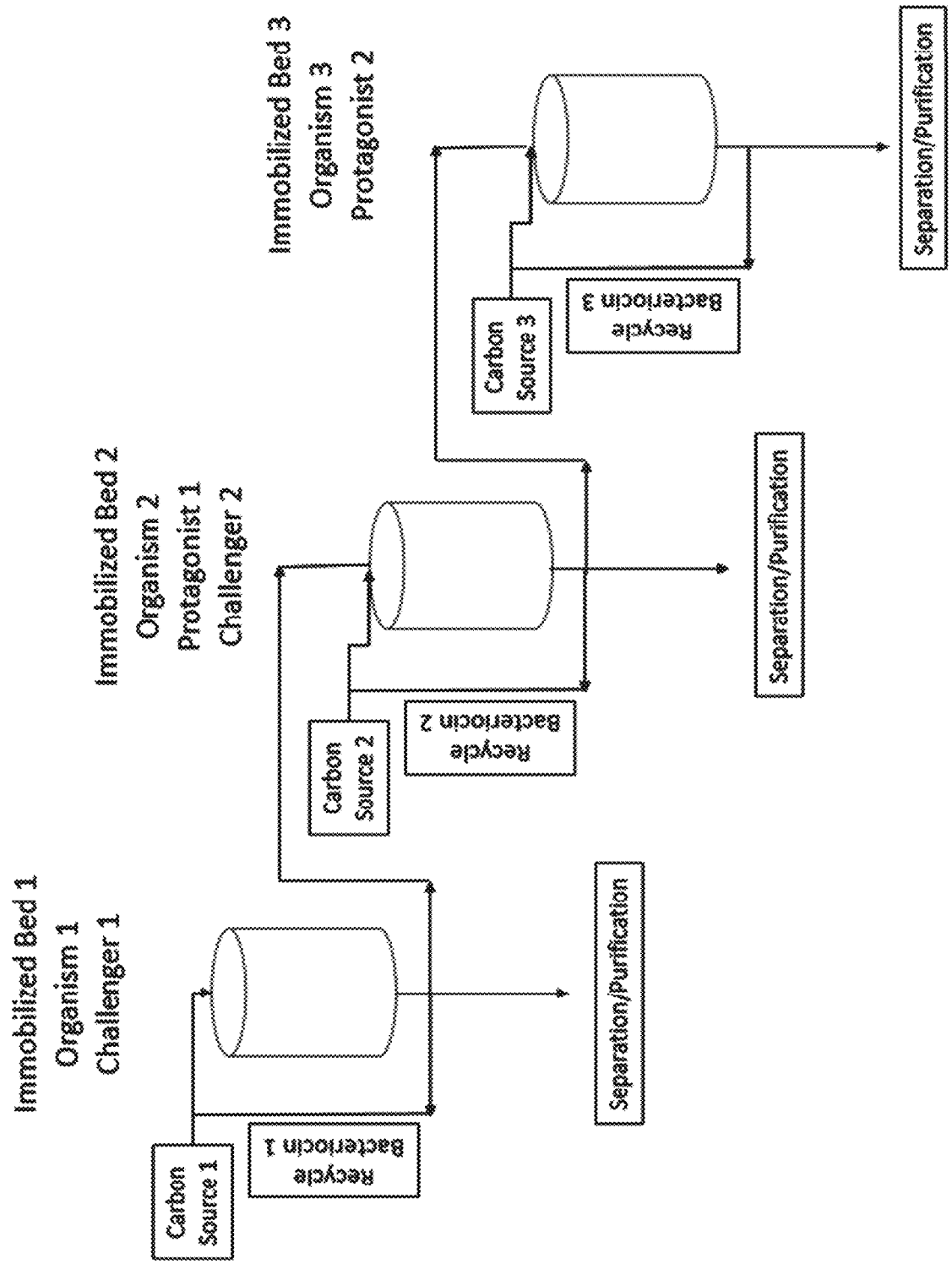
FIGS. 12A-12B illustrate methods for manufacturing and isolation of various beneficial compounds and/or materials (e.g., bacteriocins) made by protagonist microorganisms, for example, when challenged by challenger microbes.
Figure 12B:
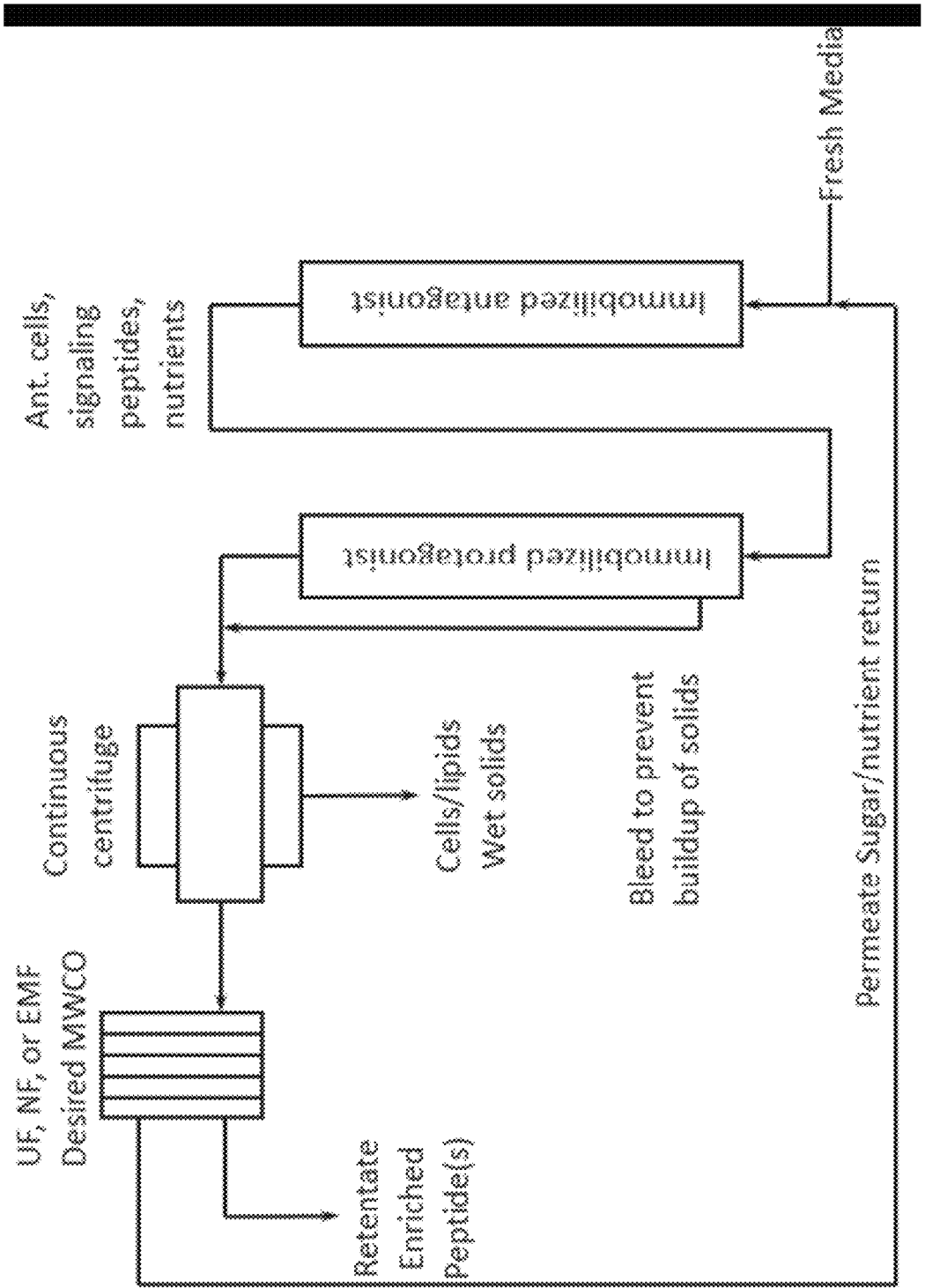

Another embodiment could include a carbon source that is preferable for the protagonist growth or production of a targeted bacteriocin and a different carbon source that is preferable for the challenger growth or production of a second targeted bacteriocin. The output of the challenger bacteriocin-immobilized column, or a portion thereof, could be added as input to a protagonist immobilized bed so as to induce increased production of the protagonist bacteriocin. The output, or a portion thereof, of the protagonist bed could be recycled to increase the overall concentration of protagonist bacteriocin prior to separation and purification of a product such as a bacteriocin. In this way two or more different and primarily separated streams of bacteriocins can be produced. It is also possible to construct numerous (e.g., an infinite number of) cascades of immobilized beds containing alternating beds of challenger organisms and protagonist organisms wherein in one instance at least one first organism plays the role of a challenger organism for at least one second organism, where the at least one second organism simultaneously plays the role of protagonist for the at least one first organism, while also playing the role of challenger organism to a third organism, etc. (see FIG. 12).

Other convenient ways of immobilizing the microbes can also be employed. For example, one or the other of the protagonist microorganisms or the challenger microbes can be immobilized on beads, on magnetic particles, on a substrate, on a column matrix, or other convenient material.

Products generated by the methods can optionally be purified by methods available to those of skill in the art. If making two products (e.g., bacteriocins), products of different sizes, chemical properties, or physical products can be selected for production by various protagonist and challenger organisms to facilitate isolation of both products by size, or by use of the difference in the chemical properties or physical products. Contaminants of the desired product so produced can be removed by convenient procedures available to those of skill in the art.

For example, beneficial compounds and/or materials such as lantibiotics (which are positively charged) can be purified by a variety of techniques. Precipitation from the whole fermentation broth (e.g., *L. lactis* subsp. *lactis* broth after or during challenge) with low percentages of ammonium sulfate can remove some of the larger proteins (smaller peptides tend to remain in solution at low ammonium sulfate concentrations). Ammonium sulfate at 70% concentration can precipitate some useful compounds such as lantibiotics. Salts can be removed by use of membranes (e.g. Amicon) and/or size exclusion column gel chromatography matrices with an appropriate target molecular weight cutoff (MWCO). For example, the precipitate from the ammonium sulfate precipitation step can be passed through a filter, dialysis bag, or gel filtration column that excludes all but less than 5 kDa molecules and salts. For example, nisin A has a molecular weight of about 3.354 kDa. A filter or dialysis bag could be used in some cases that would allow lower molecular weight salts to pass through and be washed away but that would capture all molecules with a molecular weight greater than about 3 kDa. In some cases, a gel filtration column could be used for de-salting molecules such as nisin A where the gel filtration column allows small molecular weight salts to enter the column matrix while excluding the molecules with a molecular weight greater than about 3 kDa. Hence, the nisin A would elute before the salts. In a variety of cases, the desired lantibiotics can be washed extensively with water or buffer to desalinate them after ammonium sulfate precipitation.

The fermentation broth or semi-purified, de-salted ammonium sulfate precipitate containing the useful compound(s) (e.g., lantibiotics) can be passed through cationic ion exchange resins that can bind and thereby remove negatively charged compounds and proteins. Similarly, the fermentation broth or semi-purified, de-salted ammonium sulfate precipitate containing the useful compound(s) (e.g., lantibiotics) can be passed through anionic ion exchange resins that can bind positively charged compounds and proteins. When purifying a positively charged compound or peptide such as a lantibiotic, the compound or peptide would typically pass through a cation exchange column but such a positively charged compound or peptide would typically be bound to an anionic ion exchange matrix using a low salt buffer. An anionic ion exchange matrix can be washed with the low salt buffer to remove impurities, and then then desired positively charged compound or peptide can be eluted from the anionic ion exchange matrix using a high salt buffer, or by using a step-wise gradient or a continuous gradient of salt-containing buffers.

The resulting mixture can be purified via chromatographic fractionation, for example, via C18 high pressure liquid chromatography (HPLC), hydrophilic interaction liquid chromatography (HILIC), and/or other purification processes.

Purified fraction can be lyophilized and characterized by use of MALDI-MS, LC-MS/MS, NMR, and/or fluorescent monoclonal antibodies. The activity (e.g., antibacterial, antiproliferative, and/or anti-cancer activity) can be evaluated by methods available to those of skill in the art compared to known susceptible and/or not susceptible (control) type of organism or cell.

Direct Treatment with Beneficial Compounds or Materials

While it is possible, and often desirable to encourage the production of desired compounds and materials (e.g., bacteriocins) in situ or in vivo within a subject by protagonist bacteria, there may be other circumstances where it may be more desirable, or quicker to directly administer desirable compounds and materials such as bacteriocins to a subject. For example, while it is possible, and often desirable to encourage the production of bacteriocins in vivo, there may be circumstances where imminent risk to a subject can be mitigated by acting more quickly through direct administration of desirable compounds and materials such as bacteriocins. Administration of desirable compounds and materials can be profilactic (e.g., to prevent a condition or disease) or it can be after a disease or condition is ongoing (e.g., after other treatments have not been optimally successful).

For example, for the treatment of early or advanced stages of colon cancer, it may be desirable to directly administer the bacteriocin(s), such as nisin or gassericin, or a cocktail of nisin and gassericin, with or without other compounds and materials, directly to the diseased tissues via various methods including ingestion, enema, suppository, tampon, or via catheter. For example, any of these methods can be employed for bladder cancer. For vaginal or cervical cancers administration can include, for example, ingestion, tampon, or douche. Cocktails could be formulated to include the desired bacteriocin(s) with appropriate carriers at a selected pH, so as to be compatible with the normal cells while inhibiting the targeted cells or tissues. In an example of advanced colon cancer, a mixture of beneficial compounds or materials such as bacteriocins could be administered via enema, allowed to remain in situ for about 1 minute or up to 5 minutes, or up to 10 minutes, or up to 20 minutes, or up to 60 minutes, etc. The treatment could be administered daily, or every two days, or every three days, or every week, or every other week, etc., until the proliferation of cancerous cells had been substantially reduced or rendered undetectable.

Before, during, or after such treatment a targeted cocktail of probiotics and/or prebiotics can be administered at selected intervals with or without a targeted challenger organism(s) to induce the production of protective bacteriocins, for example, to reduce the risk of cancer recurrence or to prophylactically prevent cancer or other diseases. The targeted cocktail could include just probiotics containing protagonist microorganisms, challenger microbes, or combinations thereof. In some cases the targeted cocktail could include probiotic microorganisms/microbes as well as prebiotics that can stimulate the growth and/or metabolism of protagonist microorganisms or challenger microbes. In some cases, the targeted cocktail could include just prebiotics that can stimulate the growth and/or metabolism of protagonist microorganisms or challenger microbes.

Cocktails of beneficial compounds and/or materials can be made and administered for treatment of a variety of diseases. For example, the cocktails can be designed and administered for treatment of diseases such as cancers (e.g., bladder, oral, nasal, esophageal, cervical, and vaginal cancers), diarrhea, bacterial infections (food poisoning, gastroenteritis, Clostridium difficile infections, Salmonella infections, Shigella infections, E. coli infections, Campylobacter infections. Helicobacter pylori infections, Staphylococcus aureus infections, Yersinia enterocolitica infections, kidney infections, urinary tract infections, and the like), viral infections (viral gastroenteritis, rotavirus infections, Cytomegalovirus infections, and the like), fungal infections (e.g., yeast and/or dermatophyte infections), or combinations thereof.

The cocktails and methods can treat a variety of cancers such as head and neck squamous cell carcinomas (HNSCC), leukemia, oral squamous cell carcinoma, mouth cancer, head cancer, neck cancer, stomach cancer, colon cancer, bladder cancer, cervical cancer, or esophageal cancer. Other examples of cancers that can be treated by the methods include adenocarcinoma, carcinoma, breast cancer, cervical cancer, colon cancer, chondrosarcoma, dysplasia, fibrosarcoma, glioma, hepatoma, hyperplasia, leukemia, lymphoma, lung cancer, melanoma, myeloblastic, neuroblastoma, pancreatic cancer, prostate cancer, ovarian cancer, renal cell carcinoma, retinoblastoma, sarcoma, testicular cancer, uterine cancer. adenocarcinoma (e.g., colorectal adenocarcinoma), angiosarcoma, astrocytoma, basal cell carcinoma, bladder carcinoma, breast cancer, cervical cancer, colon carcinoma, chondrosarcoma, chronic lymphocytic leukemia, chronic myelocytic (granulocytic) leukemia, endotheliosarcoma, epithelial carcinoma, dysplasia, erythroleukemia. Ewing's tumor, fibrosarcoma, glioma, hepatoma, Hodgkin's lymphoma. hyperplasia, liposarcoma, leukemia, lymphoma, lung carcinoma, monocytic, melanoma, myeloblastic, myelomonocytic, myxosarcoma, neuroblastoma, non-Hodgkin's lymphoma, oligodendroglioma, pancreatic cancer, promyelocytic, prostate cancer, osteogenic sarcoma, ovarian cancer, renal cell carcinoma, retinoblastoma, small cell lung carcinoma, squamous cell carcinoma, testicular tumor, uterine cancer, Wilms' tumor, or a combination thereof.

A specific bacteriocin cocktail can, for example, be made by performing one or more of the following steps: (a) obtaining a sample (e.g., a biopsy, a stool sample, a urine sample, a cervical cell sample) from a subject, (b) optionally growing cells or viruses from the sample in vitro, (c) identifying the type of cells or virus in the sample (e.g., by sequence analysis, detection of cell type specific markers, observation of culture growth properties, and/or other methods), (d) assaying to obtain $IC_{50}$ values for various beneficial compounds or materials (e.g., bacteriocins) for inhibition of the type cells in the sample, (e) determine which is/are the most effective compounds or materials (e.g., bacteriocins) to inhibit the cells or viruses in the sample. (f) create a selected cocktail of one or more of the most effective compounds or materials (e.g., bacteriocins) at desired (e.g., the obtained IC50) concentrations, (g) when more than one of the most effective compounds or materials (e.g., bacteriocins) are in the selected cocktail, the selected cocktail can optionally be tested in vitro by culturing the selected cocktail with cells or viruses obtained from the subject, and determining the IC50 value of the selected cocktail mixture for inhibition of the cells or viruses (and, e.g., to thereby verify that the selected cocktail is at least as effective as the individual compounds or bacteriocins), (h) administer a cocktail of one or more of the effective compounds or material (e.g., bacteriocins) to the subject.

In the case of colon cancer, the administration can be via enema. In the event that a selected cocktail has previously been shown to be effective against a specific type of disease, the IC50 assays need not be performed again and the already tested selected cocktail may be administered after evaluation of the sample has identified the type of cells or virus that may be the causal agent of the disease.

The selected cocktail can be combined with one or more of various types of chemotherapeutic agents, for example, any of the chemotherapeutic agents described herein.

In some cases, the selected cocktail can be administered at the same time as one or more chemotherapeutic agent or the administration of the selected cocktail can be at different intervals of time than the one or more chemotherapeutic agents. For example, the administration of the selected cocktail and the chemotherapeutic agent can be done separately or together, depending on which is better tolerated by the patient.

As described herein, a challenger microbe can stimulate a protagonist microorganism to make greater amounts of useful compounds such as nisin than when the challenger microbe is not present. Useful compounds such as nisin are effective anti-proliferative and anti-cancer agents. In addition, as also illustrated herein, certain types of protagonist bacteria (e.g., Lactococcus lactis) can manufacture nisin amounts sufficient to kill or inhibit the growth of bacterial and cancer cells.

Methods are described herein that treat diseases such as cancer and microbial infections. The methods can involve administering to a subject a probiotic composition comprising a microorganism that can synthesize beneficial compounds and/or materials. Examples of beneficial compounds and/or materials that can synthesized by microorganisms include but are not limited to lantibiotics, bacteriocins, antibacterial compounds, anti-proliferative agents, anti-cancer agents, nutrients, vitamins, short chain fatty acids (SCFAs), hydrogen peroxide, neuromodulators, neurotransmitters (e.g, gamma-aminobutyric acid (GABA), serotonin, etc.), co-factors (e.g., NAD, cAMP, etc.), and combinations thereof. For example, microorganisms that can synthesize a bacteriocin such as nisin that can inhibit cancer cell and bacterial cell growth, include Lactococcus lactis.

A method is described herein that includes administering a challenger microbe, either in the probiotic composition with the (e.g., protagonist) microorganism that can synthesize nisin, or in a separate probiotic composition that includes the challenger microbe. Hence, the microorganism that can synthesize beneficial compounds and/or materials can be administered with the challenger microbe, without the challenger microbe, or the two can be administered at different times.

In some cases, the challenger microbe that can stimulate Lactococcus lactis to synthesize greater amounts of nisin can be Weissella viridescens.

For example, a challenger microbe can stimulate a microorganism (e.g., a protagonist microorganism) to make at least 2-fold, or at least 3-fold, or at least 4-fold, or at least 5-fold, or at least 6-fold, or at least 7-fold, or at least 8-fold, or at least 9-fold, or at least 10-fold more product than manufactured when the microorganism is cultured under the same conditions but without the challenger microbe.

Note that the methods described herein can provide localized delivery of beneficial compounds and materials to the gastrointestinal tract, including the colon, bladder, vagina, mouth, nasal cavities, esophagus, and/or stomach. The methods may be particularly effective for treatment of gastrointestinal diseases such as gastrointestinal cancers. For example, as illustrated herein, methods of producing beneficial compounds such as nisin can kill or inhibit the growth of colon cancer cells.

Compositions of Beneficial Compounds and Materials

The beneficial compounds and/or materials can be formulated as compositions with or without additional therapeutic agents, and administered to a subject such as an animal or a human patient, in a variety of forms adapted to the chosen route of administration. Routes for administration include, for example, local, oral, intra-intestinal (e.g., via enema), intra-bladder (e.g., via catheter into the bladder), intravaginal, dermal. parenteral, intraperitoneal, intravenous, and intraarterial routes.

The compositions can include beneficial compounds and/or materials that include but are not limited to lantibiotics, bacteriocins, antibacterial compounds, anti-proliferative agents, anti-cancer agents, nutrients, vitamins, short chain fatty acids (SCFAs), hydrogen peroxide. neuromodulators, neurotransmitters (e.g. gamma-aminobutyric acid (GABA), serotonin, etc.), co-factors (e.g., NAD, cAMP, etc.), and combinations thereof. In some cases, the beneficial compounds and/or materials include lantibiotics or bacteriocins. For example, as illustrated herein, larger amounts of bacteriocins such as nisins can be made by protagonist microorganisms when in the presence of challenger microbes than when no such challenger microbes are present. Such production methods facilitate manufacture of large amounts of useful bacteriocins, and illustrate that the presence of challenger microbes can stimulate protagonist microorganisms to make industrially useful amounts of other beneficial compounds and/or materials.

The compositions containing beneficial compounds and/or materials can be formulated as pharmaceutical dosage forms. Such pharmaceutical dosage forms can include (a) liquid solutions; (b) tablets, sachets, or capsules containing liquids, solids, granules, or gelatin; (c) suspensions in an appropriate liquid or paste; and (d) suitable emulsions.

Solutions of the active agents (beneficial compounds and/or materials, and optional other therapeutic agents) can be prepared in water or saline, and optionally mixed with other agents. For example, formulations for local administration may include sterile aqueous solutions that may also contain buffers, diluents, stabilizing agents, nontoxic surfactants, chelating agents, polymers, and/or other suitable additives. Sterile injectable solutions are prepared by incorporating the active agents in the required amount in the appropriate solvent with various other ingredients, in a sterile manner or followed by sterilization (e.g., filter sterilization) after assembly.

In another embodiment, beneficial compounds and materials can be prepared and incorporated into a broad range of lipid-containing dosage forms. For instance, the suspension containing beneficial compounds and materials can be formulated and administered as liposomes, gels, oils, emulsions, creams, pastes, ointments, lotions, foams, mousses, and the like.

In some embodiments, the active agents may be formulated in liposome compositions. In some sterile aqueous solutions, beneficial compounds and materials are adapted for administration by encapsulation in liposomes. Such liposomal formulations can include an effective amount of the liposomally packaged beneficial compounds and materials suspended in diluents such as water, saline, or PEG 400.

The liposomes may be unilamellar or multilamellar and are formed of constituents selected from phosphatidylcholine, dipalmitoylphosphatidylcholine. cholesterol, phosphatidylethanolamine, phosphatidylserine, dimyristoylphosphatidylcholine and combinations thereof. The multilamellar liposomes comprise multilamellar vesicles of similar composition to unilamellar vesicles. but are prepared so as to result in a plurality of compartments in which the silver component in solution or emulsion is entrapped. Additionally, other adjuvants and modifiers may be included in the liposomal formulation such as polyethylene glycol, or other materials.

While a suitable formulation of liposome includes dipalmitoyl-phosphatidylcholine:cholesterol (1:1) it is understood by those skilled in the an that any number of liposome bilayer compositions can be used in the composition of the present invention. Liposomes may be prepared by a variety of known methods such as those disclosed in U.S. Pat. No. 4,235,871 and in RRC, Liposomes: A Practical Approach. IRL Press, Oxford, 1990, pages 33-101.

The liposomes containing the active agents may have modifications such as having non-polymer molecules bound to the exterior of the liposome such as haptens, enzymes, antibodies or antibody fragments, cytokines and hormones and other small proteins, polypeptides or non-protein molecules which confer a desired enzymatic or surface recognition feature to the liposome. Surface molecules that preferentially target the liposome to specific organs or cell types include for example antibodies which target the liposomes to cells bearing specific antigens. Techniques for coupling such molecules are available in the art (see for example U.S. Pat. No. 4,762,915 the disclosure of which is incorporated herein by reference). Alternatively, or in conjunction, one skilled in the art would understand that any number of lipids bearing a positive or negative net charge may be used to alter the surface charge or surface charge density of the liposome membrane. The liposomes can also incorporate thermal sensitive or pH sensitive lipids as a component of the lipid bilayer to provide controlled degradation of the lipid vesicle membrane.

Liposome formulations for use with beneficial compounds and materials may also be formulated as disclosed in WO 2005/105152 (the disclosure of which is incorporated herein in its entirety). Briefly, such formulations comprise phospholipids and steroids as the lipid component. These formulations help to target the molecules associated therewith to in vivo locations without the use of an antibody or other targeting molecule.

Antibody-conjugated liposomes, termed immunoliposomes, can be used to carry active agent(s) within their aqueous compartments. Compositions of active agent(s) provided within antibody labeled liposomes (immunoliposomes) can specifically target the active agent(s) to a particular cell or tissue type to elicit a localized effect. Methods for making of such immunoliposomal compositions are available, for example, in Selvam et al., Antiviral Res. 33(1):11-20 (1996) (the disclosure of which is incorporated herein in its entirety).

For example, immunoliposomes can specifically deliver beneficial compounds and materials to the cells possessing a unique antigenic marker recognized by the antibody portion of the immunoliposome. Immunoliposomes are ideal for the in vivo delivery of active agent(s) to target tissues due to simplicity of manufacture and cell-specific specificity.

Tumor-specific antibodies can be used in conjunction with the inhibitors or liposomes containing inhibitors. Other active agents can also be included in such liposomes. Antibodies such as anti-CD11b antibodies, anti-CD33 antibodies. anti-VEGF receptor antibodies, anti-alpha-fetoprotein (AFP) antibodies, anti-carcinoembryonic antigen (CEA) antibodies, anti-CA 19-9 antibodies, anti-CA-125 antibodies, anti-MSI (microsatellite instability) antibodies, anti-MUC-1 antibodies. anti-epithelial tumor antigen (ETA) antibodies, anti-tyrosinase antibodies, anti-ras antibodies, anti-p53 antibodies and antibodies directed against melanoma-associated antigen 1 (MAGE1) can be used in liposomes. For example, the antibodies can be mixed with or tethered to the lipids making up the liposomal shell. VEGF receptor is highly expressed in various tumor-related cells. Active agents including beneficial compounds and/or materials can be loaded into liposomes following conjugation of liposomal lipids with antibodies that specifically bind CD11b, CD33, VEGF receptor, AFP, CEA, CA 19-9, CA-125. MSI, MUC-1, ETA. tyrosinase, ras, p53, MAGE1, or combinations of antibodies directed against these or other tumor antigens.

In some instances, the beneficial compounds and materials can be administered orally, gastrically, or rectally, in combination with a pharmaceutically acceptable vehicle such as an inert diluent or an assimilable edible carrier. They may be in the form of a solution, paste, or foam. They may be enclosed in hard or soft-shell gelatin capsules, may be compressed into tablets, or may be incorporated directly with the food of the patient's diet. They may be combined with one or more excipients and used in the form of tablets, pills, buccal tablets, troches, capsules, elixirs, suspensions, pastes, foams, syrups, wafers, and the like.

Such compositions and preparations may contain at least 0.1% of beneficial compounds and materials. The percentage of the beneficial compounds and materials within compositions and preparations may, of course, be varied. The quantity of beneficial compounds and materials in such compositions is such that an effective dosage level will be obtained.

The dosage forms may also contain any of the following: binders such as gum tragacanth, acacia, corn starch or gelatin; excipients such as dicalcium phosphate; a disintegrating agent such as corn starch, potato starch, alginic acid and the like; a lubricant such as magnesium stearate; polymers such as cellulose-containing polymers (e.g., hydroxypropyl methylcellulose, methylcellulose, ethylcellulose), polyethylene glycol, poly-glutamic acid. poly-aspartic acid or poly-lysine; and a sweetening agent such as sucrose, fructose, lactose or aspartame or a flavoring agent such as peppermint, oil of wintergreen, or cherry flavoring may be added.

Formulations (e.g., tablets) can include one or more of lactose, sucrose. mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders. diluents, buffering agents, moistening agents, preservatives, flavoring agents, dyes, disintegrating agents, and pharmaceutically compatible carriers. Lozenge forms can include the active agents in a flavoring or sweetener, e.g., sucrose, as well as pastilles comprising the beneficial compounds and materials in an inert base, such as gelatin and glycerin or sucrose and acacia emulsions, gels, and the like containing carriers known in the art.

When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. In some cases, the A syrup or elixir may contain the beneficial compounds and materials, sucrose or fructose as a sweetening agent, methyl and propylparabens as preservatives, a dye and flavoring such as cherry or orange flavor.

Of course, any material used in preparing any unit dosage form should be pharmaceutically acceptable and substantially non-toxic in the amounts employed. In addition, the active compound may be incorporated into sustained-release preparations and devices.

Useful solid carriers include finely divided solids such as talc, clay, microcrystalline cellulose, silica, alumina and the like. Useful liquid carriers include water, alcohols or glycols or water-alcohol/glycol blends, in which the beneficial compounds and materials can be dissolved or dispersed at effective levels, optionally with the aid of non-toxic surfactants. Adjuvants such as fragrances and additional antimicrobial agents can be added to optimize the properties for a given use.

Thickeners such as synthetic polymers, fatty acids, fatty acid salts and esters, fatty alcohols, modified celluloses or modified mineral materials can also be employed with liquid carriers to form spreadable pastes. gels, ointments, soaps, and the like. The compositions can be formulated with enteric coatings or for pH-dependent release from coated beads, capsules containing enteric or pH-dependent coatings, or tablets containing enteric or pH-dependent coatings. In some cases, the formulations can be administered orally, via catheter to the bladder, or rectally.

In some embodiments, one or more of the beneficial compounds and materials are linked to polyethylene glycol (PEG). For example, one of skill in the art may choose to link beneficial compounds and materials to PEG to form the following pegylated drug.

Useful dosages of the active agents (e.g., beneficial compounds and/or materials) can be determined by determining their in vitro activities, and/or their in vivo activities in animal models. Methods for the extrapolation of effective dosages in mice, and other animals, to humans are available in the art; for example, see U.S. Pat. No. 4,938,949.

The beneficial compounds and/or materials can be conveniently administered in unit dosage form. The desired dose may conveniently be presented in a single dose or as divided doses administered at appropriate intervals, for example, as two, three, four or more sub-doses per day, or per week, or per month. The sub-dose itself may be further divided, for example, into a number of discrete loosely spaced administrations; such as multiple oral, rectal, bladder, intraperitoneal or intravenous doses. For example, it can be desirable to administer the present compositions locally over an extended period, either by continuous infusion or in separate doses.

The therapeutically effective amount of the active agent(s) (e.g., beneficial compounds and/or materials) necessarily varies with the subject and the disease or physiological problem to be treated. As one skilled in the art would recognize, the amount can be varied depending on the method of administration. The amount of the active agent (e.g., beneficial compounds and/or materials) for use in treatment will vary not only with the route of administration, but also the nature of the condition being treated and the age and condition of the subject and will be ultimately at the discretion of the attendant physician, veterinarian, or clinician.

The pharmaceutical compositions of the invention can include an effective amount of at least one of the active agents of the invention (e.g., one beneficial compound or material), or two or more different beneficial compounds and/or materials. These compositions can also include a pharmaceutically effective carrier.

Beneficial compounds and/or materials may be included in liquid preparations, appropriately buffered, and then injected or introduced (e.g., via catheter) into and/or near treatment sites. Treatment sites can include primary or metastatic sites of cancer tumor cells, sites of infection, or sites suspected of being cancerous or infected.

The pharmaceutical compositions can also include other active ingredients and therapeutic agents, for example, other chemotherapeutic agents, antibiotics, anti-inflammatory agents, analgesics, vitamins, and the like. For example, it may be desirable to combine existing cancer treatments such as radiation and chemotherapy with beneficial compounds and materials (e.g., bacteriocin(s)) to achieve a synergistic result. In some cases, it may be possible to reduce the amount, intensity, or frequency of the existing treatments by use of such combinations, and thereby reduce their unwanted toxic side effects and risks.

Additional chemotherapeutic agents can be included in the compositions that contain the beneficial compounds and/or materials. Examples include but not limited to one or more radioactive drug, topoisomerase inhibitor, DNA binding agent, anti-metabolite, cytoskeletal-interacting drug, ionizing radiation, or a combination thereof.

Cytoskeletal drugs are small molecules that interact with actin or tubulin. Any such cytoskeletal drug can be used in the methods and compositions described herein. Cytoskeletal drugs include paclitaxel, colchicine, cytochalasins, demecolcine, latsunculin, nocodazole, phalloidin, swinholide and vinblastine. Some cytoskeletal drugs stabilize a cytoskeletal component, for example, paclitaxel stabilizes microtubules. Other cytoskeletal drugs prevent polymerization. For example, cytochalasin D binds to actin monomers and prevents polymerization of actin filaments. In some embodiments, the anti-cancer agent is paclitaxel.

A topoisomerase inhibitor that can be used in conjunction with the invention can be, for example, a topoisomerase I (Topo I) inhibitor, a topoisomerase II (Topo II) inhibitor, or a dual topoisomerase I and II inhibitor. A topo I inhibitor can be from any of the following classes of compounds: camptothecin analogue (e.g., karenitecin, aminocamptothecin, lurtotecan, topotecan, irinotecan, BAY 56-3722, rubitecan, G114721, exatecan mesylate), rebeccamycin analogue, PNU 166148, rebeccamycin, TAS-103, camptothecin (e.g., camptothecin polyglutamate, camptothecin sodium). intoplicine, ecteinascidin 743, J-107088, pibenzimol. Examples of preferred topo I inhibitors include but are not limited to camptothecin, topotecan (hycaptamine), irinotecan (irinotecan hydrochloride). belotecan, or an analogue or derivative thereof.

A topo II inhibitor that can be used in conjunction with the invention can be, for example, from any of the following classes of compounds: anthracycline is antibiotics (e.g., carubicin, pirarubicin, daunorubicin citrate liposomal. daunomycin, 4-iodo-4-doxydoxorubicin, doxorubicin, docetaxel, n,n-dibenzyl daunomycin, morpholinodoxorubicin, aclacinomycin antibiotics, duborimycin, menogaril, nogalamycin, zorubicin, epirubicin, marcellomycin, detorubicin, annamycin, 7-cyanoquinocarcinol, deoxydoxorubicin, idarubicin. GPX-100, MEN-10755, valrubicin, KRN5500), epipodophyllotoxin compound (e.g., podophyllin, teniposide, etoposide, GL331, 2-ethylhydrazide), anthraquinone compound (e.g., ametantrone, bisantrene, mitoxantrone, anthraquinone), ciprofloxacin, acridine carboxamide, amonafide, anthrapyrazole antibiotics (e.g., teloxantrone, sedoxantrone trihydrochloride, piroxantrone, anthrapyrazole, losoxantrone), TAS-103. fostriecin. razoxane, XK469R, XK469, chloroquinoxaline sulfonamide, merbarone, intoplicine, elsamitrucin, CI-921, pyrazoloacridine, elliptinium, amsacrine. Examples of preferred topo II inhibitors include but are not limited to doxorubicin (Adriamycin), etoposide phosphate (etopofos), teniposide. sobuzoxane, or an analogue or derivative thereof.

DNA binding agents that can be used in conjunction with the invention include but are not limited to DNA groove binding agent, e.g., DNA minor groove binding agent; DNA crosslinking agent; intercalating agent; and DNA adduct forming agent. A DNA minor groove binding agent can be an anthracycline antibiotic, mitomycin antibiotic (e.g., porfiromycin, KW-2149, mitomycin B, mitomycin A, mitomycin C), chromomycin A3, carzelesin, actinomycin antibiotic (e.g., cactinomycin, dactinomycin, actinomycin F1), brostallicin, echinomycin, bizelesin, duocarmycin antibiotic (e.g., KW 2189). adozelesin, olivomycin antibiotic, plicamycin, zinostatin, distamycin, MS-247, ecteinascidin 743, amsacrine, anthramycin, and pibenzimol, or an analogue or derivative thereof.

DNA crosslinking agents include but are not limited to antineoplastic alkylating agent. methoxsalen, mitomycin antibiotic, and/or psoralen. An antineoplastic alkylating agent can be a nitrosourea compound (e.g., cystemustine, tauromustine, semustine, PCNU, streptozocin, SarCNU, CGP-6809, carmustine, fotemustine, methylnitrosourea, nimustine, ranimustine, ethylnitrosourea, lomustine, chlorozotocin), mustard agent (e.g., nitrogen mustard compound, such as spiromustine, trofosfamide, chlorambucil, estramustine, 2,2,2-trichlorotriethylamine, prednimustine, novembichin, phenamet, glufosfamide, peptichemio, ifosfamide, defosfamide, nitrogen mustard, phenesterin, mannomustine, cyclophosphamide, melphalan, perfosfamide, mechlorethamine oxide hydrochloride, uracil mustard, bestrabucil, DHEA mustard, tallimustine, mafosfamide, aniline mustard, chlomaphazine; sulfur mustard compound, such as bischloroethylsultide; mustard prodrug, such as TLK286 and ZD2767), ethylenimine compound (e.g., mitomycin antibiotic, ethylenimine, uredepa, thiotepa, diaziquone, bexamethylene bisacetamide, pentamethylmelamine, altretamine, carzinophilin, triaziquone, meturedepa, benzodepa, carboquone), alkylsulfonate compound (e.g., dimethylbusulfan, Yoshi-864, improsulfan, piposulfan, treosulfan, busulfan, hepsulfam), epoxide compound (e.g., anaxirone, mitolactol, dianhydrogalactitol, teroxirone), miscellaneous alkylating agent (e.g., ipomeanol, carzelesin, methylene dimethane sulfonate, mitobronitol, bizelesin, adozelesin, piperazinedione. VNP40101M, asaley, 6-hydroxymethylacylfulvene, E09, etoglucid, ecteinascidin 743, pipobroman), platinum compound (e.g., ZD0473, liposomal-cisplatin analogue, satraplatin, BBR 3464, spiroplatin, onnaplatin, cisplatin, oxaliplatin, carboplatin, lobaplatin, zeniplatin, iproplatin), triazene compound (e.g., imidazole mustard, CB 10-277, mitozolomide, temozolomide, procarbazine, dacarbazine), picoline compound (e.g., penclomedine), or an analogue or derivative thereof. Examples of preferred alkylating agents include but are not limited to cisplatin, dibromodulcitol, fotemustine, ifosfamide (ifosfamid), ranimustine (ranomustine), nedaplatin (latoplatin), bendamustine (bendamustine hydrochloride), eptaplatin, temozolomide (methazolastone), carboplatin, altretamine (hexamethylmelamine), prednimustine, oxaliplatin (oxalaplatinum), carmustine, thiotepa, leusulfon (busulfan), lobaplatin, cyclophosphamide, bisulfan, melphalan, and chlorambucil, or analogues or derivatives thereof.

Intercalating agents can be an anthraquinone compound, bleomycin antibiotic, rebeccamycin analogue, acridine, acridine carboxamide, amonafide, rebeccamycin, anthrapyrazole antibiotic, echinomycin, psoralen, LU 79553, BW A773U, crisnatol mesylate, benzo(a)pyrene-7,8-diol-9,10-epoxide, acodazole, elliptinium, pixantrone, or an analogue or derivative thereof, etc.

DNA adduct forming agents include but are not limited to enediyne antitumor antibiotic (e.g., dynemicin A, esperamicin A1, zinostatin. dynemicin. calicheamicin gamma II), platinum compound, carmustine, tamoxifen (e.g., 4-hydroxy-tamoxifen), psoralen, pyrazine diazohydroxide, benzo(a)pyrene-7,8-diol-9,10-epoxide, or an analogue or derivative thereof.

Anti-metabolites include but are not limited to cytosine, arabinoside. floxuridine, fluorouracil, mercaptopurine, Gemcitahine, and methotrexate (MTX).

Monoclonal antibodies, cancer vaccines, angiogenesis inhibitors, and gene therapy are targeted therapies that can also be combined into compositions and used in the methods described herein.

In addition to cancer treatment, there are other treatments where beneficial compounds and/or materials (e.g., bacteriocins) may be applied. Nisin or salivaricin, or other beneficial compounds and/or materials, may be used to make a liquid or a paste preparation, such as a mouth wash or toothpaste. The mouth wash or toothpaste could be used to control the population of specific organisms that inhabit the oral cavity, such as *Streptococcus mutans*. A similar liquid, buffered with NaCl, could be used as a nasal rinse to kill MRSA, or other bacterial infections of the sinus or ear. A liquid formulation could be used as a gargle to treat strep throat. A similar liquid could be used as a tonic to be swallowed to kill off bacteria such as *Campylobacter*, and other microbes that produce excess lipopolysaccharides (LPS) near the lower esophageal sphincter. This may reduce the impact LPS can exert with respect to the slowing of gastric emptying and concomitant inhibition of the closure of the sphincter muscle—effectively treating GERD acid reflux, heartburn, and sour stomach. Ear drops, formulated to penetrate the eardrum (adjuvants or nanoparticles), could be used to kill off bacterial infections of the outer and middle ear.

Beneficial compounds and/or materials (e.g., bacteriocins) may also be included in ointment formulations to be applied topically. For example, nisin, or other bacteriocins could be used as a lip balm or moisturizer to treat or protect against squamous cell carcinoma of the lip or skin. Such ointment could also be used to treat MRSA infections of the skin.

Kits

A variety of kits are described herein that include any of the probiotic compositions, prebiotic compositions, beneficial compounds, beneficial materials, and/or agents described herein. The compositions, compounds, materials, and/or agents described herein can be packaged separately into discrete vials, bottles. packets, or other containers. Alternatively, any of the compounds, materials, and/or agents described herein can be packaged together as a single composition, or as two or more compositions that can be used together or separately. The compositions, beneficial compounds. beneficial materials, and/or agents described herein can be packaged in appropriate ratios and/or amounts to improve the health of a subject.

A kit is described herein can include tools for collection of samples and for testing of the samples. For example, the kits can include one or more sterile cell collection devices such as a vial. bottle, swab, sterile containers for sample or cell collection, skin scrapping device, needle, syringe, and/ or scalpel.

A kit is described herein can include container and media for in vitro culture of tissues or cells collected, for example, for testing to determine what types of cells, viruses, or tissues (e.g., disease-related cells, viruses, or tissues) that the subject may have. The kits can also include antibodies for detection of cell markers for various disease-related cells, fungi, viruses, or tissues. For example, the kits can have antibodies for detection of cancer cell markers, for detection of microbial infections (e.g., bacterial or fungal infections), and/or for detections of viral infections.

Some kits can include a cell culture medium or a variety of cell culture media that includes any of the compositions. compounds and/or agents described herein. The instructions can include guidance for culturing and assaying cells, viruses, or tissues that can be present in a sample to determine the identity what types of cells, viruses, or tissues that can be present in a sample. For example, the instructions can describe sample collection, culturing methods, assay methods.

The kits can include any of the compositions, beneficial compounds, beneficial materials, and/or agents described herein, as well as instructions for using those compositions, beneficial compounds, beneficial materials, and/or agents. For example, the kits can include challenger probiotic compositions, protagonist probiotic compositions, and/or prebiotic compositions as well as administration schedules for treatment of various diseases.

For example, the instructions can describe procedures for rehydration, dilution, formulation, or combination of the compositions, beneficial compounds, beneficial materials, and/or agents described herein. The instructions can describe when and how to add other compounds and/agents to a composition. Any of the kits can also include vials or containers for mixing, diluents, pharmaceutically acceptable carriers, catheters, bladder catheterization systems. enema delivery systems. needles, syringes, and the like.

The instructions can describe methods for therapeutic treatment of a subject, including when to combine administration of selected probiotic compositions, prebiotic compositions. beneficial compounds, beneficial materials, and/or agents, and when to administer a probiotic composition by itself, a prebiotic composition by itself, a compound by itself, a material by itself, and/or agents by themselves. The instructions can describe administration schedules for probiotic compositions, prebiotic compositions, beneficial compounds, beneficial materials, and/or agents to provide therapeutic treatment of various disease in a subject.

The probiotic compositions, prebiotic compositions, beneficial compounds, beneficial materials, and/or agents can be provided in a delivery device within any of the kits described herein. Alternatively, a delivery device can be separately included in the kit(s), and the instructions can describe how to assemble the delivery device prior to administration to a subject. The delivery device can provide a scaffold for cell growth and/or a matrix for controlled release of any of the compositions, compounds or agents described herein.

The kits can provide other agents described herein for the compositions in any of the preceding sections.

The following Examples illustrates some of the experiments involved in the development of the invention.

Example 1: Intestinal Growth of Microorganisms Upon Consumption of High Maltose Syrup by a Placebo Group Thirteen human subjects in a 'placebo' group were given 1.5 mL of a high-maltose syrup per day for 12 weeks as a control for comparison to those receiving a prebiotic composition (see Example 2).

High maltose syrup contains a high percentage of maltose (e.g., 60%-65% or more) as well as some maltodextrins with different degrees of polymerization (DP 3-7; e.g., about 20% or less maltodextrins), and a small amount of glucose (e.g., 2-3%). An example of a high maltose syrup composition is shown below in Table 5.

TABLE 5

| High Maltose Syrup Composition | |
|---|---|
| Brix g/100 g DS | 82.7 |
| glucose, %/brix | 2.21 |
| maltose, %/brix | 65.70 |
| DP 3, %/brix | 16.24 |
| DP 4, %/brix | 2.29 |
| DP 5, %/brix | 0.76 |
| DP 6, %/brix | 0.39 |
| DP 7, %/brix | 0.09 |

The terms DP 3, DP 4, DP 5, DP 6, and DP 7 in the list above refer to maltodextrins with different degrees of polymerization (DP 3-7).

The majority if not all of high maltose syrup is digested in the upper digestive tract (e.g., in the mouth, esophagus, stomach, small intestine, and combinations thereof). Thus, this Example illustrates a baseline microbial population of subjects who have not received a prebiotic as well as the types of assay procedures that can be used to identify such a microbial population.

Each subject submitted three fecal swabs. The first swab was submitted at one week before taking the high maltose placebo, the second swab was submitted the day before taking the placebo and the final sample at the end of week 12 after taking the placebo.

The rRNA from the fecal samples was isolated and the diversity of 16s rRNA sequences in the samples were identified by sequencing. The sequences were cross-referenced via Basic Local Alignment Search Tool (BLAST) analysis to identify the organisms. From these data, the species with an abundance of greater than or equal to 0.1% of the total number of reads were listed.

The selected list of organisms was interrogated for enzymes that can digest oligosaccharides containing α-1,6 glycosidic linkages, e.g. oligodextran (isomaltooligosaccharides). Such enzymes are exemplified by oligo-α-1,6-glucosidase and α-1,6-glucosidase, and encoded by the DexA and DexB genes, respectively. The enzyme types were identified in the UniProt database by BLAST analysis, and the abundance of bacterial species that can ferment oligodextran was therefore predicted.

A protein BLAST (BLASTP) was performed via UNI-PROTKB using the following query protein sequence (SEQ TD NO:7).

```
>tr|H5T0P3|H5T0P3_LACLL Oligo-1,6-glucosidase OS =
Lactococcus lactis subsp. lactis IO-1 GN = dexA
PE = 4 SV = 1
MNSHLNGVVN MKENWWQKTV VYQIYPRSFM DANGDGVGDL

QGIISKLDYL EKLGIGAIWL SPVYQSPMDD NGYDISDYQA

IADVFGTMSD MDELLLEAKK RNIQIVMDLV VNHTSDEHKW

FVEARKSKDN AYRDYYIWAD EPNALQSTFS GSAWEFDEES

GQYFLHLFSK RQPDLNWENP QVHQEVYDMM NFWIDKGIGG

FRMDVIDLIG KEIDQEITGN GRKLHEYLHE MNQATFGQKN

LLTVGETWGA TPEIAELYSD PKRQELSMVF QFEHITNAYL

DEGEKWDKKE FSVSKLKEIL AKWQALEKGW NSLFWNNHDL

PRIVSNWGND GKYRLKSAKA FAILLHLMKG TPYIYQGEEL

GMTNYPFESI EEVNDIESRN MFAERLAAGH SENEIMDSIR

RVGRDNARTP MQWTAGENAG FTDGKPWLAV NPNHEEINAD

QAMSDPDSVF YTYQKLIELR KQHDWVIYGG FKLIDSEADV

FAYLRTYKGK KYLVVANLSD EENQFKTGFV CRDLLIHNEN

FLPELSQIKL KAWEAFACEV E
```

The run time for such a BLASTP analysis was about 2.5 minutes.

Table 6 shows a list of the alpha glucosidases, or oligo-α-1,6-glucosidases identified at the species level for *L. lactis* subsp. *lactis* which was found in the fecal samples, where the match quality is the percentage reflecting how closely the result(s) matched the protein sequence encoded by the given dexA gene. The amino acid sequence for the *Lactococcus lactis* glucan 1,6-alpha-glucosidase is shown above (SEQ ID NO:7). The 'Number' is the accession number of the gene (see website at www.ebi.ac).

TABLE 6

Glucosidases coded in *L. lactis* demonstrating a match quality of >98%.

| Number | Protein Name | Identity |
| --- | --- | --- |
| U5PLX9 | Glucan 1,6-alpha-glucosidase (*Lactococcus lactis* subsp. 1a) | 100% |
| D2BKX1 | Glucan 1,6-alpha-glucosidase (*Lactococcus lactis* subsp. 1a) | 98.9% |
| A0A0B8QQV6 | Glycosidases (*Lactococcus lactis* subsp. 1a) | 98.7% |
| A0A089ZEV7 | Glucan 1,6-alpha-glucosidase (*Lactococcus lactis*) | 98.9% |
| A0A0V8CJV8 | Glucan 1,6-alpha-glucosidase (*Lactococcus lactis* subsp, 1a) | 98.5% |
| H5TOP3 | Oligo-1,6-alpha-glucosidase (*Lactococcus lactis* subsp. 1a) | 98.7% |
| T0WEN3 | Glucan 1,6-alpha-glucosidase (*Lactococcus lactis* subsp. 1a) | 98.7% |
| Q9CF00 | Oligo-1,6-alpha-glucosidase (*Lactococcus lactis* subsp. 1a) | 98.7% |
| A0A0V8AN11 | Glucan 1,6-alpha-glucosidase (*Lactococcus lactis* subsp. 1a) | 99.4% |
| S6FS83 | Trehalose-6-phosphate hydrolase (*Lactococcus lactis* subsp. 1a) | 99.1% |
| A0A0V8BDL7 | Glucan 1,6-alpha-glucosidase (*Lactococcus lactis* subsp. 1a) | 99.2% |
| U6EPQ0 | Glucan 1,6-alpha-glucosidase (*Lactococcus lactis* subsp. 1a) | 98.8% |
| A0A0V8C313 | Glucan 1,6-alpha-glucosidase (*Lactococcus lactis* subsp. 1a) | 99.1% |

Several species were noted to be natively present in low but in most of the fecal samples tested included such bacterial species. These natively present bacterial species included *Bacillus subtilis*, *Lactococcus lactis* subsp. *lactis*, and *Pediococcus acidolactici*.

Sequencing data indicated a cohort of genes were present in the fecal microorganisms that are particularly suited for glucan transport and metabolism, for example, α-1,4 and α-1,6 glucanohydrolase (glucosidase) enzymes (Table 5). These organisms are predicted to be able to utilize iso-maltooligosaccharides, and specifically MIMO.

Data from this placebo group of subjects who ingested a high maltose syrup composition shows that the types of microorganisms in the gut can be detected and that a specific group of organisms that may utilize a particular ingested prebiotic composition can be identified (e.g., by identifying enzymes encoded in the genomic sequences that are present in those bacteria) in groups of subjects.

Example 2: Intestinal Growth of Microorganisms Upon Consumption of ISOThrive™ MIMO Twenty-six human subjects were given 1.5 mL (Ig) of ISOThrive™ MIMO per day as a prebiotic composition for 12 weeks. Examples of two batches of the ISOThrive™ composition are shown below in Table 7.

TABLE 7

ISOThrive ™ Batch Compositions

| | Batch 1 | Batch 2 |
| --- | --- | --- |
| brix: | 20.0 | 19.8 |
| mannitol | 10.26 | 24.08 |
| fructose | 0.56 | 0.08 |
| sucrose | 4.08 | 1.25 |
| maltose | 2.63 | 3.11 |
| MIMO-DP 3 | 12.04 | 8.79 |
| MIMO-DP 4 | 21.87 | 20.14 |
| 1,4-DP3 | 6.61 | 6.80 |
| MIMO-DP 5 | 13.41 | 13.96 |
| MIMO-DP 6 | 4.18 | 5.25 |
| MIMO-DP 7 | 1.63 | 2.14 |
| MIMO-DP 8 | 0.00 | 0.87 |
| 1,4-DP4 | 2.51 | 2.80 |
| MIMO-DP 9 | 0.00 | 0.00 |
| lactate | 4.23 | 10.79 |
| glycerol | 0.05 | 0.13 |
| formate | 0.00 | 0.02 |
| acetate | 1.69 | 4.10 |
| TOTAL: | 91.04 | 104.30 |
| MIMO, %: | 53.13 | 51.14 |
| Purity, %: | 58.36 | 49.03 |
| MWD: | 693.21 | 723.7 |
| Yield %: | 67.30 | 55.98 | where 1,4-DP3, and 1,4-DP4 are maltodextrins.

Each subject submitted three fecal swabs. The first swab was submitted at one week before taking the high maltose placebo. the second swab was submitted the day before taking the placebo and the final sample at the end of week 12 after taking the placebo.

The rRNA from the fecal samples was isolated and the diversity of 16s rRNA sequences in the samples were identified by sequencing. The sequences were cross-referenced via Basic Local Alignment Search Tool (BLAST) analysis to identify the organisms. From these data, the species with an abundance of greater than or equal to 0.1% of the total number of reads were listed.

During the period of the two baseline samples, the placebo group (receiving high maltose syrup throughout, Example 1) and the intervention group (receiving ISOThrive™ MIMO, Example 2) each consumed the same high-maltose syrup placebo. During such a baseline time, an equivalent number of reads for L. lactis subsp. lactis was detected (0.048% total reads). This indicates that the subjects in the placebo and intervention groups had similar populations of microorganisms, and that the placebo (high maltose syrup) had no effect on the growth or metabolism of L. lactis subsp. lactis residing in the colon.

L. lactis subsp. lactis has a high prebiotic index for oligodextran and may utilize MIMOs. In vitro testing (2 L fermentation of 2.5% ISOThrive™ PSF at colonic physiological pH and temperature) confirmed that L. lactis subsp. lactis consumed the ISOThrive™ PSF.

In order to confirm positive growth in-vivo, the fecal microbiota of the intervention group was compared. At the conclusion of the trial, the percent of the total reads increased to 0.483% for the intervention group that received ISOThrive™ MIMO while the number of reads for the placebo group remained at 0-0.048%.

Hence, ingestion of the ISOThrive™ product, which has high levels of particular types of maltosyl-isomaltooligosaccharides (MIMOs), can facilitate growth of microorganisms in the gut that express the appropriate cohort of enzymes (glucosidase-type, in this case) required to utilize the prebiotic (MIMO, in this case).

Example 3: Lactococcus lactis Subsp. lactis NRRL B-1821 Growth in Media Containing Maltosyl-Isomaltooligosaccharides (MIMOs)

As indicated in Example 1, Lactococcus lactis was natively present in fecal samples of human subjects.

The number of appropriate genes encoded for the fecal sample microorganisms was sorted and weighted by quality of match (in this case, weighting factors of 5, 3, and 1 were applied for match qualities of >99, >98, and >97%, respectively. The sum of these factors is defined here as the prebiotic index for the subject organism. Thus, the higher the score, the more likely they will be able to be consumed by the subject organism. Such a prebiotic index can be a useful measure of whether a compound or composition can support the growth of a microorganism or a mixture of microorganism. The Lactococcus lactis organism was identified in the placebo group via 16S rRNA sequencing. Sequences for glucosidase-type genes (e.g., dexA and dexB, see UniProtKB website at uniprot.org/blast/uniprot/B20160624-14483A1C7ED25EE8374758DF3FD545FD122F2AF) were interrogated via BLAST analysis (nucleotide to protein) to reveal 12 genes (two oligo-1,6-glucosidase, ten 1,6-glucosidase) with match quality >99%. This (weighted by match quality and number of genes) gives MIMO a potential prebiotic index (PrbI) of 60 (Q>99%, PrbI 83>97%), indicating that Lactococcus lactis are extremely likely to consume MIMO.

This Example illustrates that Lactococcus lactis strains can grow in and metabolize media containing maltosyl-isomaltooligosaccharides (MIMOs).

Lactococcus lactis subsp. lactis NRRL B-1821 was evaluated. Although not extensively studied as a probiotic organism, L. lactis subsp. lactis has a number of desirable traits such as acid-tolerance and resistance to bile (Kimoto, et al. 1999, Lett. Appl. Microbiol. 29, pp. 313-316). More recently, the species has been evaluated as a probiotic, and that certain strains exhibit anti-inflammatory potential (e.g., increased CD4+ T cells, early increases in TL-6 with sustained production of IL-10) for the treatment for inflammatory bowel disease [IBD, Luerce, et al. 2014. Gut Pathogens 6 (33), 11 pp]. Additionally, certain Lactococcus lactis strains may be capable of producing several isoforms of the lantibiotic bacteriocin nisin (Beasley and Saris, 2004 Appl. Environ Microbiol. 70 (8), pp. 5051-5053). For example, Nisin ZP (Shin et al. 2015. Front. Microbiol. 6:617), isolated from Lactococcus lactis subsp. lactis DF04Mi (Furtado, et al. 2014. Braz. J. Microbiol. 45(4), pp. 1541-1550), has recently been observed to reduce the size and proliferation of head/neck tumors in-vitro and in mice (Kamarajan, et al. 2015. PLoS One. 10(7): 20 pp).

Methods:

M17 Media (Sigma) was prepared by dissolving 4.207 g M17 in 100.017 g (total) water (18MΩ). The media mixture was autoclaved at 121° C. for 15 min. After cooling, the media was inoculated with Lactococcus lactis subsp. lactis NRRL B-1821 (0.5 mL late log-phase culture frozen at −78° C. in 20% glycerol), and the culture was incubated at 35° C. for 16 Hr. This culture was the inoculum for the following fermentation.

To a 2 L fermenter (New Brunswick BioFlo/Celligen 115) was added water (18MΩ), 0.960 kg; peptone (meat), 10.080 g; yeast extract, 5.690 g; ISOThrive™ MIMO (lot #160120, a source of maltosyl-isomaltooligosaccharides (MIMOs)). 25.067 g; $MnSO_4$—$H_2O$, 0.0123 g; $MgSO_4$, 0.1156 g; $FeSO_4$-$7H_2O$, 0.0135 g; $KH_2PO_4$, 2.933 g; NaCl. 0.01208 g, and $CaCl_2$-$2H_2O$, 0.6178 g. This fermentation media was autoclaved at 121° C. for 15 minutes. Once cooled to 35° C., a physiological temperature (36-37° C.) was maintained using a recirculating water bath. The pH of the fermentation mixture was adjusted to the physiological pH of the colon (pH 6.6) with NaOH (50% w/w) and maintained throughout at pH 6.6 using NaOH (40% w/w).

To the fermenter was aseptically added 10 mL late log-phase Lactococcus lactis subsp. lactis NRRL B-1821 inoculum, and micro-anaerobic (self-blanketing) conditions were maintained. The fermentation was allowed to proceed for 21 Hr before sampling. The headspace contained 7.79% $O_2$ and 5.5% $CO_2$ (PBI Dansensor CheckMate 9900) indicating potential evolution of $H_2$ and/or methane.

The cells were removed via centrifugation (Sorvall RC-5B+, G3 rotor) at 13,689 g for 20 minutes. The supernatant was sampled via HPLC-RID/HPAEC-PAD and the remainder frozen at −78° C. pending analysis of bacteriocin content. The target bacteriocin was nisin, MSTKDFNLD-LVSVSKKDSGASPRITSISLCTPGCKTGALMGCNMK-TATCHCSIHVSK (SEQ ID NO:8, coded by structural gene nisA) that can be assayed by disk diffusion assay (2.5% nisin from Sigma used as a standard). The samples are also being prepared for mass spectrometry (target 3.358 kDa). A small subsample of the biomass was resuspended, washed, and centrifuged again (Eppendorf 5415 C) at 12 kRPM for 15 minutes. The washed biomass pellet was re-suspended and gram stained for confirmation of culture morphology and purity via oil-immersion microscopy.

Results

Essentially all of the tested prebiotic ISOThrive™ MIMOs in the media had been consumed by 21 hours of incubation. The culture was pure, and the late log morphology conformed with Lactococcus spp.

Figure 2:
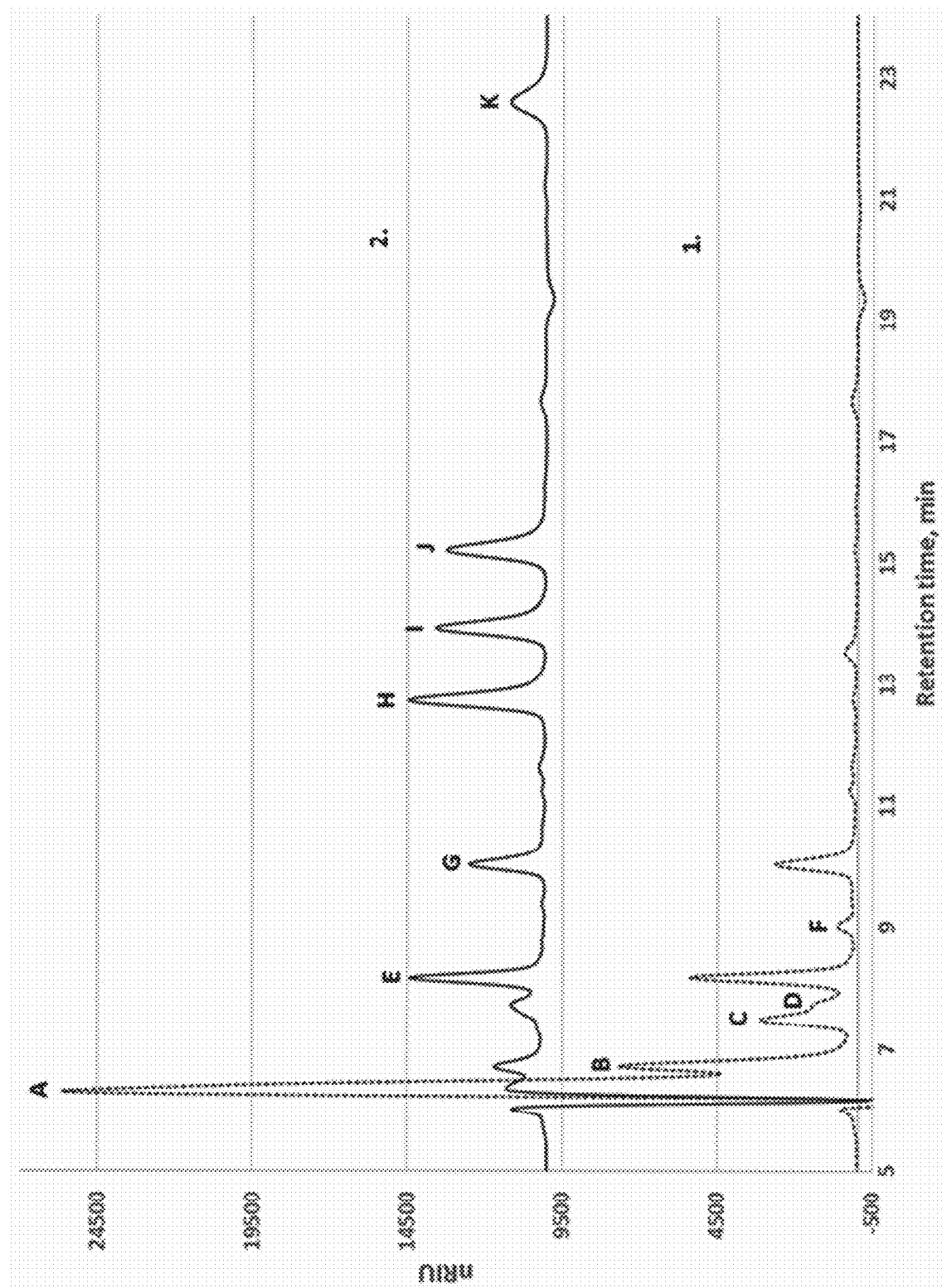
FIG. 2 graphically illustrates the metabolic profile (as detected by HPLC-RID) of *L. lactis* subsp. *lactis* NRRL B-1821 after growth in media with ISOThrive™ MIMO as a sole carbon source. Trace 1: Pre-inoculum media. Trace 2: media after 21 Hr fermentation. The peaks identified were: A, MIMO DP>3; B, panose; C, maltose; D. leucrose; E. unknown acid from media; F, glucose; G, mannitol; H, lactate; I. formate; J, acetate, and K, ethanol.
Figure 3:
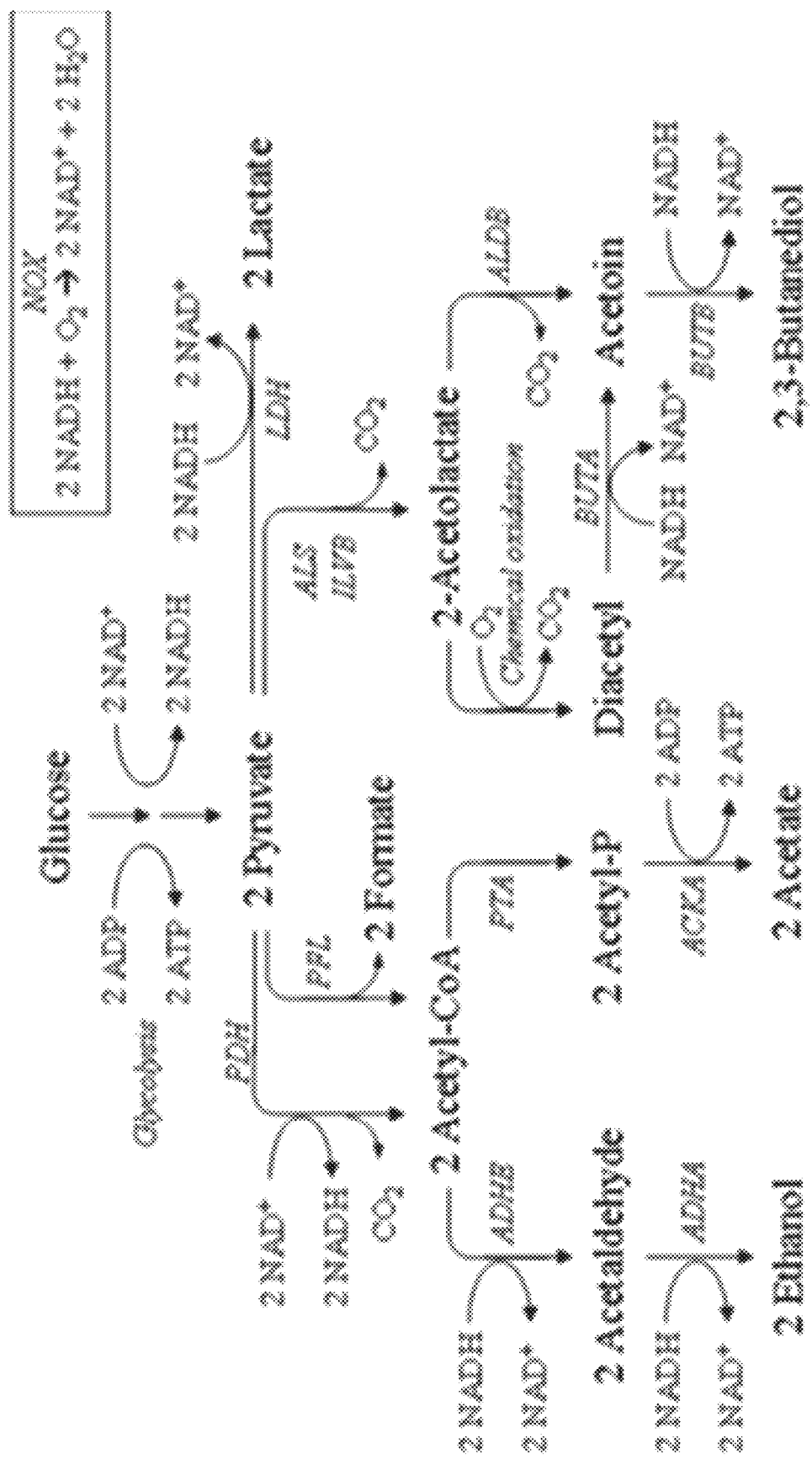
FIG. 3 illustrates the fermentative pathways for *Lactococcus lactis* (Oliveira et al. BMC Microbiology. 5:39 (2005)].

The carbohydrate profiles before and after fermentation are shown (HPAEC-PAD) for the pre-inoculum and 21 Hr samples in FIG. 1. As illustrated in FIG. 2, pyruvate metabolism was observed when the MIMO carbon source was used during fermentation. In other words, lactate, formate, acetate, and ethanol were produced. However, 2,3-butanediol was not detected, as illustrated in FIG. 2. The pathways of fermentative metabolism for this organism are given in FIG. 3.

The broth exhibited antimicrobial activity relative to standard nisin (2.5%, Sigma-Aldrich), via disk diffusion assay vs. *Weissella viridescens* (susceptible organism) on MRS agar.

Example 4: *Bacillus subtilis* NRRL B-23049 Growth in Media Containing Maltosyl-Isomaltooligosaccharides (MIMOs)

Microorganisms from fecal samples obtained from the human subjects who had taken 1.5 mL of a high-maltose syrup (placebo) per day, for 12 weeks, were identified via 16S rRNA sequencing, and sequences for genes from such microorganisms that may encode to glucosidase-type enzymes (e.g., dexA and dexB) were elucidated; see UniProtKB database) via BLAST analysis (nucleotide to protein) as described in Example 1.

Such analysis revealed a microorganism with two genes (one oligo-1,6-glucosidase, one 1,6-glucosidase) with match quality >99%, 3 genes >98%, and 3 genes >97%. When weighted by match quality and number of genes, the MIMO prebiotic has a potential prebiotic index of 20 indicating that this microorganism is likely to consume MIMO, but that it is not likely the preferred substrate. This organism is *Bacillus subtilis*.

Perhaps the oldest known probiotic. *Bacillus subtilis* (and many other *Bacillus* spp.) is able to survive by sporulation. The *Bacillus* spores are highly resistant to temperature and acidic pH. which explains why the species is frequently found in camel dung (which incidentally has been used directly as a probiotic to treat diarrhea by the Bedouin tribes), and why it can survive transit through the human gastrointestinal tract (Damman, et al. 2012, Am. J. Gastroenterol. 107, pp. 1452-1459). Although long regarded as an obligate aerobe, it has been found to be facultatively anaerobic (Nakano and Zuber, 1998, Ann. Rev. Microbiol. 52. pp. 165-190). These features greatly improve the probability that this microorganism can survive in the anaerobic environment of the colon (and handling to that point). Once there, and vegetative. it may be able to enhance mitogenic-induced T cell proliferation (Ciprandi et al. 1986. Chemoterapia 5 (6), pp. 404-407), and may be an effective antitumor immunotherapeutic agent [immunostimulatory effects, NK cytotoxicity augmentation, and up-regulation of IFN-a/y from leukocytes, in mice; Shlyakhovenko, et al. Experimental Oncology 25 (2), pp. 119-123]. *Bacillus* species have also been used as an antidiarrheal [Mazza, 1994. Boll. Chim. Farm. 133 (1), pp. 3-181.

Methods:

Media was prepared containing 0.5% w/w each of tryptone (Sigma, casein) and yeast extract (Marcor bacteriological); 0.11% $KH_2PO_4$; 2.60% ISOThrive™ MIMO (lot #160120); 5.19% mannitol; and DI water (18MΩ) to 100 mL. The media was autoclaved at 121° C. for 15 min. After cooling, the media was inoculated with *Bacillus subtilis* NRRL B-23049 (0.5 mL late log-phase culture frozen at −78° C. in 20% glycerol), and incubated at 35° C. for 16 Hr. This culture was the inoculum for the following fermentation.

To a 2 L fermenter (New Brunswick BioFlo/Celligen 115) was added water (18MΩ), 0.851 kg; tryptone (casein), 5.012 g; yeast extract, 5.000 g; ISOThrive™ MIMO (lot #160120). 25.100 g; $KH_2PO_4$, 1.018 g and mannitol, 50.000 g. This fermentation media was autoclaved at 121° C. for 15 minutes. Once cooled to physiological temperatures, 35-37° C., this temperature was maintained using a recirculating water bath. The pH was adjusted to the physiological pH of the colon (pH 6.6) with NaOH (50% w/w) and maintained throughout using NaOH (40% w/w).

To the fermenter was aseptically added 25 mL late log-phase inoculum, and micro-anaerobic (self-blanketing) conditions were maintained. The fermentation was allowed to proceed for 24 Hr before sampling. The headspace contained 8.65% O2 and 4.4% $CO_2$ (PBI Dansensor CheckMate 9900). The fermenter headspace was then aerated, and the whole sampled again at 44 and 72 Hr. The cells were removed via centrifugation (Sorvall RC-5B+, G3 rotor) at 13,689 g for 20 minutes. The supernatant was sampled for analysis via HPLC-RID/HPAEC-PAD and the remainder frozen at −78° C. pending analysis of bacteriocin (target entianin, encoded by the emS structural gene, 3.446 kDa) content, for example, by mass spectrometry. A sequence for an entianin bacteriocin is shown below (SEQ ID NO:9).

| | | | |
|---|---|---|---|
| 1 | MRLTISRKES | LVFLTLILIN | LLVGGIGAFN | MQHIIQKTDE |
| 41 | INTKWIDGIK | EITSINYLTE | HLSSKEKDFL | IFTDKSKMDT |
| 81 | LDQEMNQILE | DINQKLDSYE | KTISNDKEQK | LFEELQNEVN |
| 121 | TYADIHAQII | ESGRTNDMDK | ARGLLVQTEA | SFENMKKSVT |
| 161 | QLVDFNKEGS | NTAVKETKDV | YHKGLIYTAS | LVAASIIISI |
| 201 | FIWLYITRNI | VKPIIRMKES | ANHIAEGDLS | SDIEPLNSKD |
| 241 | ELGDLNEALQ | KMVGNLRDIV | GYSKEISSRV | LSSSQVLATA |
| 281 | TNETRSGSKH | ITETMNEMAE | GSEQQAQDAV | TIAESMNEFT |
| 321 | ESIDKAYNHG | ITISDTSQNV | LELAVSGNEN | MDTSLQQMKT |
| 361 | IHHIVQEAVH | KVRSLEQHSQ | DINKLVQVIN | GIAEQTNLLS |
| 401 | LNAAIEAARA | GESGKGFAVV | AEEVRKLADG | VSDSVQDITR |
| 441 | IVNGTQQEIY | TVIEYLESSF | TEVEKGTENL | TDTGQAMQHI |
| 481 | KQSVTHVADS | IKEVTDGLKQ | LTNQSITINQ | SIENIASVSE |
| 521 | ESAAGIEETF | SITEQSAHSM | DQVLQNAEEL | EQLAKELNEK |
| 561 | MNQFTI | | | |

A small subsample of the biomass was re-suspended to wash and centrifuged again (Eppendorf 5415 C) at 12 kRPM for 15 minutes. The washed biomass pellet was re-suspended and gram stained for confirmation of culture morphology and purity via gram stain/oil-immersion microscopy.

Results

As the genetic information suggested ($PrbI_{MIMO}=20$), *Bacillus subtilis* NRRL B-23049 was only able to partially consume MIMO.

Figure 4:
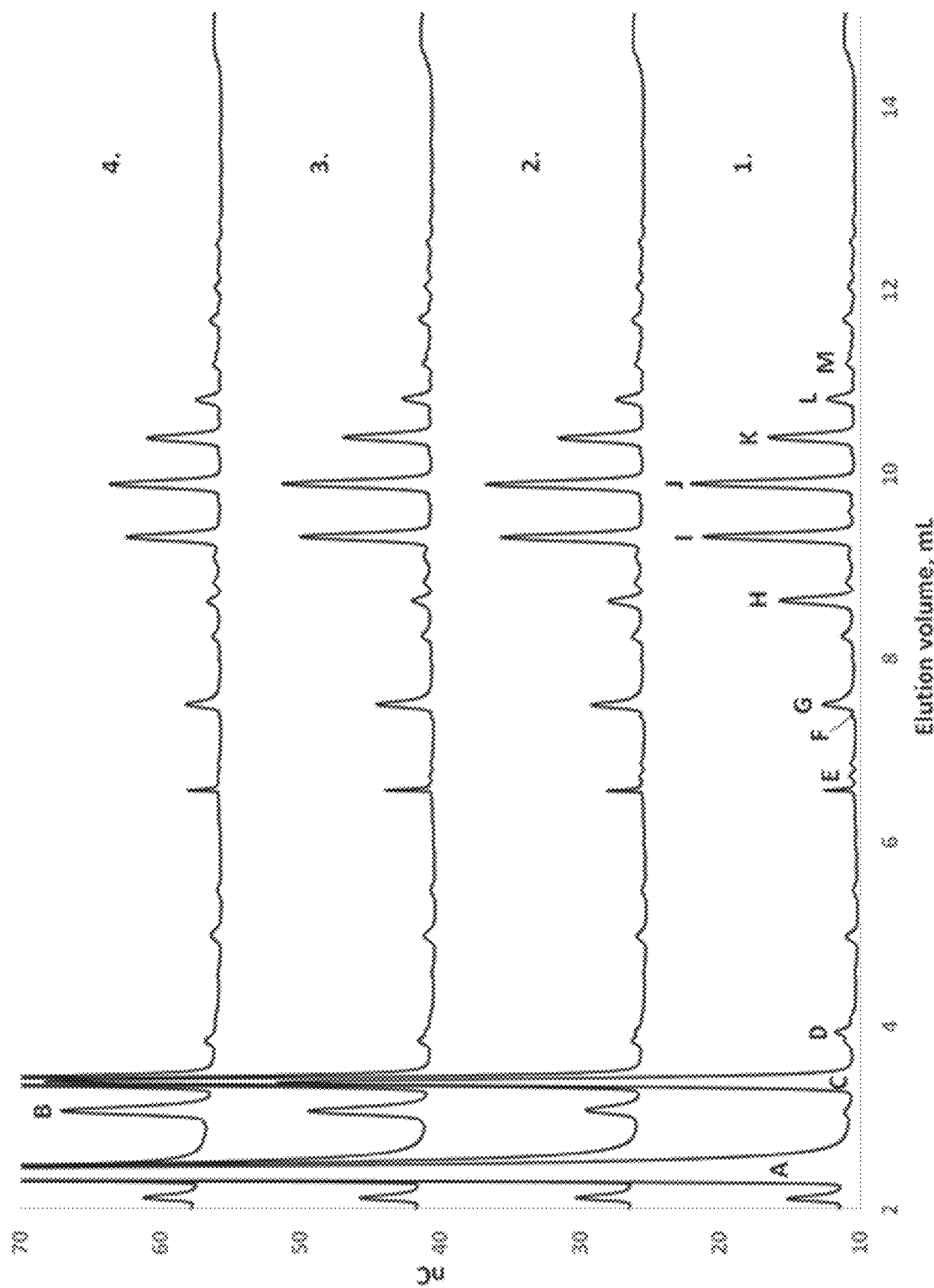
FIG. 4 illustrates overlaid HPAEC-PAD chromatograms of fermentation media containing ISOThrive™ MIMO with *B. subtilis* NRRL B-23049, at various time points of fermentation. Trace 1: pre-inoculum. Trace 2: media after 24 hr incubation. Trace 3 media after 44 hr fermentation. Trace 4: media after 72 hr fermentation. The components detected by HPAEC-PAD were: A, mannitol; B, unknown: C, L-arabinose (IS); D, glucose; E, isomaltotriose; F; isomaltotetraose; G, maltose, and H-M, PAN-type MIMO with DP 4-8.
Figure 5:
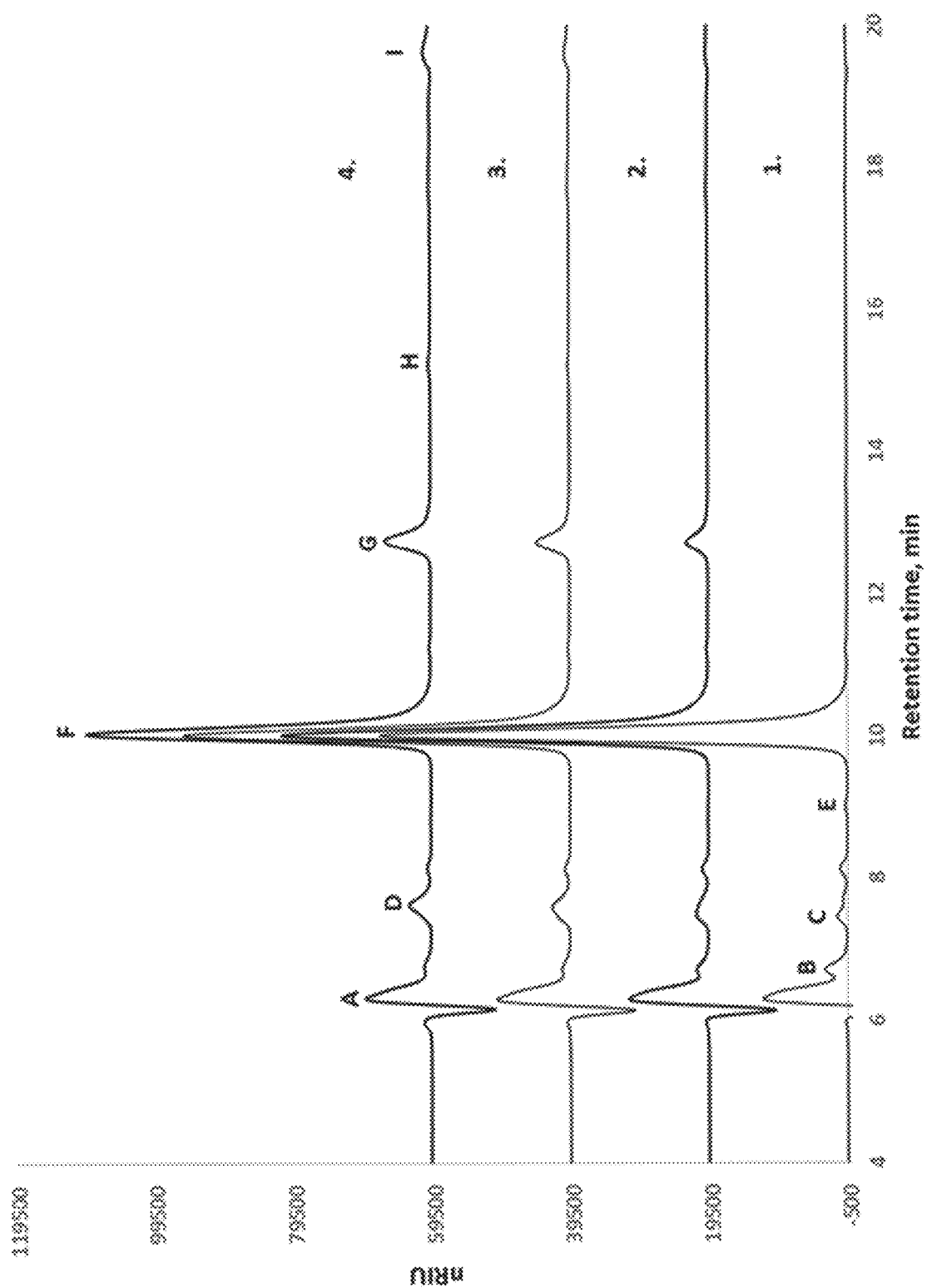
FIG. 5 illustrates the metabolic profile (HPLC-RID) of *B. subtilis* NRRL B-23049 during fermentation in media containing ISOThrive™ MIMO as a sole carbon source. Trace 1: Pre-inoculation media Trace 2: media after 24 Hr fermentation. Trace 3: media after 44 Hr fermentation. Trace 4: media after 72 Hr fermentation. The components detected in the media were: A, MIMO DP>3; B, panose; C. maltose; D, leucrose; E, glucose; F. mannitol; G. lactate; H, acetate, and I, unknown diol.
Figure 6:
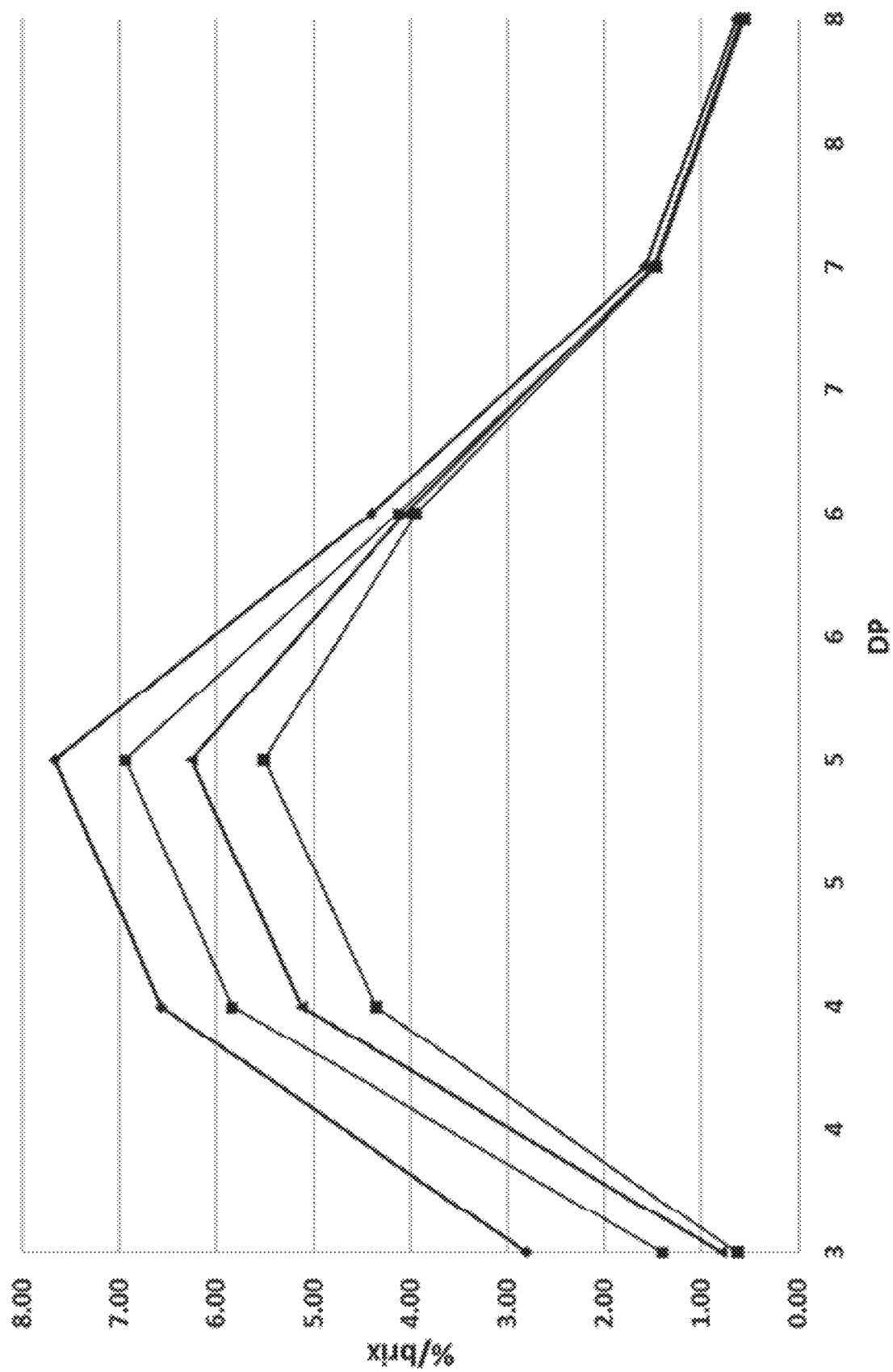
FIG. 6 graphically illustrates the rate of consumption by *B. subtilis* NRRL B-23049 of ISOThrive™ MIMOs with different degrees of polymerization (DP 3-7) at different time points in the fermentation. Top line: 0 hr fermentation. Second from the top line: 24 hr fermentation. Third line from the top: 44 hr fermentation. Bottom line: 72 hr fermentation.

This is evident in FIGS. 4-6 where smaller carbohydrates (e.g., with lower 30 degrees of polymerization, DP) were favored.

In particular, the carbohydrate profiles are shown (HPAEC-PAD) for the pre-inoculum and 24 Hr samples in FIG. 4. FIG. 4 illustrates overlaid HPAEC-PAD chromatograms of fermentation media containing ISOThrive™ MIMO with *B. subtilis* NRRL B-23049, at various time points of fermentation. Trace 1: pre-inoculum. Trace 2: media after 24 hr incubation. Trace 3 media after 44 hr fermentation. Trace 4: media after 72 hr fermentation. The components detected by HPAEC-PAD were: A, mannitol; B, unknown; C, L-arabinose (IS); D, glucose; E, isomaltotriose; F, isomaltotetraose; G, maltose, and H-M, PAN-type MIMO with DP 4-8. As illustrated, the lower degree of polymerization MIMO present in peak H disappears over time (compare pre-inoculum trace 1 with the 72 hr trace 4).

FIG. 5 illustrates the metabolic profile (HPLC-RID) of *B. subtilis* NRRL B-23049 during fermentation in media containing ISOThrive™ MIMO as a sole carbon source. Trace 1: Pre-inoculation media. Trace 2: media after 24 Hr fermentation. Trace 3: media after 44 Hr fermentation. Trace 4: media after 72 Hr fermentation. The components detected in the media were: A, MIMO DP >3; B, panose; C, maltose; D, leucrose; E, glucose: F, mannitol; G, lactate; H. acetate, and I. unknown diol. As illustrated, there is a decrease in MIMO (large peak at elution time 10 min) and an increase in lactate (small peak at 2.7 min elution) as time proceeds. This organism is a facultative anaerobe, but prefers the presence of oxygen. When MIMO is the carbon source, lactate and acetate metabolites were observed (e.g., no butyrate).

FIG. 6 graphically illustrates the rate of consumption by *B. subtilis* NRRL B-23049 of ISOThrive™ MIMOs with different degrees of polymerization (DP 3-7) at different time points in the fermentation. Top line: 0 hr fermentation. Second from the top line: 24 hr fermentation. Third line from the top: 44 hr fermentation. Bottom line: 72 hr fermentation. As shown in FIG. 6, MIMO was consumed at a rate of 0.103%/hr, and MIMOs with DP less than 6 were preferred substrates.

Though slow, about 50% of the tested prebiotic composition (containing ISOThrive™ MIMO (lot #160120)) was consumed by this strain of *Bacillus subtilis*. The culture was pure, and the late log morphology conformed with *Bacillus* spp., indicating that the results were due to *B. subtilis* NRRL B-23049 metabolism, and not to any contaminants.

Example 5: *Pediococcus acidilactici* NRRL B-5727 does not Grow in Media Containing Maltosyl-Isomaltooligosaccharides (MIMOs) as a Sole Carbon Source Another microorganism was found in gut microbiota of the placebo group subjects via 16S rRNA sequencing. The sequences for selected glucosidase genes that the inventors wished to interrogate (dexA and dexB: UniParc sequence #UPI00071AFA9B, checksum 91F60DC3EA289908, length 831, 93,587 Da) were interrogated by BLAST (nucleotide to protein) analysis. BLAST searches of this sequence provided no α-1,6-glucosidases that were coded by this microorganism with a certainty that exceeded 98%. Only 5 hits were obtained of any match quality. These data indicate that this organism may be a poor candidate for targeting by MIMO prebiotics. because this microorganism will not likely consume MIMO, and thus its growth will likely not be enhanced by MIMO.

However, it should be noted that the UniRef database (see website at www.uniprot.org/uniref/UniRef50_P29430) indicates that this microorganism may synthesize pediocins A, BA 28 and pre-pediocin AcH. The probiotic (man and animals, strain MA15/5M; Barreau et al. 2012, J. Bacteriol. 194 (4), pp. 901) organism *Pediococcus acidilactici* is acid stable and able to pass through the stomach intact. *Pediococcus acidilactici* strain NRRL B-5627 has been shown to synthesize pediocins (Guerra, et. al. 2005. Biotechnol. Appl. Biochem. 42 (1), pp. 17-23), and to produce pediocin SA-1, which is particularly effective against food borne pathogens including *Listeria* spp. (Anastasiodou, et al. 2008. Bioresour. Technol. 99 (13), pp. 5384-5390).

Methods

MRS (Sigma) media was prepared by dissolving 5.502 g MRS in 101.387 g (total) water (18MΩ). This media was autoclaved at 121° C. for 15 min. After cooling, the media was inoculated with *Pediococcus acidilactici* NRRL B-5727 (0.5 mL late log-phase culture frozen at −78° C. in 20% glycerol), and incubated at 35° C. for 16 Hr. This culture was the inoculum for the following fermentation.

To a 2 L fermenter (New Brunswick BioFlo/Celligen 115) was added water (18MA), 0.960 kg; peptone (meat) 10.043 g; yeast extract, 5.553 g; ISOThrive™ MIMO (lot #160120). 25.016 g; $MnSO_4$-$H_2O$, 0.01301 g; $MgSO_4$, 0.12952 g; $FeSO_4$-$7H_2O$, 0.01295 g; $KH_2PO_4$, 2.906 g; NaCl, 0.01447 g, and $CaCl_2$-$2H_2O$, 0.06088 g.

This media was autoclaved at 121° C. for 15 minutes. Once cooled to 35° C., this temperature was maintained using a recirculating water bath. The pH was adjusted to pH 6.6 with NaOH (50% w/w) and this pH was maintained throughout using NaOH (40% w/w). This culture was the inoculum for the following fermentation.

To the fermenter was aseptically added 10 mL late log-phase *Pediococcus acidilactici* NRRL B-5727 inoculum, and micro-anaerobic (self-blanketing) conditions were maintained. The fermentation was allowed to proceed for 17.75 and 42 Hr before sampling. The headspace contained 10.2% $O_2$ and 7.8% $CO_2$ (PBI Dansensor CheckMate 9900). The cells were removed via centrifugation (Sorvall RC-5B+, G3 rotor) at 13.689 g for 20 minutes. The supernatant was sampled for analysis via HPLC-RID/HPAEC-PAD and the remainder frozen at −78° C. pending analysis of bacteriocin content by mass spectrometry (target Pediocin, structural gene pedA, 4.6 kDa; MKKIEKLTEK EMANIIGGKY YGNGVTCGKH SCSVDWGKAT TCHINNGAMA WATGGHQGNH KC, SEQ ID NO:10). A small subsample of the biomass was resuspended to wash and centrifuged again (Eppendorf 5415 C) at 12 kRPM for 15 minutes. The washed (miniscule) biomass pellet was re-suspended and gram stained for confirmation of culture morphology and purity via oil-immersion microscopy.

Results

The profile for the ISOThrive™ MIMO prebiotic in the presence of *Pediococcus acidilactici* NRRL B-5727 was unchanged during the fermentation relative to the pre-inoculum media. The *Pediococcus acidilactici* NRRL B-5727 bacteria apparently consumed all of the residual glucose, fructose and maltose, and then died. The few cells that could be found, while dead (staining pink), exhibited a morphology conforming with *Pediococcus* spp. These results indicate that the ISOThrive™ MIMO prebiotic does not stimulate the growth of *Pediococcus acidilactici* NRRL B-5727.

Example 6: *Pediococcus acidilactici* NRRL B-5727 Growth in Media Containing Prebiotin™ FOS Enriched Inulin The inventors decided to do further BLAST analyses to look for levA and fruA (both transporters), as well as 1-FEH (fructan-p-(2,1)-fructosidase, inulin type), and 6-FEH (fructan-V1(2,6)-fructosidase, kestose or FOS type) proteins. The full list of known genes for fructosidase activities are given in the Kegg database (see website at www.genome.jp/dbget-bin/www_bget?ec:3.2.1.80). The organism should consume fructan, β-(2,6), in particular, so a fermentation was conducted using a prebiotic FOS composition containing both β-(2,1) (inulin), and β-(2,6) (kestose/levan type) fructans.

Methods

MRS (Sigma) media was prepared by dissolving 5.575 g MRS in 99.970 g (total) water (18M1). The media was autoclaved at 121° C. for 15 min. The media was inoculated with *Pediococcus acidilactici* NRRL B-5727 (0.5 mL late log-phase culture frozen at −78° C. in 20% glycerol), and incubated at 35° C. for 16 Hr. This culture was the inoculum for the following fermentation.

To a 2 L fermenter (New Brunswick BioFlo/Celligen 115) was added water (18M12). 0.960 kg: peptone (meat) 10.006 g; yeast extract. 5.649 g; Prebiotin™ FOS enriched inulin (lot #160120). 25.043 g; $MnSO_4$—$H_2O$, 0.01236 g; $MgSO_4$, 0.12790 g; $FeSO_4$-$7H_2O$, 0.01235 g; $KH_2PO_4$, 2.924 g; NaCl, 0.01207 g, and $CaCl_2$-$2H_2O$, 0.06104 g. The whole was autoclaved at 121° C. for 15 minutes. Once cooled to 35° C., this temperature was maintained using a recirculating water bath. The pH was adjusted to pH 6.6 with NaOH (50% w/w) and this pH was maintained throughout using NaOH (40% w/w). To the fermenter was aseptically added 20 ml., late log-phase *Pediococcus acidilactici* NRRL B-5727 inoculum, and micro-anaerobic (self-blanketing) conditions were maintained. The fermentation was allowed to proceed for 17 and 42 Hr before sampling. The headspace contained 9.89% $O_2$ and 9.0% $CO_2$ (PBI Dansensor CheckMate 9900). The cells were removed via centrifugation (Sorvall RC-5B+, G3 rotor) at 13.689 g for 20 minutes. The supernatant was sampled for analysis via HPLC-RID/HPAEC-PAD and the remainder frozen at −78° C. pending analysis of bacteriocin (target pediocin) content by mass spectrometry. A small subsample of the biomass was resuspended to wash and centrifuged again (Eppendorf 5415 C) at 12 kRPM for 15 minutes. The washed (miniscule) biomass pellet was re-suspended and gram stained for confirmation of culture morphology and purity via oil-immersion microscopy. At 17 Hr all of the DP 3 (kestose) had been consumed.

Example 7: *Lactobacillus plantarum* NRRL-B-4496Growth in Media Containing ISOThrive™ MIMO This Example illustrates that *Lactobacillus plantarum* NRRL-B4496 grows in media fortified with ISOThrive™ MIMO. Analysis of the genomic data and subsequent reference for the DexA gene indicated that the organism had a PrbI of 30 for oligo-alpha-1,6-glucosidase, alone indicating that the organism was likely to be able to utilize MIMO as a sole carbon source.

Methods

MRS (Sigma) media was prepared by dissolving 5.540 g MRS broth in 99.791 g (total) water (18MΩ). The media was autoclaved at 121° C. for 15 min. After cooling, the media was inoculated with *Lactobacillus plantarum* NRRL-B-4496 (0.5 mL late log-phase culture frozen at −78° C. in 20% glycerol), and incubated at 35° C. for 16 Hr. This culture was the inoculum for the following fermentation.

To a 2 L fermenter (New Brunswick BioFlo/Celligen 115) was added water (18MΩ), 0.960 kg; peptone (meat) 10.027 g; yeast extract. 5.541 g; ISOThrive™ MIMO (lot #160120), 25.116 g; $MnSO_4$-$H_2O$, 0.01297 g; $MgSO_4$, 0.12796 g; $FeSO_4$-$7H_2O$, 0.01366 g; $KH_2PO_4$, 2.93590 g; NaCl, 0.01355 g, and $CaCl_2$-$2H_2O$, 0.06377 g. The media was autoclaved at 121° C. for 15 minutes. Once cooled to 35° C., this temperature was maintained using a recirculating water bath. The pH was adjusted to pH 6.6 with NaOH (50% w/w) and this pH was maintained throughout using NaOH (40% w/w).

To the ferementer was aseptically added 20 mL late log-phase *Lactobacillus plantarum* NRRL-B-4496 inoculum, and micro-anaerobic (self-blanketing) conditions were maintained. The fermentation was allowed to proceed for 34 Hr before sampling. The headspace contained 8.4% $O_2$ and 5.7% $CO_2$ (PBI Dansensor CheckMate 9900). The cells were removed via centrifugation (Sorvall RC-5B+, 03 rotor) at 13,689 g for 20 minutes. The supernatant was sampled for analysis via HPLC-RID/HPAEC-PAD and the remainder frozen at −78° C. pending analysis of bacteriocin content by mass spectrometry. The target was plantaricin M and Z, 6.7956 and 7.1922 kDa (see. Amina et al., Int J Biol Chem 9: 46-58 (2015)). A small subsample of the biomass was resuspended to wash and centrifuged again (Eppendorf 5415 C) at 12 kRPM for 15 minutes. The washed biomass pellet was re-suspended and gram stained for confirmation of culture morphology and purity via oil-immersion microscopy.

Results

Figure 7:
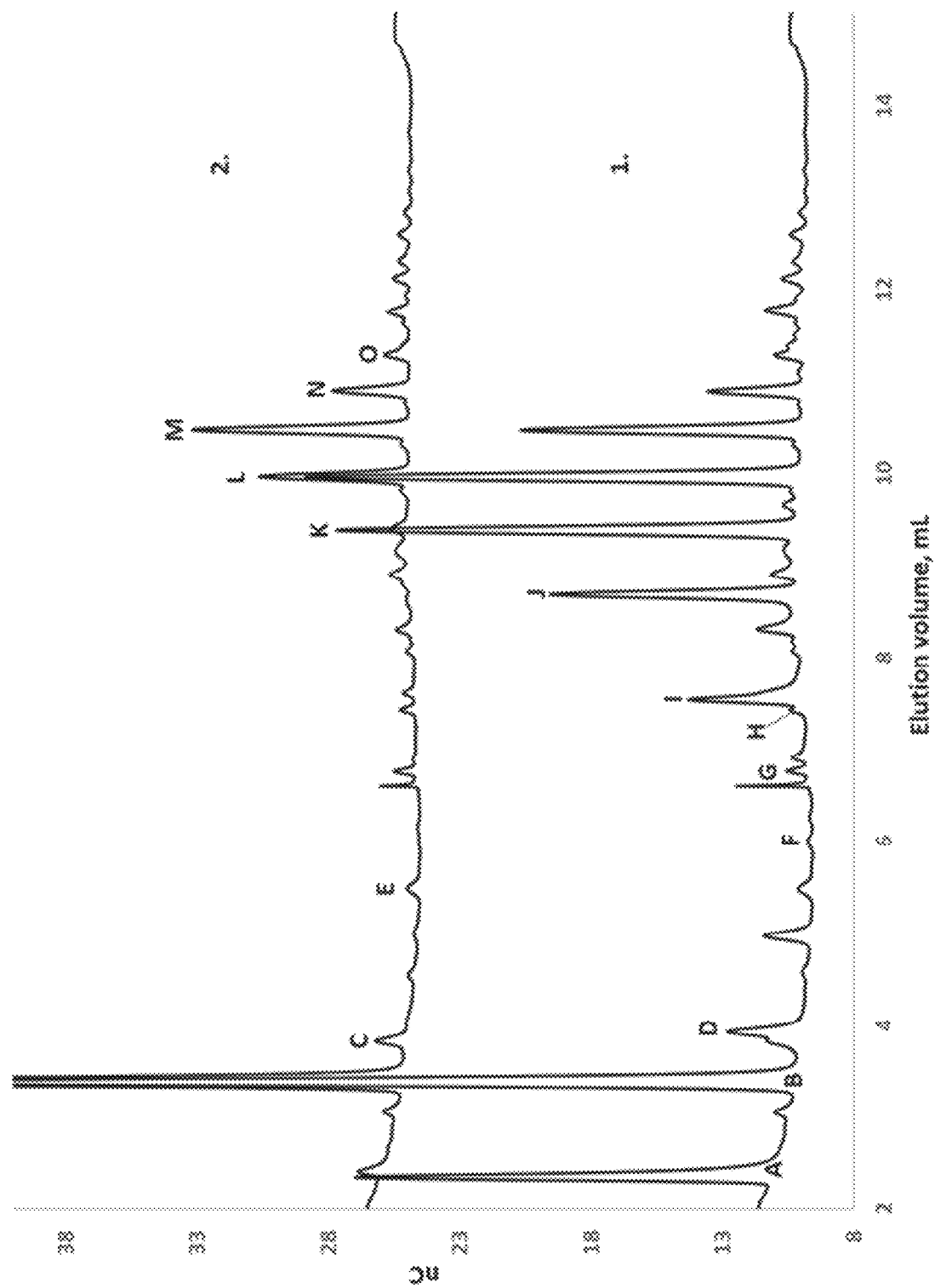
FIG. 7 illustrates overlaid HPAEC-PAD chromatograms of fermentation media containing ISOThrive™ MIMO with *L. plantarum* NRRL B-4496. Trace 1: pre-inoculation media. Trace 2: media after 34 hr fermentation. The components detected in the media were A, mannitol; B, L-arabinose (IS); C, unknown; D, glucose; E, leucrose; F, isomaltose; G, isomaltotriose; H. isomaltotetraose; I, maltose, and J-O, PAN-type MIMO DP 3-8.

Most of the tested prebiotic ISOThrive™ MIMO composition had been consumed by 34 hours after inoculation with *Lactobacillus plantarum* NRRL-B-4496: 67.2% of the MIMO had been consumed and the remaining material was DP >4 (compare pre-inoculation media Trace 1 with the 34 Hr fermentation media Trace 2 in FIG. 7). In particular, the carbohydrate profiles of media are shown (HPAEC-PAD) in FIG. 7 for the pre-inoculum media and a sample of media taken after 34 Hr fermentation. The components detected in the media were A. mannitol; B, L-arabinose (IS); C, unknown: D, glucose; E, leucrose; F, isomaltose; G, isomaltotriose; H, isomaltotetraose; I, maltose, and J-O, PAN-type MIMO with DP 3-8. As illustrated, most of the maltose (I), and lower DP MIMOs (e.g., peaks J and K) disappear by 34 Hr. fermentation.

Further analysis showed that the culture was pure and late log phase bacteria had morphology conforming to *Lactobacillus* spp.

Figure 8:
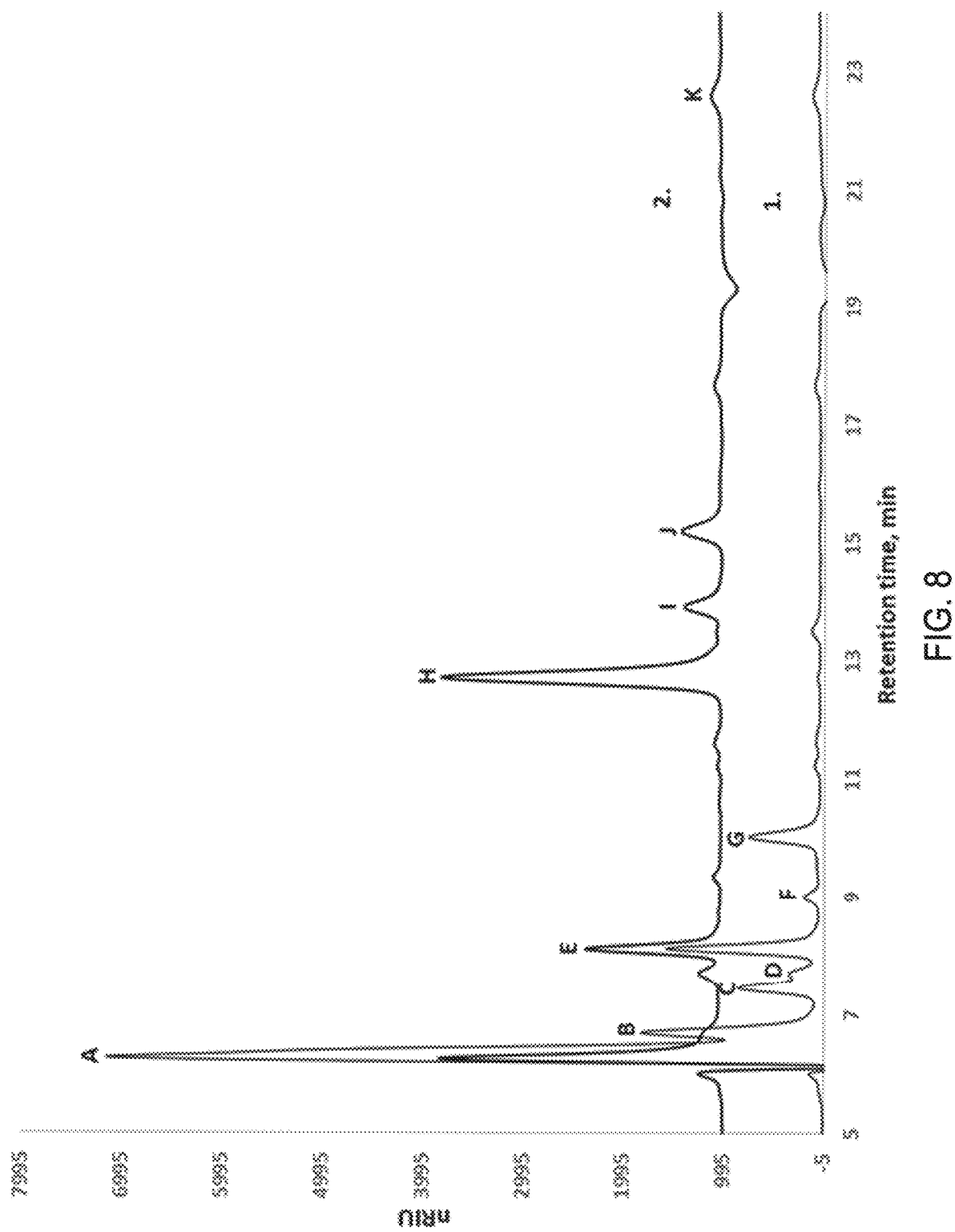
FIG. 8 illustrates the metabolic products (as detected by HPLC-RID) of *L. plantarum* NRRL B-4496 when ISOThrive™ MIMO is a sole carbon source. Trace 1: Pre-inoculation media. Trace 2: media after 34 Hr fermentation. The components detected were: A, MIMO DP>3; B, panose; C, maltose; D, leucrose; E, unknown acid from media; F, glucose; G, mannitol; H, lactate; I, formate; J, acetate, and K, ethanol.

When ISOThrive™ MIMO was the carbon source, pyruvate metabolism was observed, where primarily lactate and traces of formate, acetate, and ethanol were produced (FIG. 8). In particular, FIG. 8 illustrates the metabolic products (as detected by HPLC-RID) of *L. plantarum* NRRL B-4496 when ISOThrive™ MIMO is a sole carbon source. Trace 1: Pre-inoculation media. Trace 2: media after 34 Hr fermentation. The components detected were: A, MIMO DP >3: B, panose: C, maltose: D, leucrose; E, unknown acid from media; F, glucose; G, mannitol; H, lactate: I, formate; J, acetate, and K, ethanol. As illustrated, the pre-inoculation media (Trace 1) has little or no lactate (peak H), formate (peak I) or acetate (peak J). But significant amounts of lactate (peak H), formate (peak I) or acetate (peak J) are detected after 34 Hr fermentation of ISOThrive™ MIMO by *Lactobacillus plantarum* NRRL-B-4496.

Example 8: Effects of Probiotic-Conditioned Media on Head & Neck Cancer Cells

This Example shows that media from growth of *Lactobacillus gasseri* or *Lactococcus lactis* can affect the morphology and growth of head and neck squamous cell carcinoma (HNSCC) cells.

Methods

Overnight cultured head and neck squamous cell carcinoma (HNSCC) cells (HSC-3 and 14A cells; 70-80% confluency) were treated with different concentrations (25, 50, 100, 150, 200 and 300 mg/ml; BCA protein assay) of broth obtained from *Lactobacillus gasseri* ATCC 4%2 or *Lactococcus lactis* subsp. *lactis* NRRL B-1821 bacteria for 2 hours. After 2 hours the media was removed and replaced with regular medium and the carcinoma cells were then cultured for another 12 hours. No bacterial contamination or precipitation of the cancer cell media was observed during the incubation.

Results

Cell growth inhibition and morphological changes were induced by *Lactobacillus gasseri* and *Lactococcus lactis* in squamous cell carcinoma HSC-3 cells in a dose-dependent manner. Slight induction of morphological changes in the squamous cell carcinoma 14A cells were also observed. These preliminary results indicate that broth from *Lactobacillus gasseri* may be a more effective inhibitor of head and neck squamous cell carcinoma cell growth than broth from *Lactococcus lactis*.

These results also show that cancer cells can be treated with conditioned media continuously for 12-18 hours (overnight).

Example 9: Probiotic-Conditioned Media Inhibits Colon Cancer Cell Growth

This Example illustrates that culture medium obtained after growth of *Lactobacillus gasseri* ATCC 4962 or *Lactococcus lactis* subsp. *lactis* NRRL B-1821 can inhibit colon cancer cell growth.

Cells

HCT-15 (ATCC CCL-225) and DLD-1 (ATCC CCL-221) colon cancer cells were purchased from the American Type Tissue Collection (Manassas. Va.) and maintained in ATTC-modified RPMI-1640 medium (Gibco. Gaithersburg, Md.) supplemented with 10% fetal bovine serum and 1% penicillin/streptomycin. HCT-15 cells are human colonic epithelium, adherent, Dukes' type C colorectal cancer cells. DLD-1 cells are human colonic epithelium, adherent, Dukes' type C colorectal cancer cells differentiated from HCT-15 and originating from chromosomal aberrations within the HCT-15 parent cell line.

Cell Proliferation Assay

Growth of HCT-15 and DLD-1 colorectal cancer cells was examined during exposure to media obtained after growth of *Lactobacillus gasseri* ATCC 4962 or *Lactococcus lactis* subsp. *lactis* NRRL B-1821.

HCT-15 and DLD-1 colorectal cancer cells were incubated for 24 hours with control media or cell-free broth from *Lactobacillus gasseri* ATCC 4962 or *Lactococcus lactis* subsp. *lactis* NRRL B-1821 cultures (100, 200, 400 or 800 g/mL). To determine the effect of broth from *Lactobacillus gasseri* ATCC 4962 or *Lactococcus lactis* subsp. *lactis* NRRL B-1821 cultures on cancer cell proliferation, the CyQUANT NF Cell Proliferation Assay Kit was used according to manufacturer's instructions (Invitrogen/Life Technologies, Grand Island, N.Y.).

In another series of experiments. the effect of nisin ZP or conditioned media from *Lactococcus lactis* or *Lactobacillus gasseri* (*Lc. lactis* or *L. gasseri*) on HCT-15 and DLD-1 colorectal cancer cell proliferation was determined using a CyQUANT NF Cell Proliferation Assay Kit according to manufacturer's instructions (see website at tools.thermofisher.com/content/sfs/manuals/mp35006.pdf). Briefly, 10000 HCT-15 or DLD-1 cells were seeded in a 96-well microplate. Following incubation overnight, and growth to 70-80% confluence, cells were exposed to either nisin Z (0-800 µg/mL: 0.00-160 µg peptide/well), nisin A (0-400 mg/mL; 0.00-80.0 µg/well), or conditioned media from either *Lactococcus lactis* or *Lactobacillus gasseri* for 24 hr (concentration normalized over total BCA protein content to 0-800 µg/mL).

In another experiment, the HCT-15 or DLD-1 cells were exposed to conditioned challenger media from *Lactococcus lactis* or *Lactobacillus gasseri* incubated with *W. viridescens* NRRL B-1951 challenger cells. After incubation with such challenger media, the cell culture media was removed from cells by gentle aspiration. The HCT-15 or DLD-1 cells were stained with CyQUANT NF (Invitrogen/Life Technologies, Grand Island, N.Y.) dye reagent (SYBR® Green I/DMSO) and incubated at 37° C. for 20 min. Fluorescence intensity was measured using fluorescence microplate reader with excitation at 485 nm and emission detection at 530 nm (Spectra max M2, Molecular Devices. Sunnyvale, Calif.). Experiments were performed in triplicate.

Results

Figure 9A:
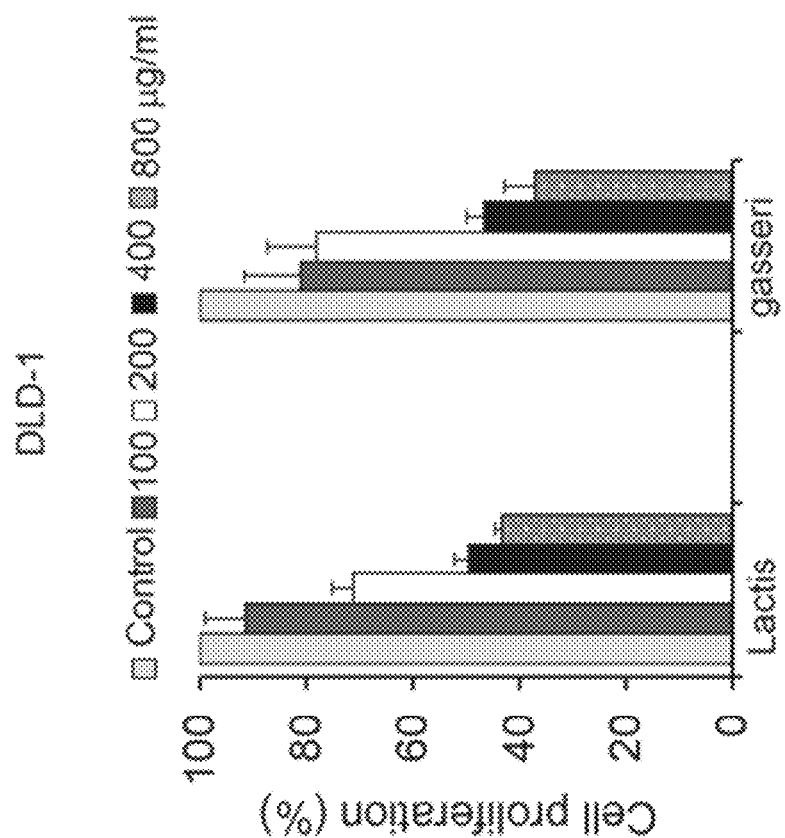
FIG. 9A-9E graphically illustrate inhibition of colon cancer cell growth by media obtained from culture of *Lactococcus lactis* and *Lactobacillus gasseri* using a CyQUANT NF cell proliferation assay. Dosing was 0 (control), 100, 200, 400, and 800 µg/mL equivalent protein (BCA assay) in both cases.
Figure 9B:
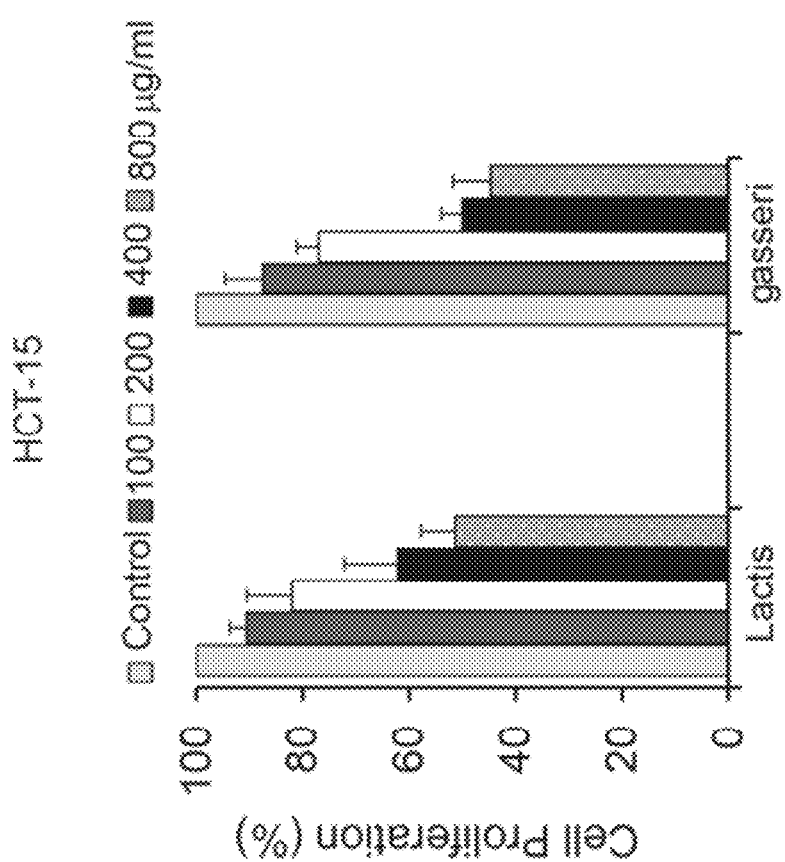
Figure 9C:
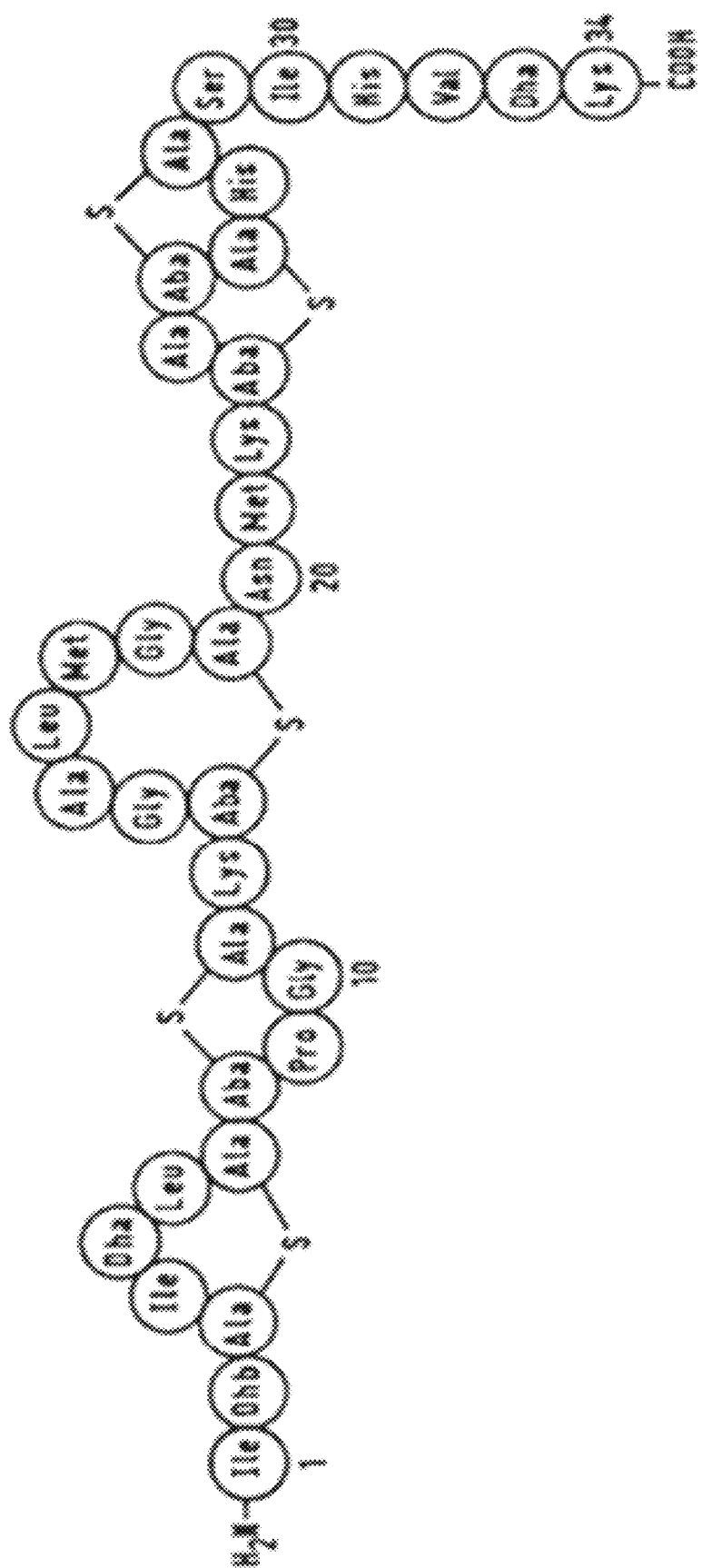
Figure 9D:
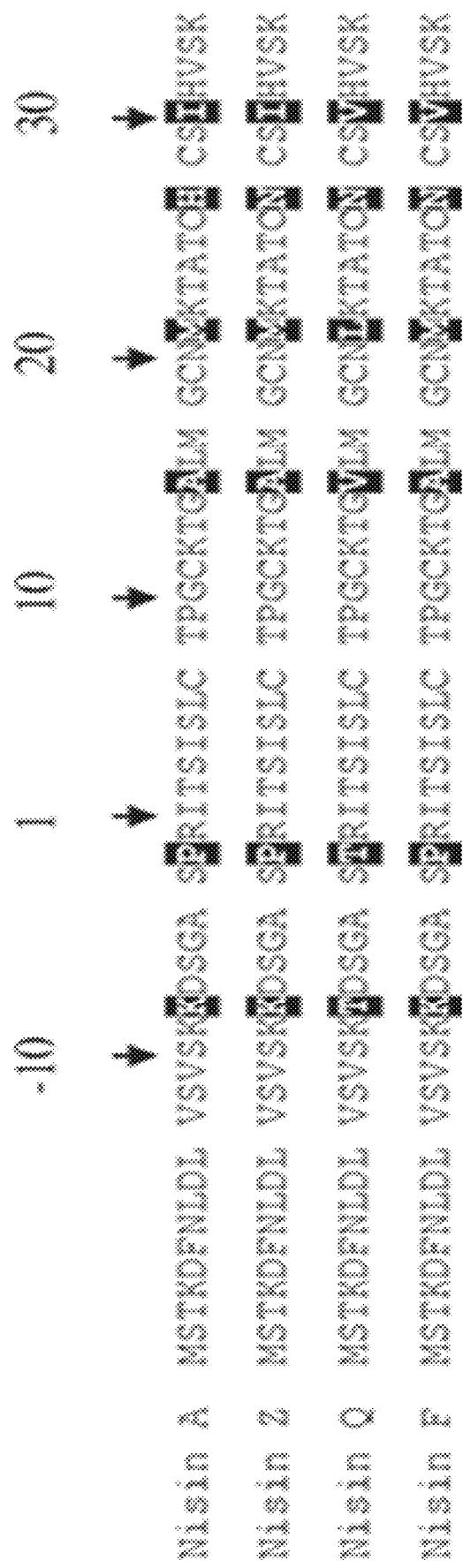

As illustrated in FIG. 9A-9B, broth from *Lactobacillus gasseri* and *Lactococcus lactis* cultures reduced colon cancer cell proliferation in a dose-dependent manner relative to control culture media. These data indicate that *Lactobacillus gasseri* and *Lactococcus lactis* secrete a substance that inhibits cancer cell growth.

Figure 9E:
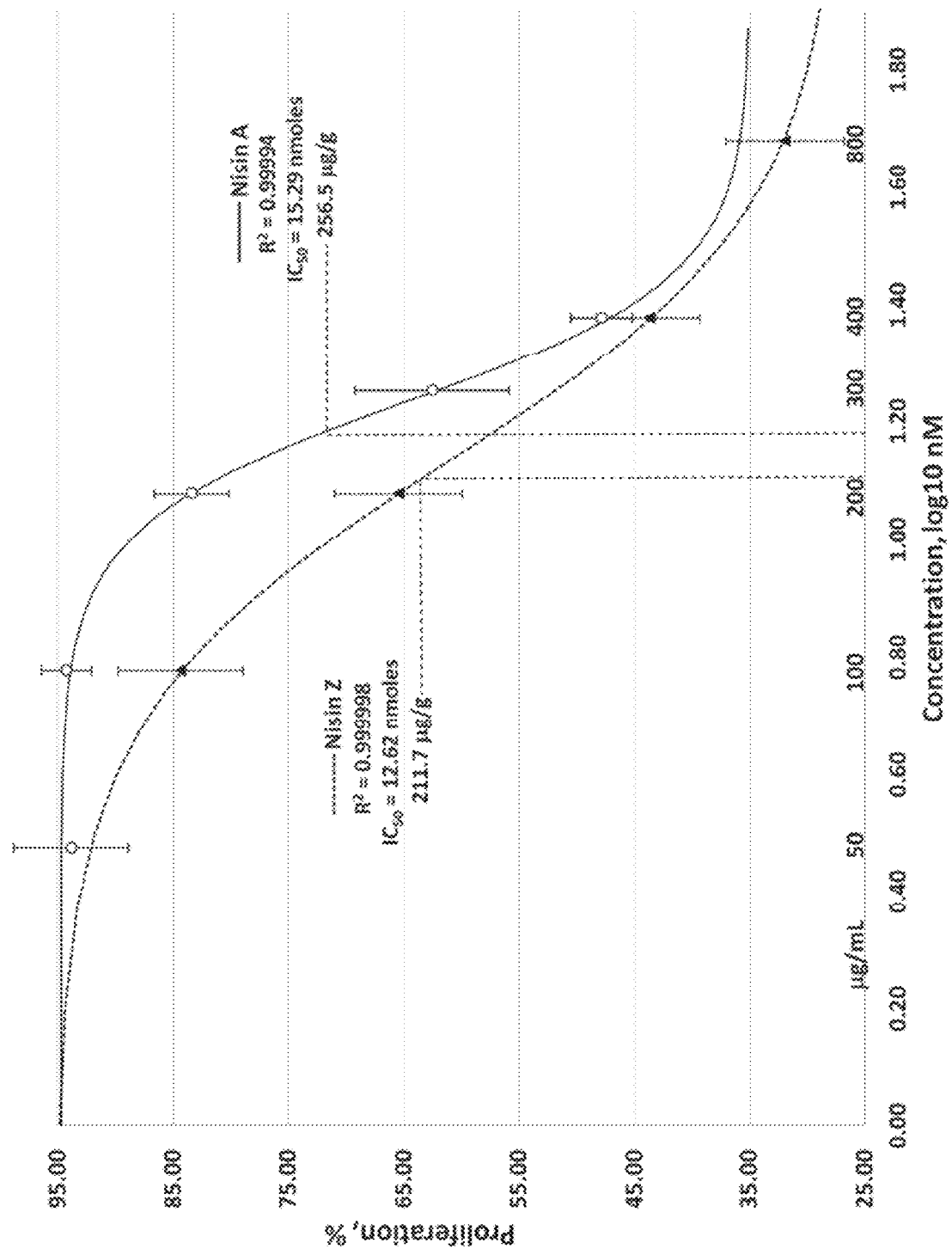

FIG. 9E graphically illustrates that Nisin Z demonstrated similar antiproliferative behavior when applied to either DLD-1 or HCT-15 colorectal cancer cell lines. Unlike the *W. viridescens* bacteria (see Example 10), these cancer cells did not exhibit bimodal behavior with respect to nisin dose. As shown in FIG. 9E, the average $IC_{50}$ (N=4×3) of Nisin Z was 211.7±10.82 µg/g (12.62 nmoles). The relationship (ratio of µg agent in each sample) between the Nisin Z bacterial $MIC_{50}$ and the $IC_{50}$ was ~3.21:1. Nisin A also demonstrated similar potency vs. DLD-1 and HCT-15 CRACs, but was less potent than nisin Z. The average $IC_{50}$ 256.5±10.11 µg/g (15.29 nmoles) and the relationship between bacterial $MIC_{50}$ and $IC_{50}$ was ~3.89:1.

Test broths from *Lactococcus lactis* or *Lactobacillus gasseri* demonstrated dose-dependent antiproliferative activity vs. HCT-15 and DLD-1 cells (FIG. 10A-10D, with pure nisin Z for reference). At the highest concentrations tested, base broths from *Lactococcus lactis* or *Lactobacillus gasseri* cultures performed similarly against both cell lines. but broth from *Lactococcus lactis* subsp. *lactis* NRRL B-1821 (2.26 µg/g nisin-equivalent activity) was slightly more potent than that from *Lactobacillus gasseri* ATCC 4962, where the observed antiproliferative effects were −49.00±0.94 and −45.50±0.24% of growth. respectively.

Figure 10A:
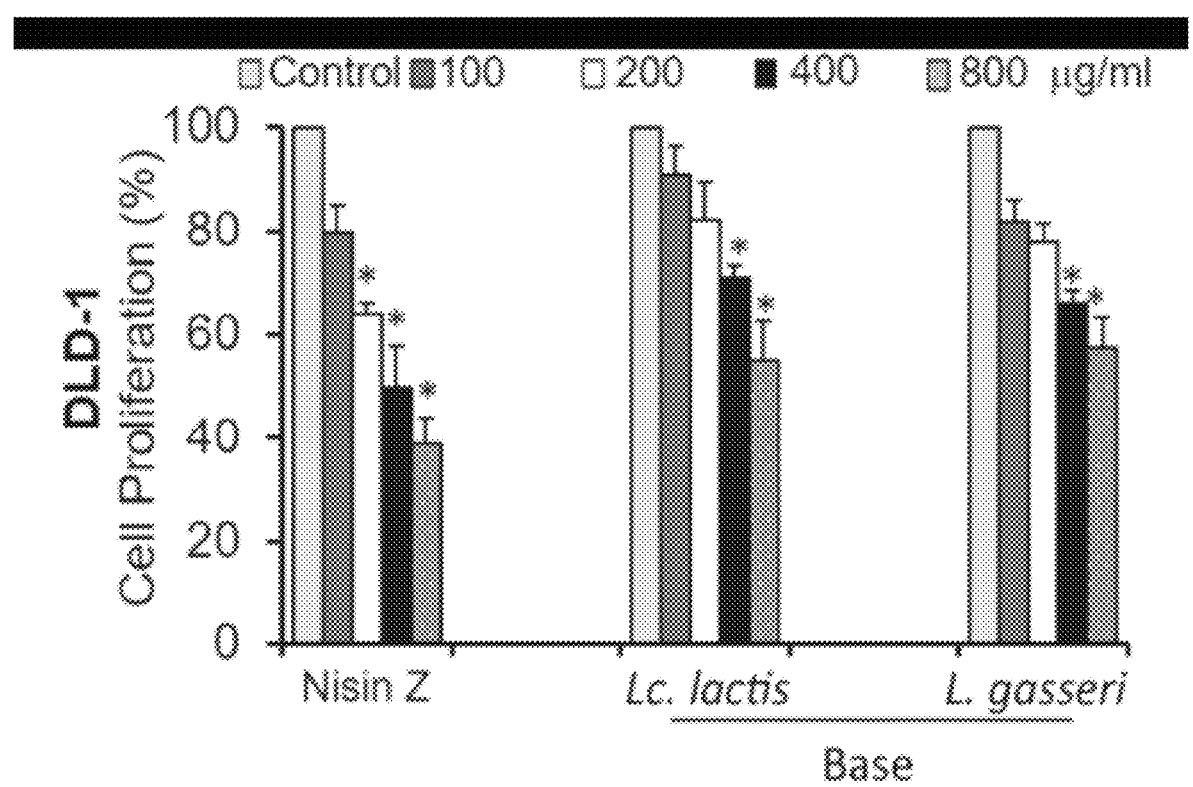
FIG. 10A-10F graphically illustrate that DLD-1 (A, B) and HCT-15 (C. D) colorectal cancer cell are inhibited by nisin Z produced by *Lactococcus lactis* and *Lactobacillus gasseri* cells produced with and without challenge by *W. viridescens* NRRL B-1951.
Figure 10B:
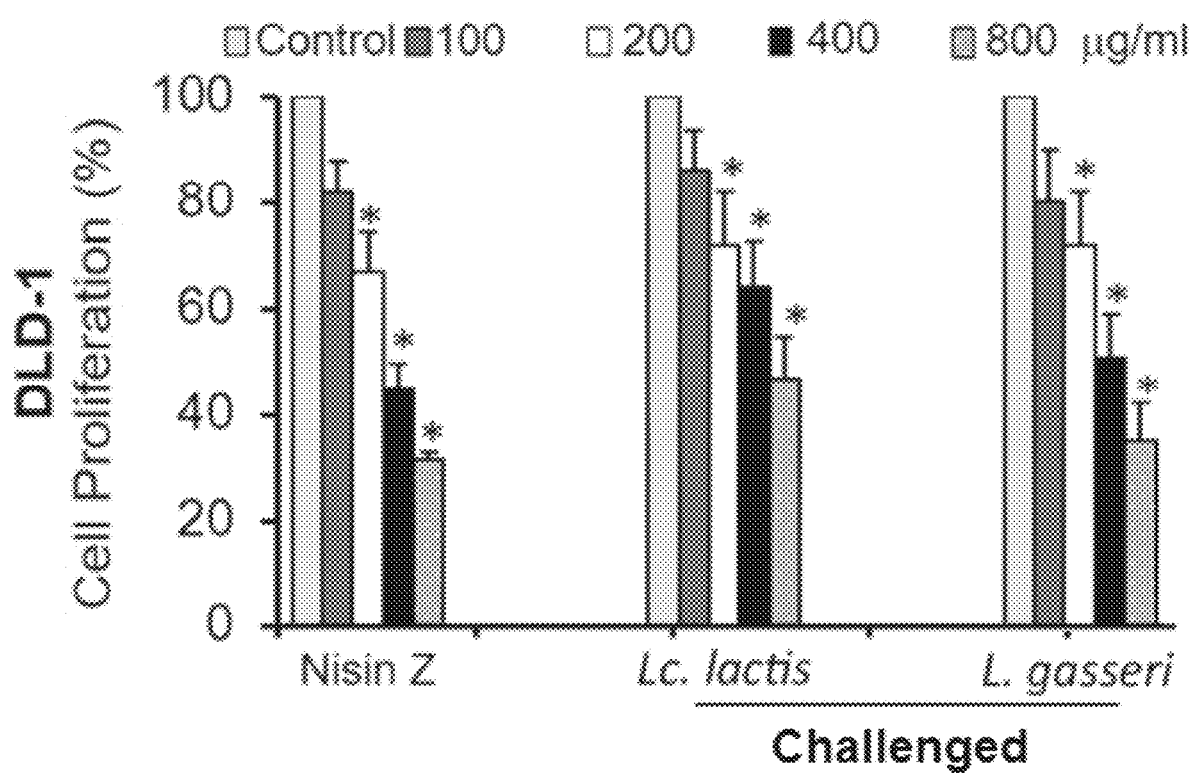
Figure 10C:
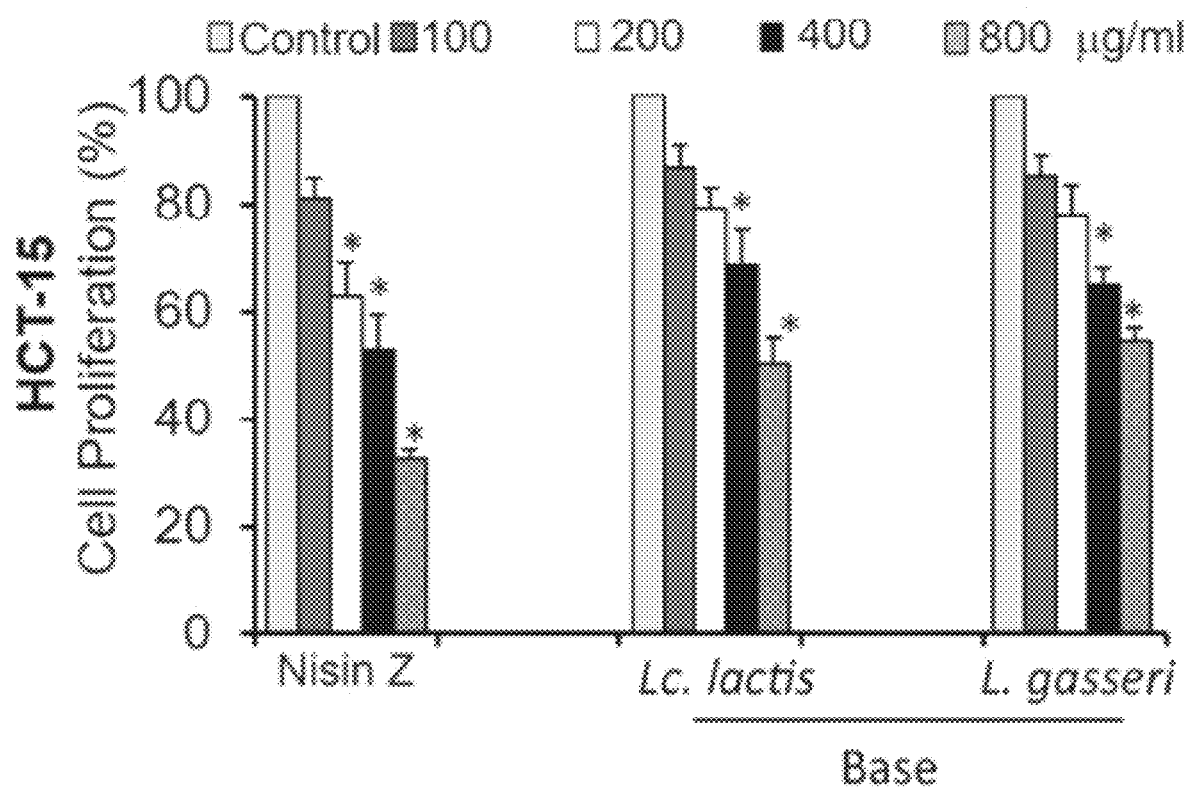
Figure 10D:
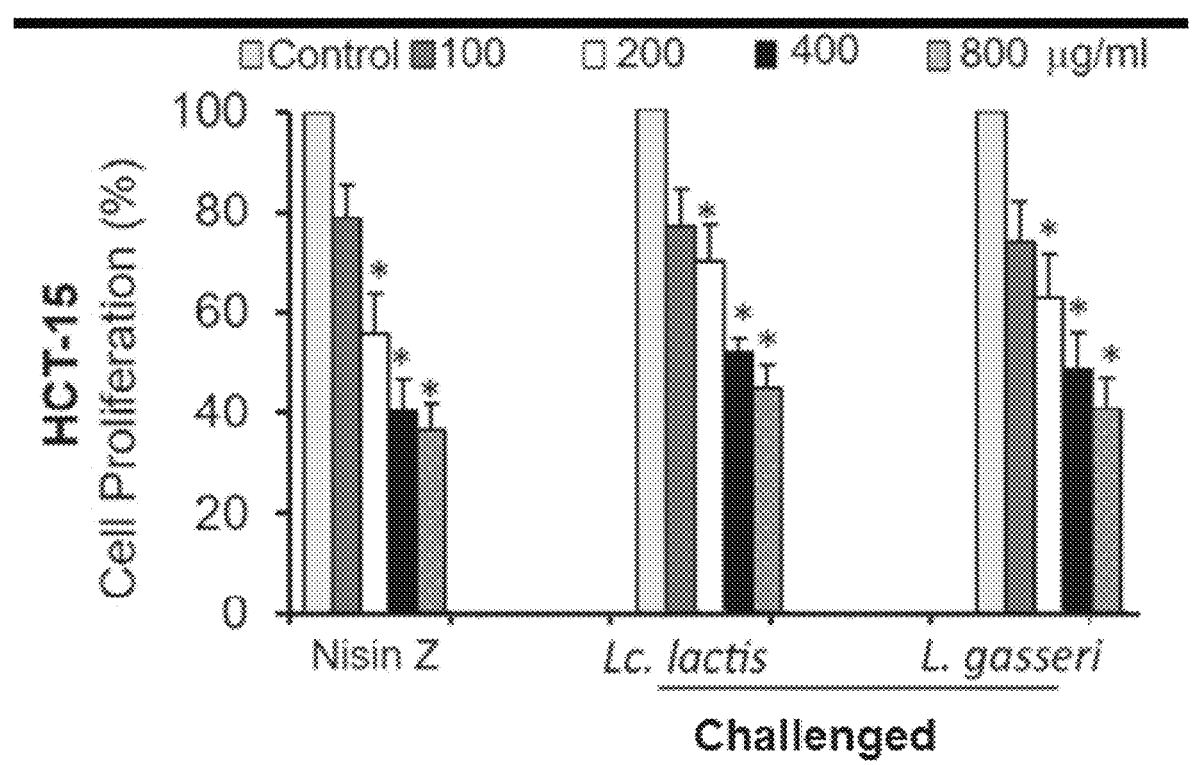
Figure 10E:
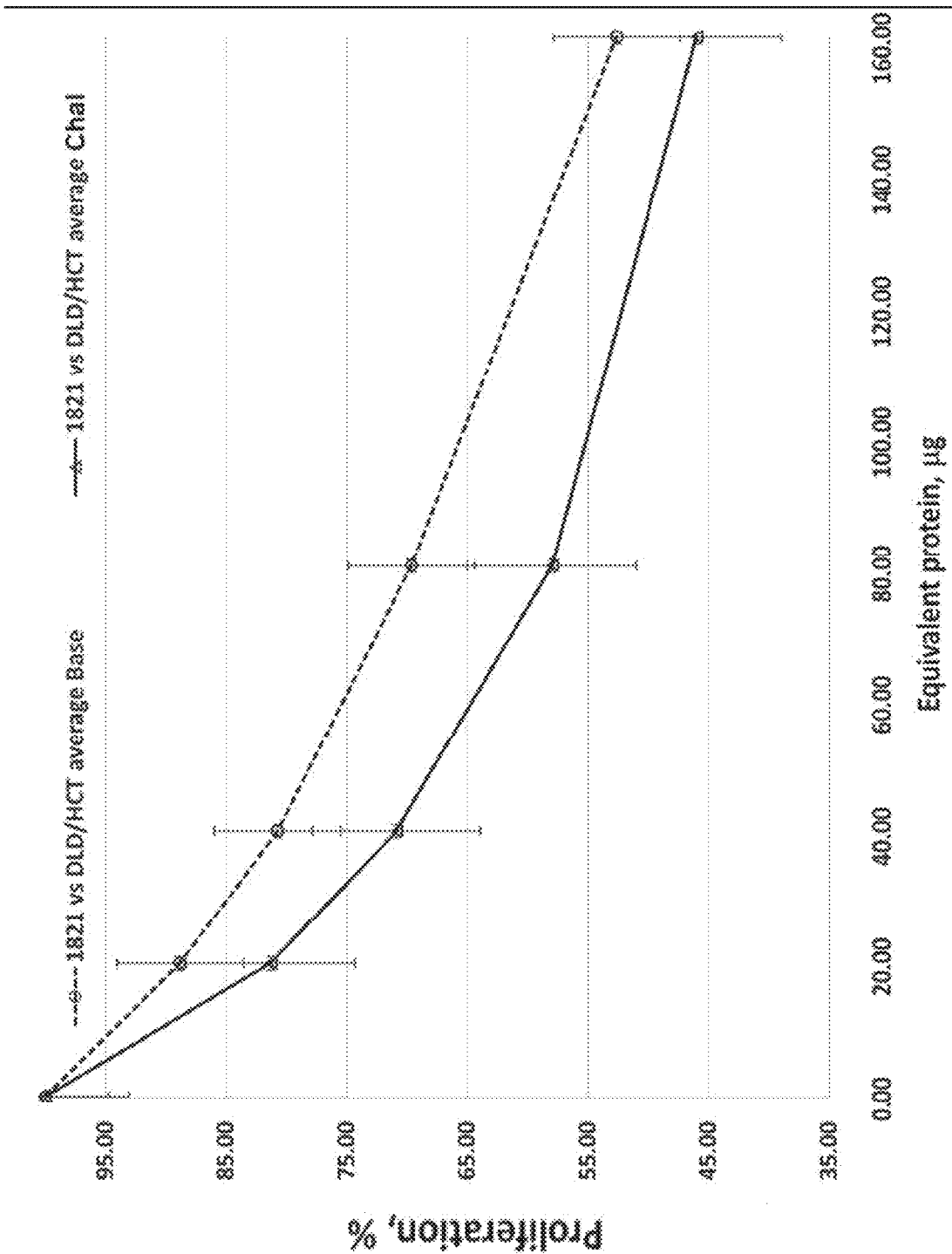
Figure 10F:
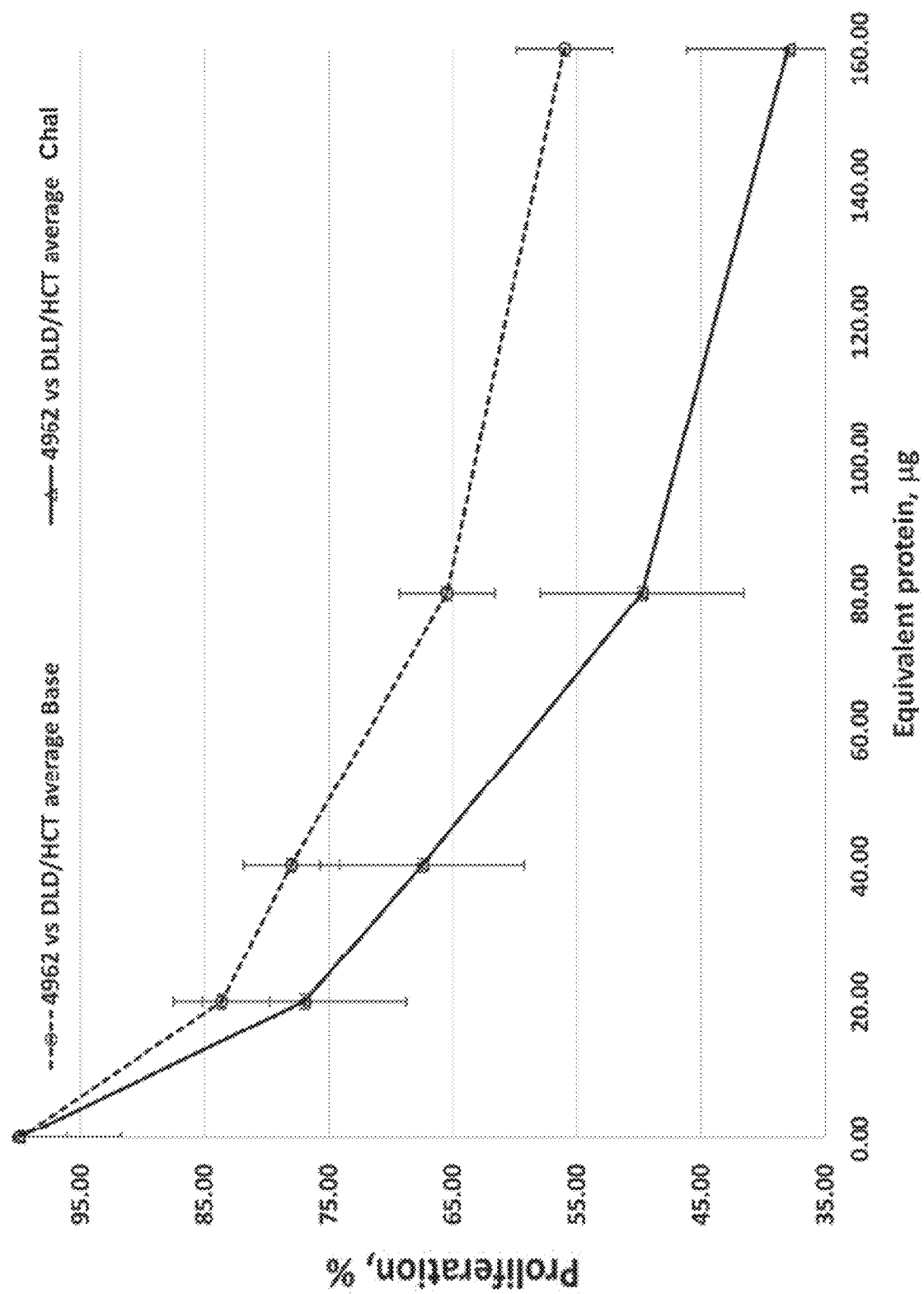

Both *W. viridescens* NRRL B-1951 challenged broths out-performed their base-counterparts (FIG. 10E-10F). Broth from *Lactococcus lactis* B-1821 challenged with *W. viridescens* demonstrated potent inhibition of both HCT-15 and DLD-1 cell lines, with a decrease of 53.50±1.18% HCT-15 and DLD-1 cell growth. Broth from *Lactobacillus gasseri* ATCC-4962 challenged with *W. viridescens* was even more effective against both HCT-15 and DLD-1 cell lines with an inhibitory activity of −61.17 t 3.06% cell growth.

Example 10: Nisin a and Z Inhibit *Weissella viridescens* Growth

This Example illustrates that *Weissella viridescens* growth is inhibited by nisins A and Z.

Materials and Methods

Purified nisin A and Z are commercially available and were acquired from Handary S. A. (Brussels Belgium). Certificates of analysis For each lot indicated purities of 95.2 and 99.6% for A and Z, respectively.

100 g De-Man, Rogosa and Sharpe (MRS) media was prepared in a 500 mL Erlenmeyer to contain 5.5% solids in deionized water (18.2 MΩ, Hydro Service and Supplies. Gaithersburg, Md.). The media was autoclaved (121° C. 15 min), cooled, and inoculated with 1 mL (0.5 mL culture+0.5 mL glycerol, 40%; frozen at −78° C.) of *Weissella viridescens* NRRL B-1951 (test strain). The culture was incubated at 31° C. overnight (15 Hr).

The next day, stock solutions of either nisin A *or* Z were prepared in deionized water to contain 31.3 and 33.7 µg/g of each peptide.

100 g MRS media was prepared to contain 5.5% solids. Two sets (one set each for nisin A and nisin Z) of eight Hach-type tubes (Kimble Chase 45066-16100) were prepared. Within each set, in order was added 5.00, 4.95, 4.90, 4.75, 4.50, 4.00, 3.50 and 3.00 g MRS media. The tubes were sealed and autoclaved.

To each tube was added, of the appropriate nisin stock, 0.00, 0.05, 0.10, 0.25, 0.50, 1.00, 1.50, and 2.00 g. Each tube was inoculated with 0.25 g of late-log *W. viridescens* NRRL B-1951 culture. The tubes were sealed and the absorbance at 600 nm was quickly measured (Hach DR900). The tubes were segregated by set and incubated at 31° C. overnight (15 Hr).

Each tube was thoroughly mixed to suspend settled cells and the absorbance was measured again at 600 nm. The final absorbance values for each sample were corrected for their respective background (taken just after inoculation, scattered light from added cells). The corrected absorption values were a measure of *W. viridescens* growth.

Each tube was sampled (1.5 mL conical polypropylene centrifuge tubes) and centrifuged at 10 kRPM for 10 minutes to remove and suspended cells. The resulting supernatants were filtered (0.2 µm nylon), diluted to 0.5% solids, and analyzed by high pressure liquid chromatography (HPLC, Agilent 1100, refractive index detector and BioRad Ainex HPX-87H column) for consumption of glucose and production of organic acids. Table 9 illustrates the concentration of sugars such as glucose and production of organic acids.

Note that the MRS media originally contained 7% acetate; therefore 7% should be subtracted from the values for acetate in Table 8 to ascertain the amount of acetate generated during the assay.

TABLE 8

Concentration of Sugars and Organic Acids in the Fermentation Media

| %/brix | A1 | A2 | A4 | A5 | A6 | A7 | A8 |
|---|---|---|---|---|---|---|---|
| Maltotriose | 0.401 | 0.312 | 0.298 | 0.276 | 0.288 | 0.419 | 0.305 |
| maltose | 1.078 | 0.581 | 0.815 | 0.598 | 0.941 | 0.775 | 0.739 |
| glucose | 8.883 | 23.122 | 24.138 | 24.698 | 25.304 | 25.444 | 25.537 |
| fructose | 1.122 | 0.000 | 0.000 | 0.000 | 0.000 | 0.000 | 0.000 |
| lactic acid | 18.404 | 6.884 | 5.496 | 4.672 | 2.707 | 1.521 | 1.579 |
| glycerol | 0.386 | 0.292 | 0.319 | 0.350 | 0.328 | 0.299 | 0.301 |
| formic acid | 0.302 | 0.263 | 0.282 | 0.407 | 0.280 | 0.234 | 0.233 |
| acetic acid | 10.267 | 7.967 | 8.219 | 8.296 | 8.143 | 7.899 | 8.091 |
| ethanol | 3.979 | 0.068 | 0.062 | 0.094 | 0.057 | 0.055 | 0.071 |

| %/brix | Z1 | Z2 | Z4 | Z5 | Z6 | Z7 | Z8 |
|---|---|---|---|---|---|---|---|
| Maltotriose | 0.406 | 0.282 | 0.265 | 0.311 | 0.247 | 0.291 | 0.318 |
| maltose | 0.810 | 0.722 | 1.007 | 0.750 | 0.726 | 0.895 | 0.876 |
| glucose | 10.064 | 22.988 | 24.153 | 24.698 | 25.353 | 25.501 | 25.740 |
| fructose | 0.000 | 0.000 | 0.000 | 0.000 | 0.000 | 0.000 | 0.000 |
| lactic acid | 17.820 | 6.742 | 5.081 | 2.995 | 1.351 | 1.431 | 1.652 |
| glycerol | 0.404 | 0.343 | 0.337 | 0.321 | 0.320 | 0.335 | 0.346 |
| formic acid | 0.331 | 0.303 | 0.309 | 0.281 | 0.267 | 0.263 | 0.299 |
| acetic acid | 10.399 | 8.273 | 8.247 | 8.026 | 7.969 | 8.026 | 8.261 |
| ethanol | 3.783 | 0.057 | 0.083 | 0.067 | 0.059 | 0.065 | 0.148 |

As indicated above, the absorbance of the culture was measured again at 600 nm as a measure of *W. viridescens* growth, and the absorbance values for each sample were corrected for their respective background. These corrected absorption values plotted against nisin concentration and minimum inhibiting concentration approximated via regression. Exemplary absorbance results are provided in Table 9 below.

TABLE 8

*W. viridescens* Culture Absorbance (600 nm)

| Tube #: | MRS, g: | Test med., g: | inoc, g: | gtot: | Nisin, µg/g: | 91416 ABS 610i: | 91516 ABS 610f: | Corrected ABS 610rs: |
|---|---|---|---|---|---|---|---|---|
| A1 | 5.05046 | 0.00000 | 0.24848 | 5.29894 | 0.00 | 0.465 | 2.333 | 1.868 |
| A2 | 4.96543 | 0.05497 | 0.24044 | 5.26084 | 0.33 | 0.462 | 1.568 | 1.106 |
| A3 | 4.88322 | 0.11358 | 0.25644 | 5.25324 | 0.68 | 0.468 | 1.531 | 1.063 |

TABLE 8-continued

W. viridescens Culture Absorbance (600 nm)

| Tube #: | MRS, g: | Test med., g: | inoc, g: | gtot: | Nisin, µg/g: | 91416 ABS 610i: | 91516 ABS 610f: | Corrected ABS 610rs: |
|---|---|---|---|---|---|---|---|---|
| A4 | 4.75224 | 0.23120 | 0.26348 | 5.24692 | 1.38 | 0.466 | 1.334 | 0.868 |
| A5 | 4.52863 | 0.52264 | 0.2531 | 5.30437 | 3.08 | 0.438 | 0.911 | 0.473 |
| A6 | 4.01513 | 1.00698 | 0.24562 | 5.26773 | 5.97 | 0.42 | 0.536 | 0.116 |
| A7 | 3.50321 | 1.4864 | 0.24991 | 5.23952 | 8.86 | 0.402 | 0.403 | 0.001 |
| A8 | 3.01078 | 1.99641 | 0.24476 | 5.25195 | 11.87 | 0.36 | 0.361 | 0.001 |
| Z1 | 5.03594 | 0.00000 | 0.25228 | 5.28822 | 0.00 | 0.469 | 2.361 | 1.892 |
| Z2 | 4.94155 | 0.05345 | 0.25405 | 5.24905 | 0.34 | 0.472 | 1.618 | 1.146 |
| Z3 | 4.89029 | 0.12073 | 0.25478 | 5.26580 | 0.77 | 0.464 | 1.526 | 1.062 |
| Z4 | 4.75115 | 0.24831 | 0.25259 | 5.25205 | 1.58 | 0.455 | 1.296 | 0.841 |
| Z5 | 4.52267 | 0.50221 | 0.25131 | 5.27619 | 3.19 | 0.442 | 0.801 | 0.359 |
| Z6 | 4.03195 | 0.99365 | 0.25415 | 5.27975 | 6.31 | 0.423 | 0.426 | 0.003 |
| Z7 | 3.50064 | 1.49004 | 0.24365 | 5.23433 | 9.54 | 0.383 | 0.384 | 0.001 |
| Z8 | 3.06159 | 2.00403 | 0.25834 | 5.32396 | 12.61 | 0.385 | 0.386 | 0.001 |

Graphs of the data shown in Table 8 were used to estimate that the minimal inhibitory concentration of each peptide was between 5 and 7 µg/g.

The experiment was repeated (N=5), and it was observed that the lowest concentration tested (0.52 nanomoles or 0.33 µg/g) inhibited growth of Weissella viridescens NRRL B-1951 by 35.33*4.76%. Graphs of W. viridescens growth at various nisin A concentrations exhibited classic sigmoidal behavior. Further assays were performed to evaluate this sigmoidal behavior, using nisin A at a concentration range of 0.05-0.55 µg/g. The results were fit via four parameter logistic regression (4PLR), combined into a continuous function with a second assay set (0.65-9.99 µg/g), and are shown in FIG. 11A.

Figure 11A:
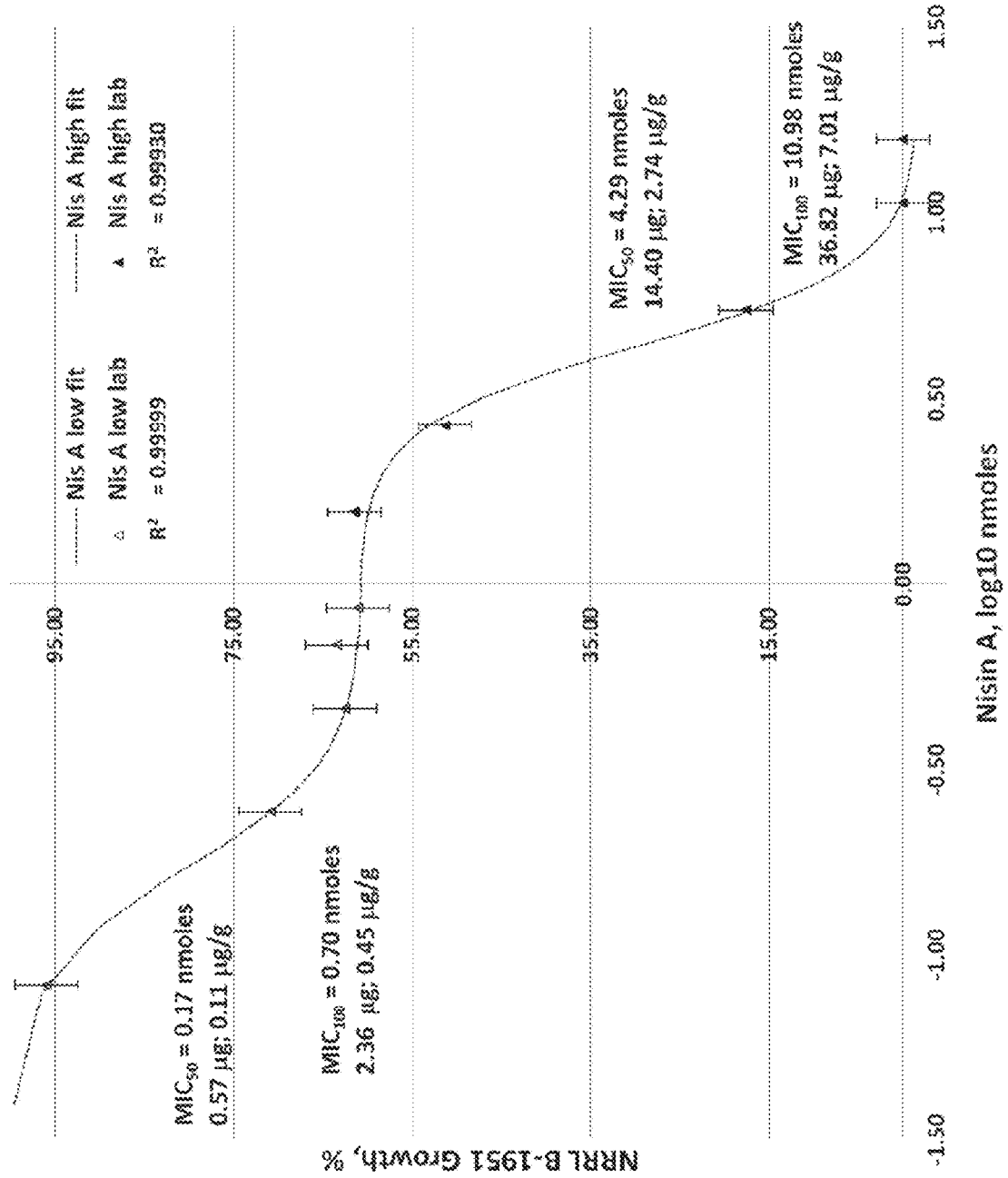
FIG. 11A-11D graphically illustrates inhibition of *Weissella viridescens* NRRL B-1951 growth by nisins.

FIG. 11A indicates that the effect of nisin A/Z on W. viridescens NRRL B-1951 is bimodal. One explanation is that there may be a fraction of the W. viridescens NRRL B-1951 bacteria that are particularly sensitive to nisin. Another possibility is that membrane-sites in sensitive cells may be saturated (assuming cytotoxicity at the >1.00 µg/g threshold). In any case, a maximum of 60-70% growth was observed at any point where concentration was within the plateau between 0.30 and 1.00 µg/g (0.46-1.54 nanomoles).

Figure 11B:
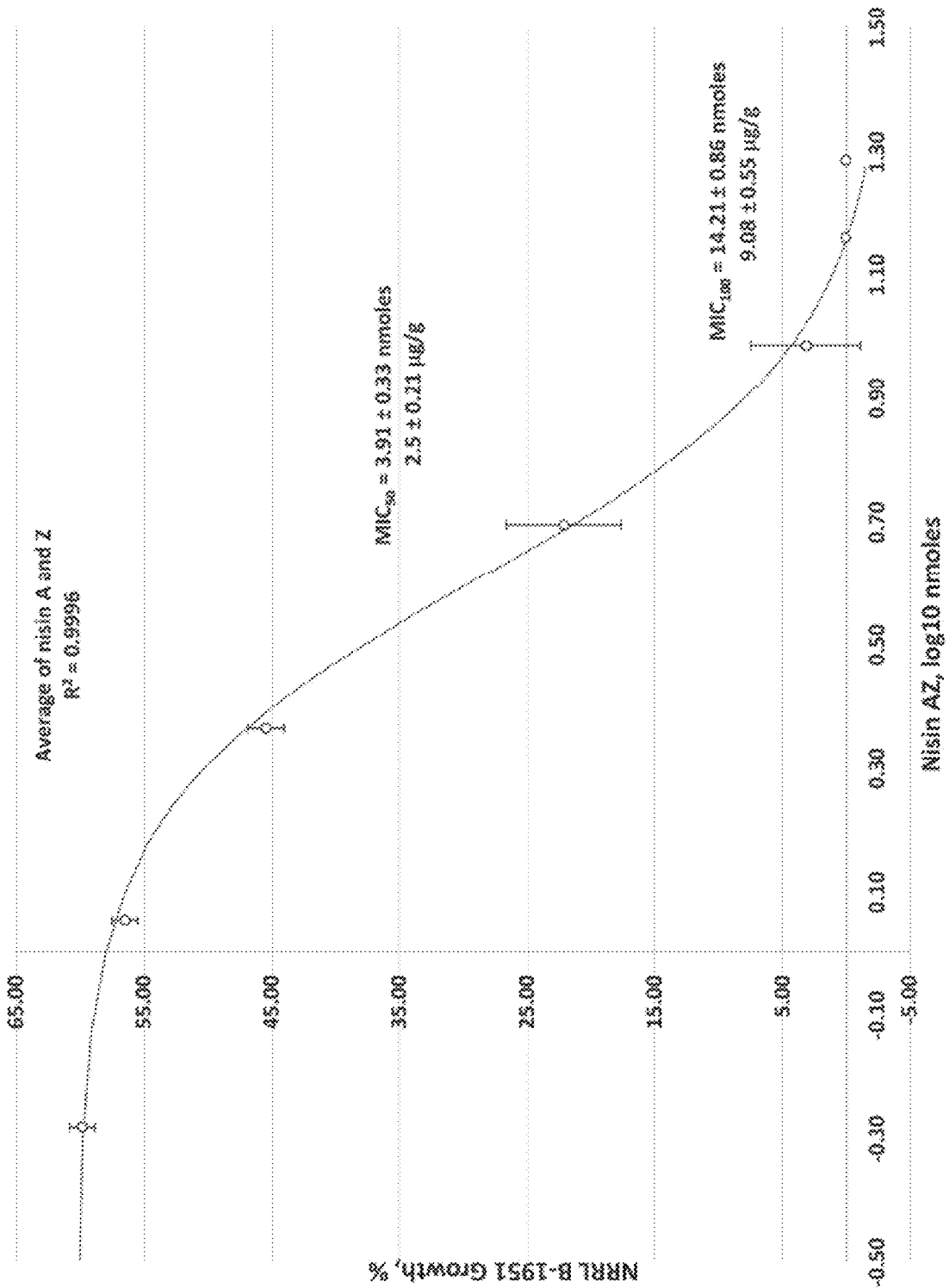

The antibacterial activity of nisins A and Z were similar, with average $MIC_{50}$ values of 4.15±0.19 and 3.68±0.17 nanomoles/sample, respectively (2.65 and 2.35 µg/g). Nisins A and Z demonstrated respective $MIC_{100}$ values of 14.82±0.63 and 13.60±0.59 nanomoles (9.47 and 8.69 µg/g). The average of the $MIC_{50}$ values for A and Z was 2.50±0.21 µg/g (3.91±0.33 nanomoles) and the $MIC_{100}$ was 9.08±0.55 µg/g (14.21±0.86 nanomoles). FIG. 11B graphically illustrates these average values.

Example 11: More Nisin is Produced by Lactococcus lactis in the Presence of a Challenger Microbe This Example demonstrates that a challenger microbe can stimulate a beneficial gut microorganism to produce increased levels of the anti-microbial, nisin.

Materials and Methods

This experiment was designed to compare the antibacterial activity of a base broth produced by a beneficial, protagonist microorganism (Lactococcus lactis) with the antibacterial activity of a broth produced when the beneficial, protagonist organism (Lactococcus lactis) is challenged with a susceptible challenger organism (Weissella viridescens).

Preparation of Cell-Free Broths

Base Broth (generated without challenger Weissella viridescens): M 17 Media (Sigma) was prepared by dissolving 4.207 g M17 powder into 100.017 g (total) water (18MΩ). The media mixture was autoclaved at 121° C. for 15 min. After cooling, the media was inoculated with Lactococcus lactis subsp. lactis NRRL B-1821 (0.5 mL late log-phase culture frozen at −78° C. in 20% glycerol), and the culture was incubated at 35° C. for 16 Hr. This culture was the inoculum for the following fermentation.

To a 2 L fermenter (New Brunswick BioFlo/Celligen 115) was added water (18MΩ, Hydro), 0.960 kg; peptone (meat, Sigma). 10.080 g; bacteriological yeast extract (Marcor), 5.690 g; ISOThrive™ MIMO [lot #160120, a source of maltosyl-isomaltooligosaccharides (MIMOs)], 25.067 g; $MnSO_4$-$H_2O$ (J. T. Baker), 0.0123 g; $MgSO_4$ (Amresco), 0.1156 g; $FeSO_4$-$7H_2O$ (Amresco), 0.0135 g; $KH_2PO_4$ (Alfa Aesar), 2.933 g; NaCl (BDH), 0.01208 g, and $CaCl_2$-$2H_2O$ (Alfa Aesar). 0.6178 g. This fermentation media was autoclaved at 121° C. for 15 minutes. Once cooled to 35° C., a physiological temperature (36-37° C.) was maintained using a recirculating water bath. The pH of the fermentation mixture was adjusted to the physiological pH of the colon (pH 6.6) with NaOH (50% w/w, Fisher) and maintained throughout at pH 6.6 using NaOH (40% w/w).

To the fermenter was aseptically added 10 mL late log-phase Lactococcus lactis subsp. lacs NRRL B-1821 inoculum, and micro-anaerobic (self-blanketing) conditions were maintained. The fermentation was allowed to proceed for 21 Hr before sampling.

The cells were removed via centrifugation (Sorvall RC-5B+, G3 rotor) at 13,689 g for 20 minutes. The supernatant was sampled via HPLC-RTD (organic acids) and HPAEC-PAD (carbohydrate consumption), and the remainder frozen at −78° C. pending analysis of bacteriocin activity by tube-assay vs Weissella viridescens NRRL B-1951 (standardized vs nisin A at 0-10 µg/g; 95.2%, Handary S.A). The samples are also being prepared for mass spectrometry (target 3.358 kDa). A small subsample of the biomass was resuspended, washed, and centrifuged again (Eppendorf 5415 C) at 12 kRPM for 15 minutes. The washed biomass pellet was re-suspended and gram stained for confirmation of culture morphology and purity via oil-immersion microscopy.

Essentially all of the tested prebiotic ISOThrive™ MIMOs in the media had been consumed by 21 hours of incubation. Metabolism was consistent with type behavior for the species. The culture was pure, and the late log morphology conformed with *Lactococcus* spp.

Challenger broth (generated with challenger *Weissella viridescens*): M17 Media (Sigma) was prepared by dissolving 4.202 g M17 powder into 100.319 g (total) water (18MΩ). The media mixture was autoclaved at 121° C. for 15 min. After cooling, the media was inoculated with *Lactococcus lactis* subsp. *lactis* NRRL B-1821 (0.5 mL late log-phase culture frozen at −78° C. in 20% glycerol), and the culture was incubated at 35° C. for 16 Hr. This culture was the inoculum for the following fermentation.

To a 2 L fermenter (New Brunswick BioFlo/Celligen 115) was added water (18Ma, Hydro), 0.960 kg; peptone (meat, Sigma). 10.030 g; yeast extract (Marcor), 5.530 g; ISOThrive™ MIMO [lot #160120, a source of maltosyl-isomaltooligosaccharides (MIMOs)]. 25.054 g; $MnSO_4$-$H_2O$ (J.T. Baker), 0.0121 g; $MgSO_4$ (Amresco), 0.122 g; $FeSO_4$-$7H_2O$ (Amresco), 0.0125 g; $KH_2PO_4$ (Alfa Aesar), 2.901 g; NaCl (BDH), 0.0135 g, and $CaCl_2$-$2H_2O$ (Alfa Aesar), 0.698 g. This fermentation media was autoclaved at 121° C. for 15 minutes. Once cooled to 35° C., a physiological temperature (36-37° C.) was maintained using a recirculating water bath. The pH of the fermentation mixture was adjusted to the physiological pH of the colon (pH 6.6) with NaOH (50% w/w, Fisher) and maintained throughout at pH 6.6 using NaOH (40% w/w).

To the fermenter was aseptically added 10 mL late log-phase *Lactococcus lactis* subsp. *lactis* NRRL B-1821 inoculum, and micro-anaerobic (self-blanketing) conditions were maintained. The fermentation was allowed to proceed for 17 Hr before sampling.

In the meanwhile, De Man, Rogosa, and Sharpe (MRS) media (Difco) was prepared by dissolving 5.500 g MRS powder into 100.972 g (total) water (18MΩ, Hydro). ISOThrive™ (lot #150622), 25.08027 g was dissolved in water, 0.100 kg total. The MRS media and ISOThrive™ solution were autoclaved at 121° C. for 15 min. After cooling, the media was inoculated with *Weissella viridescens* NRRL B-1951 (0.5 mL late log-phase culture frozen at −78° C. in 20% glycerol), and the culture was incubated at 35° C. for 16 Hr. This culture was the secondary (antagonist) inoculum.

The next day, the fermenter was sampled. The cells were removed via centrifugation (Eppendorf 5415 C) at 10 kRPM for 10 minutes. The supernatant was analyzed via HPLC-RID (metabolites) and HPAEC-PAD to ascertain consumption of MIMO.

The autoclaved ISOThrive™ was aseptically transferred to the active fermenter. At 2.5 hours, the fermentation demonstrated renewed uptake of NaOH indicating re-entry into log-growth. At this time, 20 mL antagonizing (*W. viridescens*) inoculum was transferred into the fermenter. The *W. viridescens* culture was propagated from the antagonist inoculum in 100 g MRS media prepared as before. This is the test culture for the tube assays to be carried out the next day.

The secondary fermentation was allowed to proceed overnight (16 Hr).

The cells were removed via centrifugation (Sorvall RC-5B+. G3 rotor) at 13,689 g for 20 minutes. The supernatant was sampled via HPLC-RID (organic acids) and HPAEC-PAD (carbohydrate consumption), and the remainder frozen at −78° C. pending analysis of bacteriocin activity by tube-assay vs *Weissella viridescens* NRRL B-1951 (standardized vs nisin A at 0-10 μg/g; 95.2%, Handary S.A). The samples were also prepared for mass spectrometry (target 3.358 kDa). A small subsample of the biomass was resuspended, washed, and centrifuged again (Eppendorf 5415 C) at 12 kRPM for 15 minutes. The washed biomass pellet was re-suspended and gram stained for confirmation of culture morphology, purity via oil-immersion microscopy and metagenomics sequencing of 16S rRNA (to confirm prevailing species).

For both samples (fermentation prior to second inoculation and final broth). essentially all of the tested prebiotic ISOThrive™ MIMOs in the media had been consumed. Via gram stain, (1000× oil immersion) the culture appeared pure, and the late log morphology conformed with *Lactococcus* spp. The morphological similarities between the *Lactococcus* and *Weissella* spp. was noted. This is why the sample was submitted for verification of identity via 16S rRNA. The result of the DNA sequencing is pending. Confirmation of bacteriocin identity via mass spectrometry is pending.

Tube Assay

The base and challenger broths were tested for growth inhibition of a susceptible organism (*Weissella viridescens* NRRL B-1951) simultaneously.

MRS media was prepared to contain 5.509 g solids in DI water to 0.101 kg total. Two sets of 6 tubes (Hach-type, Kimble Chase 45066-16100) were rigorously cleaned (Tergazyme detergent. Alconox), solvent rinsed with acetone, and dried. To each set of tubes was added MRS media, in order. 5.0, 4.5, 4.0, 3.5, and 3.0 g. The tubes were autoclaved (121° C., 15 min) and cooled to room temperature.

To the first set of tubes was then added base broth (cell-free *L. lactis* broth), 0.0, 0.5, 1.0, 1.5, and 2.0 g. To the second set of tubes was added challenger broth (cell-free *L. lactis*+*W. viridescens* broth), 0.0, 0.5, 1.0, 1.5, and 2.0 g. All tubes were inoculated with 0.25 g of fresh *W. viridescens* culture. All tubes were then immediately assayed for absorbance at 600 nm (Hach DR 900) to establish baseline values. The tubes were incubated at 35° C., overnight (16 Hr) to evaluate whether the freshly added fresh *W. viridescens* cells grew.

The next day, the tubes were agitated to suspend any settled cells/sediment and assayed again via absorbance at 600 nm. Growth curves were determined by subtracting the final from the initial absorbance for each sample. The pH of each tube was checked via pH strip (pHast strips), and samples were taken for analysis via HPLC-RID.

Results

Figure 11C:
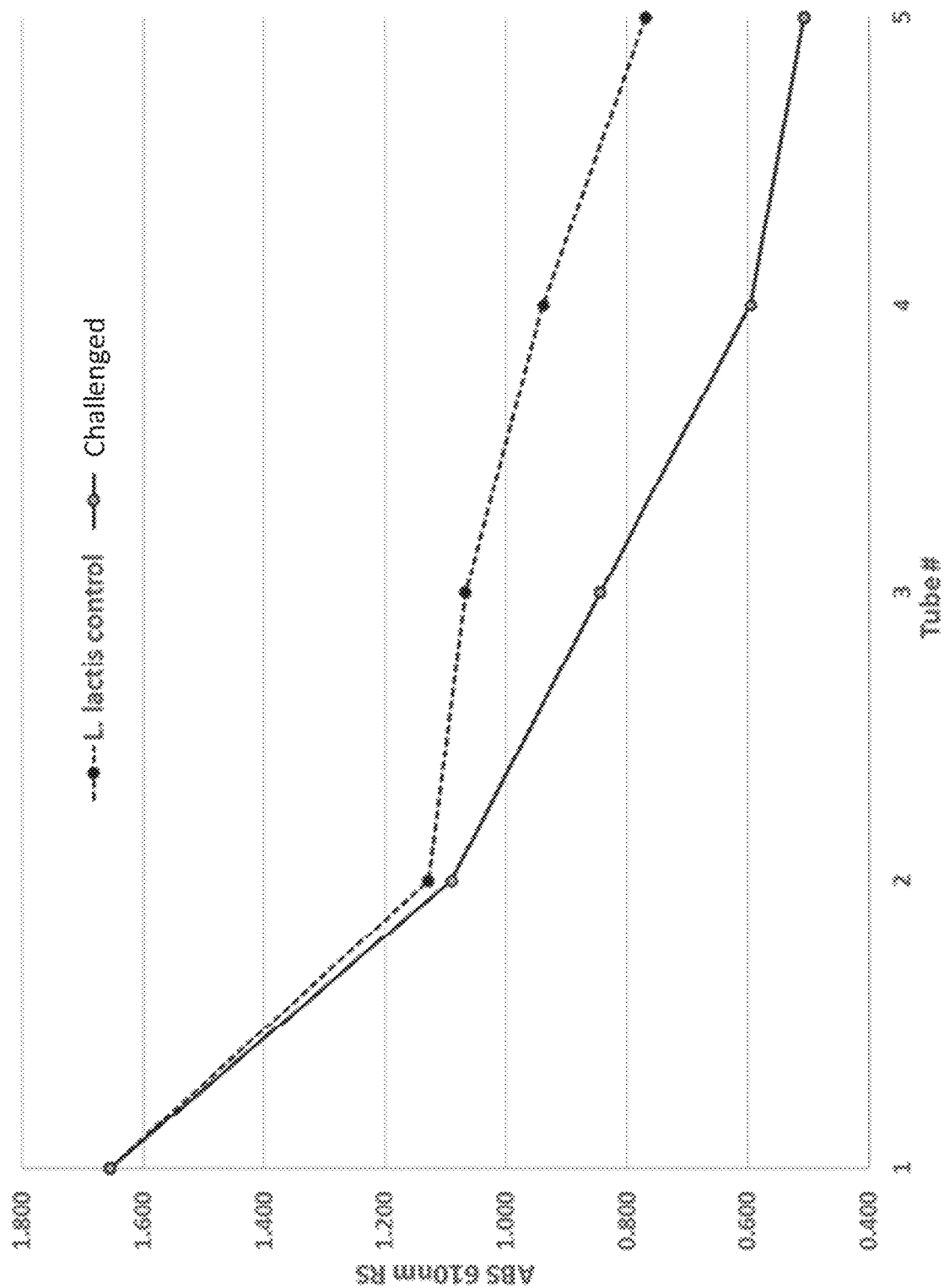
Figure 11D:
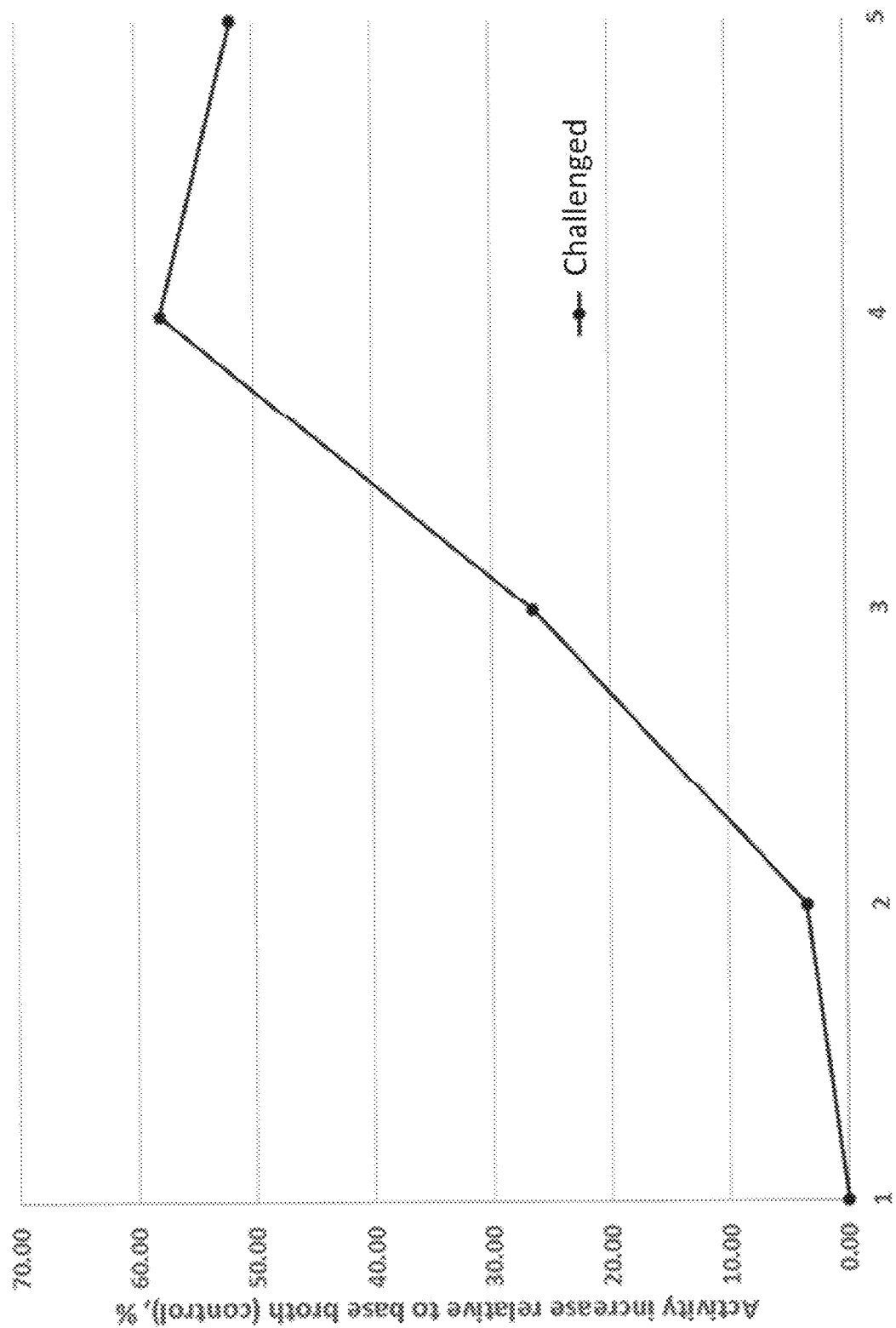

The challenger broth demonstrated 34% greater antibacterial activity (30.6% growth/control) than the base broth (46.5% growth/control) when compared at lowest dilution (40% broth/sample) (FIGS. 11C-11D). Considering the MICs assigned for nisin A (5-7 μg/g or in a separate experiment about 2.5 μg/g for *W. viridescens*; Example 10), the base broth contained appx. 1.7 μg nisin A/g broth and the challenger broth contained appx. 3.8 μg nisin A/g broth based on equivalent activity.

These data indicate that the presence of a challenger microbe (e.g., *Weissella viridescens*) stimulates a beneficial, protagonist gut microorganism (*L. lactis*) to produce beneficial compounds *or* materials (e.g., nisin) in response to the challenge.

REFERENCES

1. Papagianni, M, and Anastasiadou, S. (2009). "Pediocins: The Bacteriocins of Pediococci. Sources, Production, Properties, and Applications. Microb. Cell Fact. 8(3), doi:10.1186/1475-2859-8-3.

2. McAuliffe, O., Ryan, M. P., Ross, R. P., Hill, C., Breeuwer, P, and Abee, T. (1998). "Lacticin 3147, a Broad-Spectrum Bacteriocin Which Selectively Dissipates the Membrane Potential." Appl. Environ. Microbiol. 64 (2), pp. 439-445.

3. Maldonado, A., Jimenez-Diaz. R, and Ruiz-Barba, J-L. (2004). "Induction of Plantaricin Production in *Lactobacillus plantarum* NC8 after Coculture with Specific Gram-Positive Bacteria is Mediated by an Autoinduction Mechanism. J. Bacteriol. 186 (5), pp. 1556-1564.

4. Holo, H., Jeknic. Z., Daeschel, M., Stevanovic, S, and Nes, I. F. (2001). "Plantaricin W from *Lactobacillus plantarum* Belongs to a New Family of Two-peptide Lantibiotics." Microbiol. 147 (3), pp. 643-651.

5. Herranz, C., and Driessen, A. J. M. (2005). "Sec-Mediated Secretion of Bacteriocin Enterocin by *Lactococcus lactis*." Appl. Environ. Microbiol. 71 (4), pp. 1959-1963.

6. Gratia, A. (1925). "Sur un remarquable example d'antagonisme entre deux souches de colibacille". Compt. Rend. Soc. Biol. 93, pp. 1040-1042.

7. Jones. E., Salin, V, and Williams, G. W. (2005). "Nisin and the Market for Commercial (sic) Bacteriocins." TAMRC Consumer and Product Research Report No. CP-01-05 (see webpage at ageconsearch.umn.edu/bitstreanm90779/2/CP %2001%2005%20Nisin%20Report.pdf).

8. Zorn, H, and Czermak, P. (2014). "Biotechnology of Food and Feed Additives." Advances in Biochemical Engineering/Biotechnology 143, Scheper, T. ED. Springer, Heidelberg-New York-Dordrecht-London. ISBN #978-3-662-43760-5, DOT 10.1007/978-3-662-43761-2. pp. 32-34.

9. Reeves. P. (1979). "The Concept of Bacteriocins." Zentralbl. Bakteriol. Orig. A. 244 (1). pp. 78-89.

5. Fox, P. F., Guinee, T. P., Cogan, T. M, and McSweeney, P. L. H. (2000). "Fundamentals of Cheese Science." Aspen Publishers, Inc. Gaithersburg, Md. ISBN 0-8342-1260-9, pp. 92-95.

10. Stevens, K. A., Sheldon, B. W., Klapes, N. A, and Klaenhammer, T. R. (1991). "Nisin Treatment for Deactivation of *Salmonella* Species and Other Gram Negative Bacteria." Appl. Environ. Microbiol. 57 (12), pp. 3613-3615.

11. Kamarajan, P., Havami, T., Matte, B., Liu, Y., Danclu, T., Ramamoorthy, A., Worden, F., Kapila, S, and Kapila, Y. (2015). "Nisin ZP, a Bacteriocin and Food Preservative, Inhibits Head and Neck Cancer Tumorigenesis and Prolongs Survival." PLOS ONE, DOT:10.1371/journal.pone.0131008.

12. Shin, J. M., Gwak, J. W., Kamarajan, P., Fenno, J. C., Rickard, A. H, and Kapila, Y. L. (2015). "Biomedical Applications of Nisin." J. Appl. Microbiol. 120, pp. 1449-1465.

13. Kamarajan. P., Hayami, T., Matte. B., Liu, Y., Danciu, T., Ramamoorthy, A., Worden, F., Kapila, S, and Kapila, Y. (2015). "Nisin ZP, a bacteriocin and Food Preservative Inhibits Head and Neck Cancer Tumorigenesis and Prolongs Survival." PLOS ONE DOI:10.1371/journal.pone.0131008, pp. 1-20.

14. Joo, N. E., Ritchie, K., Kamarajan, P., Miao, D, and Kapila. Y. (2012). "Nisin, an Apoptotic Bacteriocin and Food Preservative, Attenuates HNSCC Tumorigenesis via CHAC1. Cancer Medicine 1 (3), pp. 295-305.

15. Kaur, S, and Kaur, S. (2015). "Bacteriocins as Potential Anticancer Agents." Front. Pharmacol. 6 (272), pp. 1-11.

16. Zschuttig, A., Zimmerman, K., Blom, J., Goesmann, A., Pohlnann, C, and Gunzer, F. (2012). "Identification and Characterization of Microcin S, a New Antibacterial Peptide Produced by Probiotic *Escherichia coli* G3/10." PLOS ONE 7 (3):e33351; doi: 10.1371/journal.pone.0033351.

17. Hetz, C., Bono, M. R., Barros, L. F, and Lagos, R. (2002). "Microcin E492, a Channel-Forming Bacteriocin from *Klebsiella pneumoniae*, Induced Apoptosis in some Human Cell Lines." Proc. Natl. Acad. Sci. U.S.A. 99 (5), pp. 2696-2701.

18. Piva, A, and Headon, D. R. (1994). "Pediocin A, a Bacteriocin Produced by *Pediococcus pentosaceus* FBB6L." Microbiology 140 (4), pp. 697-702.

19. Simha, B. V., Sood, S. K., Kumariya, R, and Garsa, A. K. (2012). "Simple and Rapid Purification of Pediocin PA-1 from *Pediococcus pentosaceus* NCDC 273 Suitable for Industrial Application. Microbiol. Res. 167 (9), pp. 544-549.

20. Chikindas, M. L., Garcia-Garcera, M. J., Driessen, A. J. M., Ledeboer, A. M., Nissen-Meyer, J., Nes, I. F., Abee, T., Kinings, W. N, and Venema, G. (1993). "Pediocin PA-1, a Bacteriocin from *Pediococcus acidilactici* PAC1.0, Forms Hydrophilic Pores in the Cytoplasmic Membrane of Target Cells." Appl. Env. Microbial. 59 (11). pp. 3577-3584.

21. Rodriguez, J. M., Matrinez, M. I, and Kok. J. (2002). "Pediocin PA-1, a Wide-Spectrum Bacteriocin from Lactic Acid Bacteria." Crit. Rev. Food Sci. 42 (2), pp. 91-121.

22. Lianou, A, and Sameli, J. (2014). "Addition to Termalized Milk of *Lactococcus lactis* subsp. *cremoris* M104, a Wild Nisin-A Producing Strain, Replaces the Natural Antilisterial Activity on the Autochthonous Raw Milk Microbiota Reduced by Thermalization." J. Food. Prot. 77(8), pp. 1289-1297.

23. Delves-Broughton, J. (1990). "Nisin and its Application as a Food Preservative." Int. J. Dairy Technol. 43 (3), pp. 73-76.

24. De Vos, W. M., Mulders, J. W., Siezen, R. J., Hugenholtz, J, and Kuipers, O. P. (1993). "Properties of Nisin Z and Distribution of its Gene, nisZ, in *Lactococcus lactis*." Appl. Env. Microbiol. 59 (1), pp. 213-218.

25. Shin, J. M., Gwak, J. W., Kamarajan, P., Fenno, J. C., Rickard, A. H, and Kapila, Y. L. (2016). "Biomedical Applications of Nisin." J. Appl. Microbiol. 120 (6), pp. 1449-1465.

26. O'Connor, P. M., O'Shea. E. F, and Guinane, C. M. (2015). "Nisin H is a New Nisin Variant Produced by the Gut-Derived Strain *Streptococcus hyointestinalis* DPC6484." Appl. Env. Microbiol. 81 (12), pp. 3953-3960.

27. Wirawan, R. E., Klesse, N. A., Jack, R. W, and Tagg, J. R. (2006). "Molecular and Genetic Characterization of a Novel Nisin Variant Produced by *Streptococcus uberis*." Appl. Env. Microbial. 72 (2), pp. 1148.1156.

28. Entian, K-D, and de Vos, W. M. (1996). "Genetics of Subtilin and Nisin Biosynthesis." Antonie van Leeuwenhoek 69 (2). pp. 109-117.

29. Diep, D. B., Havarstein, L. S., Nissen-Meyer, J, and Nes, I. F. (1994). "The Gene Encoding Plantaricin A, a Bacteriocin from *Lactobacillus plantarum* C11. is Located on the Same Transcription Unit as an AGR-like Regulatory System." Appl. Env. Microbiol. 60 (1). pp. 160-166.

30. Maldonado, A., Jumenez-Diaz, R, and Ruiz-Barba, J. L. (2004). "Induction of Plantaricin Production in *Lactobacillus plantarum* NC8 after Coculture with Specific Gram-Positive Bacteria is Mediated by an Autoinduction Mechanism." J. Bacteriol. 186 (5), pp. 1556-1564.

31. Holo, H., Jeknic, Z., Daeschel, M., Stevanovic, S, and Nef, I. F. (2001). "Plantaricin W from *Lactobacillus* plantarum Belongs to a New Family of Two-peptide Lantibiotics." Microbiology 147 (3), pp. 643-651.
32. Song, D-F., Zhu, M-Y, and Gu, Q. (2014). "Purification and Characterization of Plantaricin ZJ5, a New Bacteriocin Produced by *Lactobacillus plantarum* ZJ5." PLOS ONE (see webpage at dx.doi.org/10.1371/journal.pone.0105549)
33. Todorev. S. D., Vaz-Velho, M, and Gibbs, P. (2004). "Comparison of Two Methods for Purification of Plantaricin ST31, a Bacteriocin Produced by *Lactobacillus plantarum ST*31." Braz. J. Microbiol. 35 (1), see webpage /dx.doi.org/10.1590/S1517-83822004000100026).
34. Lim, S. W., Koshy. P, and Noni, A. (2016). "Purification. Characterization and Mode of Action of Plantaricin K25 produced by *Lactobacillus plantarum*. "Food Control 60, pp. 430-139.
35. Holck, A., Axelsson, L., Birkland, S-E., Aukrust, T, and Blom, H. (1992). "Purification and Amino Acid Sequence of Sakacin A, a Bacteriocin from *Lactobacillus* sake Lb706." J. Gen. Microbiol. 138, pp. 2715-2720.
36. Simon, L., Fremaux, C., Cenatiempo, Y, and Berjeaud, J. M. (2002). "Sakacin G, a New Type of Antilisterial Bacteriocin." Appl. Env. Microbiol. 68 (12), pp. 6416-6420.
37. Mathiesen, G., Huehne, K., Kroeckel, L., Axelsson, L, and Eijsink. V. G. (2005). "Characterization of a New Bacteriocin Operon in Sakacin P-producing *Lactobacillus* sakei, Showing Strong Translational Coupling Between the Bacteriocin and Immunity Genes." Appl. Env. Microbiol. 71 (7), pp. 3565.3574.
38. Gao, Y., Li. D., Sheng, Y, and Liu, X. (2011). "Mode of Action of Sakacin C2 against *Escherichia coli*." Food Control 22(5), pp. 657-661.
39. Barefoot. S. F, and Klaenhammer. T. R. (1983). "Detection and Activity of Lactacin B, a Bacteriocin Produced by *Lactobacillus acidophilus*." Appl. Env. Microbiol. 45 (6), pp. 1808-1815.
40. Muriana, P. M, and Klaenhammer, T. R. (1991). "Purification and Partial Characterization of Lactacin F. a Bacteriocin Produced by *Lactobacillus acidophilus* 11088." Appl. Env. Microbiol. 57 (1), pp. 114-121.
41. Tabasco. R., Garcia-Cayuela, T., Pelaez, C, and Requena, T. (2009). "*Lactobacillus acidophilus* La-5 Increases Lactacin B Production When it Senses Live Target Bacteria." Int. J. Food Microbiol. 132, pp. 109-116.
42. Upreti. G. C, and Hinsdill, R. D. (1975). "Production and Mode of Action of Lactocin 27: Bacteriocin from a Homofermentative *Lactobacillus*." Antimicrob. Agents Chemother. 7 (2), pp. 139-145.
43. Turovskiy, Y., Ludenscher, R. D., Aroutcheva, A. A., Faro, S, and Chikindas, M. L. (2009). "Lactocin 160, A Bacteriocin Produced by Vaginal *Lactobacillus rhamnosus* Targets Cytoplasmic Membranes of the Vaginal Pathogen, *Gardnerella vaginalis*." Probiotics Antimicrob. Proteins 1 (1), pp. 67-74.
44. Hastings, J. W., Sailer, M., Johnson, K., Roy, K. L., Vederas, J. C, and Stiles. M. E. (1991). "Characterization of Leucocin A-UAL 187 and Cloning of the Bacteriocin Gene from *Leuconostoc gelidun*." J. Bacteriol. 173 (23), pp. 7491-7500.
45. Zacharof, M. P, and Lovitt. R. W. (2012). "Bacteriocins Produced by Lactic Acid Bacteria A Review Article." APCBEE Procedia 2. pp. 50-56.
46. Makhloufi, K. M., Carre-Mlouka, A., Peduzzi. J., Lombard, C., van Reenen, C. A., Theodore Dicks, L. M, and Rebuffat, S. (2013). "Characterization of Leucocin B-KM432Bz from Leeuconostoc pseudomesenteroides Isolated from Boza, and Comparison of its Efficiency to Pediocin PA-1." PLOS ONE (see webpage at dx.doi.org/10.1371/journal.pone.0070484).
47. Felix, J. A., Papathanasopoulos, M. A., Smith. A. A., von Holy, A, and Hastings, J. W. (1994). "Characterization of Leucocin B-Tal1a: A Bacteriocin from *Leuconostoc* carnosum Tal1a Isolated from Meat." Current Microbiol. 29, pp. 207-212.
48. Castellano, P., Raya, R, and Vignolo, G. (2003). "Mode of Action of Lactocin 705, a Two-Component Bacteriocin from *Lactobacillus casei* CRL705." Int. J. Food. Microbiol. 85 (1-2), pp. 35-43.
49. Mortvedt-Abildgaard. C. I., Nissen-Meyer, J., Jelle, B., Grenov, B., Skaugen. M, and Nes, I. F. (1995). "Production and pH-Dependent Bactericidal Activity of Lactocin S. a Lantibiotic from *Lactobacillus* sake L45." Appl. Env. Microbiol. 61 (1), pp. 175-179.
50. Fuchs, S. W., Jaskolla, T. W., Bochmann, S., Kotter, P., Wichelhaus, T., Karas, M., Stein, T, and Enian, K-D. (2011). "Entianin, a Novel Subtilin-like Lantibiotic from *Bacillus subtilis* subsp. *spizizenii* DSM 15029 with High Antimicrobial Activity." Appl. Env. Microbiol. 77 (5), pp. 1698-1707.
51. Jena, P. K., Trivendi, D., Chaudhary, H, and Seshadri, S. (2013). "Bacteriocin PJ4 Active against Enteric Pathogen Produced by *Lactobacillus helveticus* PJ4 Isolated from Gut Microflora of Wistar Rat (*Rattus norvegicus*): Partial Purification and Characterization of Bacteriocin." Appl. Biochem. Biotechnol. 169 (7), DOI: 10.1007/s12010-012-0044-7.
52. Tufail. M., Hussain, S., Malik, F., Mirza, T., Parveen, G., Shafaat, S., Wajid, A., Mahmood. R., Channa, R. A, and Sadiq, A. (2011). "Isolation and Evaluation of Antimicrobial Activity of Bacteriocin Produced by *Lactobacillus bulgaricus* from Yogurt." African J. Microbiol. Res. 5(22), pp. 3842-3847.
53. Michaylova. M., Minkova, S., Kimura, K., Sasaki, T, and Isawa, K. (2007). "Isolation and Characterization of *Lactobacillus delbrueckii* ssp. *bulgaricus* and *Streptococcus thermophilus* from Plants in Bulgaria." FEMS Microbiol. Lett. 269 (1), pp. 160-169.
54. Bonelli, R. R., Schneider. T., Sahl, H. G, and Wiedemann, 1. (2006). "Insights into In Vivo Activities of Lantibiotics from Gallidermin and Epidermin Mode-of-Action Studies." Antimicrob. Agents Chemother. 50 (4), pp. 1449-1457.
55. Kellner. R., Jung, G., Homer, T., Zahner, H., Schnell, N., Entian, K. D, and Gotz, F. (1988). "Gallidermin: A New Lanthionine-Containing Polypeptide Antibiotic." Eur. J. Biochem. 177 (1), pp. 53-59.
56. Bierbaum, G., Gotz, F., Peschel, A., Kupke, T., van de Kamp, M, and Sahl, H. G. (1996). "The Biosynthesis of Lantibiotics Epidermin, Gallidermin, Pep5 and Epilancin K7." Antonie Van Leeuwenhoek 69 (2), pp. 119-127.
57. Gotz, F., Perconti, S., Popella, P., Werner, R, and Schlag, M. (2014). "Epidermin and Gallidermin: Staphylococcal Lantibiotics." Int. J. Med. Microbiol. 304 (1), pp. 63-71.
58. Velasquez, J. E., Zhang, X, and van der Donk, W. A. (2011). "Biosynthesis of the Antimicrobial Peptide Epilancin 15X and its N-terminal Lactate." Chem. Biol. 18 (7), pp. 857-867.
59. Brotz, H., Bierbaum, G., Reynolds. P. E, and Sahl, H-G. (1997). "The Lantibiotic Mersacidin Inhibits Peptidoglycan Biosynthesis at the Level of Transglycosylation." Eur. J. Biochem. 246, pp. 193-199.

60. Altena. K., Guder, A., Cramer, C., Bierbaum. G. (2000). "Biosynthesis of the Lantibiotic Mersacidin: Organization of a Type B Lantibiotic Gene Cluster." Appl. Env. Microbiol. 66 (6), pp. 2565-2571.
61. McBride, J. (2000). "B12 Deficiency May Be More Widespread Than Thought." USDA ARS, ars.usda.gov/is/pr/2000/000802.htm
62. Pawlak, R., Parrott, S. J., Raj, S., Cullum-Dugan, D, and Lucus, D. (2013). "How Prevalent is Vitamin B(12) Deficiency Among Vegetarians?" Nutr. Rev. 71 (2), pp. 110-7.
63. Lim, S-H., Choi, J. S, and Park, E. Y. (2001). "Microbial Production of Riboflavin Using Riboflavin Overproducers *Ashbya gossypii, Bacillus subtilis*, and *Candida fumate*: An Overview." Biotechnol. Bioprocess Eng. 6, pp. 75-88.
64. LeBlanc, J. G., Milani, C., de Giori, G. S., Sesma, F., van Sinderen, D, and Ventura, M. (2013). "Bacteria as Vitamin Suppliers to their Host: a Gut Microbiota Perspective." Curr. Opin. Biotechnol. 24(2), pp. 160-8.
65. Perkins, J. B, and Pero, J. (2002). "Vitamin Biosynthesis. In *Bacillus subtilis* and its closest relatives from genes to cells." Sonenshein, A., Hoch. J, and Losick, R. EDs. ASM Press, pp. 271-286.
66. Martens, J. H., Barg, H., Warren, M. J, and Jahn, D. (2002). "Microbial Production of Vitamin B12." Appl. Microbiol. Biotechnol. 58, pp. 275-285.
67. Taranto, M. P., Vera, J. L., Hugenholz, J., de Valdez, G S and Sesma, F. (2003). "*Lactobacillus reuteri* CRL1098 Produces Cyanocobalamin. J. Bacteriol. 185, pp. 5643-5647.
68. Hollriegl, V., Lamm, L., Rowold. J., Horig, J, and Renz, P. (1982). "Biosynthesis of Vitamin B12 Different Pathways in Some Aerobic and Anaerobic Microorganisms." Arch. Microbiol. 132, pp. 155-158.
69. Alm. L. (1982). "Effect of Fermentation on B-Vitamin Content of Milk in 40 Sweden." J. Dairy. Sci. 65, pp. 353-359.
70. Shahani, K. M, and Chandan, R. C. (1979). "Nutritional and Healthful Aspects of Cultured and Culture-Containing Dairy Foods." J. Dairy Sci. 62, pp. 1685-1694.
71. Champagne, C. P., Tompkins, T. A., Buckley, N. D, and Green-Johnson, J. M. (2010). Effect of Fermentation by Pure and Mixed Cultures of *Streptococcus thermophilus* and *Lactobacillus helveticus* on Isoflavone and B-Vitamin Content of a Fermented Soy Beverage." Food Microbiol. 27, pp. 968-972.
72. McCarthy, R. J. (2004). "Amino Acid Requirements of Dairy *Propionibacterium* Strains." Ohio State University. http://ift.confex.com/ift/2004/techprogram/paper_26294.htm.
73. Lan, A. (2008). "Increased Induction of Apoptosis by *Propionibacterium freudenreichii* TL 133 in Colonic Mucosal Crypts of Human Microbiota-Associated Rats treated with 1,2-dimethylhydrazine." British J. Nutr. 100 (6). pp. 1251-1259.
74. Jan, G., Balzacq, A-S., Haouzi, D., Roualt, A., Metivier, D., Kroemer, G, and Brenner, C. (2002). "Propioniobacteria Induce Apoptosis of Colorectal Carcinoma Cells via Short-Chaim Fatty Acids acting on Mitochondria. Cell Death & Differentiation 9 (2), pp. 179-188.
75. Courtin, R, and Rul, F. O. (2003). "Interaction between Microorganisms in a Simple Ecosystem: Yogurt Bacteria as a Study Model." Le Lait 84, pp. 125-134.
76. Simova. E. D., Bashkova, D. M., Angelov, M. P, and Dimitrov, Z. P. (2008). "Bacteriocin Production by Strain *Lactobacillus delbrueckii* ssp. *Bulgaricus* BB18 during Continuous Prefermentation of Yogurt Starter Culture and Subsequent Batch Coagulation of Milk. J. Ind. Microbiol. Biotechnol. 35 (6), pp. 559.567.
77. Ghouri. Y. A., Richards, D. M., Rahimi. E. F., Krill, J. T., Jelinek. K. A, and DuPont, A. W. (2014). "Systematic Review of Randomized Controlled Trials of Probiotics, Prebiotics, and Symbiotic in Inflammatory Bowel Disease." Clin. Exp. Gastroenterol. pp. 473-487.
78. Hegazy, S. K, and El-Bedewy, M. M. (2010). "Effect of Probiotics on Pro-Inflammatory Cytokines and NF-kappaB Activation in Ulcerative Colitis." World J. Gastroenterol. 16(33), pp. 4145-4151.
79. Rossi, M., Amaretti, A, and Raimondi, S. (2011). "Folate Production by Probiotic Bacteria." Nutrients 3, pp. 118-134.
80. LeBlanc, J. G., de Giori, G. S., Smid, E. J., Hugenholtz, J, and Sesma. F. (2007). "Folate Production by Lactic Acids Bacteria and Other Food-Grade Microorganisms." Comm. Cuff. Res. Educ. Topics and Trends Appl. Microbiol. Formatex pp. 329-339.
81. Walther, B., Karl, J. P., Booth, S. L, and Boyaval. P. (2013). "Menaquinones, Bacteria, and the Food Supply: The Relevance of Dairy and Fermented Food Products to Vitamin K Requirements." Adv. Nutr. 4, pp. 463-473.
82. Boundless. "Antibiotics from Prokaryotes." *Boundless Microbiology*. Boundless, 26 May 2016. Retrieved 24 Jul. 2016 from www.boundless.com/microbiology/textbooks/boundless-microbiology-textbook/antimicrobial-drugs-13/commonly-used-antimicrobial-drugs-155/antibiotics-from-prokaryotes-784-5906/.
83. Rolhion & Chassaing, When pathogenic bacteria meet the intestinal microbiota. Phil. Trans. R. Soc. B 371: 20150504 (2016).
84. Dobson et al., "Bacteriocin Production: a Probiotic Trait." Appl Environ Microbiol 78(1):1-6 (2012).

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements describe various features of the invention.

STATEMENTS

1) A method comprising: administering a challenger probiotic composition to a subject, where challenger probiotic composition comprises challenger microbes that can stimulate protagonist microorganisms to produce compounds and/or materials that that are beneficial to the subject.
2) The method of statement 1, wherein the challenger microbes comprise dead, attenuated, or live microorganisms.
3) The method of statement for 2, wherein the challenger microbes comprise one or more types or species of microbes that exhibit reduced growth or reduced activity in the presence of beneficial compounds and/or in the presence of compounds or materials produced by protagonist microorganisms.
4) The method of statement 1, 2, or 3, wherein the microbes in the challenger probiotic composition can produce quorum sensing compounds (e.g., quorum sensing peptides, N-acyl homoserine lactones, autoinducers, and combinations thereof).
5) The method of statement 1-3 or 4, wherein the microbes in the challenger probiotic composition comprise one or more of any of the microorganisms or microbes described herein.
6) The method of statement 1-4 or 5, wherein the microbes in the challenger probiotic composition comprise one or more species of bacteria, yeast, and combinations thereof.
7) The method of statement 1-5 or 6, wherein the microbes in the challenger probiotic composition comprise one or more species of *Lactobacillus acidophilus, Lactobacillus bulgaricus, Lactococcus lactis* (subsp. *lactis/creamoris*), *Lactobacillus delbrueckii, Lactobacillus fermentum, Lactobacillus gasseri, Lactobacillus helveticus, Lactobacillus johnsonii, Lactobacillus plantarum, Lactobacillus paracasei, Lactobacillus reuteri, Lactobacillus rhamnosus, Lactobacillus sakei, Leuconostoc gelidum, Leuconostoc pseudomesenteroides, Leuconostoc carnosum, Arthrobacter nicotinae, Bacteroides thetaiotaomicron, Bifidobacterium adolescentis, Bifidobacterium bifidum, Bifidobacterium dentium, Bifidobacterium infantis, Bifidobacterium longum, Bacillus cereus, Bacillus coagulans, Bacillus megaterium, Bacillus subtilis, Bacillus subtilis* ATCC6633, *Brochontrix thermosphacta, Clostridium butylicum, Clostridium acetobutylicum. Clostridium thermoaceticum, Escherichia coli* strain G3110, *Escherichia coli* strain G1/2, *Escherichia coli* strain G4/9, *Escherichia coli* strain G5. *Escherichia coli* strain G6/7, *Escherichia coli* strain G8, *Eubacterium rectale, Eubacterium eligens, Klebsiella pneumoniae, Mycobacterium smegmatis, Nocardia restricta, Nocardia rugosa, Nocardia salmonicida, Pediococcus acidilactici, Pediococcus pentosaceus* FBB61, *Propionibacterium acidipropionici, Propionibacterium freudenreichii, Propionibacterium jensenii. Propionibacterium thoenii, Saccharomyces* spp., *Saccharomyces boulardii, Staphylococcus aureus, Staphylococcus epidermidis. Staphylococcus equorum, Staphylococcus gallinarum, Staphylococcus lugdunensis, Staphylococcus nepalensis, Streptococcus salivarius, Staphylococcus surcinus, Staphylococcus xylosus, Streptococcus hyointestinalis* DPC6484, *Streptococcus uberis* strain 42, *Streptococcus thermophilus,* and *Weissella viridescens.*
8) The method of statement 1-6 or 7, wherein the challenger probiotic composition comprises about $10^6$ to about $10^{13}$ CFU microbes, or about $10^7$ to about $10^{12}$ CFU microbes, or about $10^8$ to about $10^{12}$ CPU microbes, or about $10^9$ to about $10^{12}$ CFU microbes, or about $10^6$ to about $10^{11}$ CFU microbes. or about $10^6$ to about $10^{10}$ CFU microbes, or about $10^6$ to about $10^9$ CFU microbes, or about $10^9$-$10^{11}$ CFU microbes.
9) The method of statement 1-7 or 8, wherein the compounds and/or materials that that are beneficial to the subject comprise one or more lantibiotics, bacteriocins, antibacterial compounds, anti-cancer agents, nutrients, vitamins, short chain fatty acids (SCFAs), hydrogen peroxide, neuromodulators, neurotransmitters (e.g., gamma-aminobutyric acid (GABA)), co-factors (e.g., NAD, cAMP. etc.), and combinations thereof.
10) The method of statement 1-8 or 9, wherein the compounds and/or materials that that are beneficial to the subject comprise one or more bacteriocins, antibacterial compounds, anti-cancer agents, or combinations thereof.
11) The method of statement 1-9 or 10, where the challenger probiotic composition further comprises one or more types or species of protagonist microorganisms.
12) The method of statement 1.10 or 11, further comprising administering a protagonist probiotic composition to the subject.
13) The method of statement 11 or 12, wherein the protagonist microorganisms comprise one or more of *Lactobacillus acidophilus, Lactobacillus bulgaricus, Lactococcus lactis* (subsp. *lactis/creamoris*), *Lactobacillus delbrueckii, Lactobacillus fermentum, Lactobacillus gasseri, Lactobacillus helveticus, Lactobacillus johnsonii, Lactobacillus plantarum, Lactobacillus paracasei, Lactobacillus reuteri, Lactobacillus rhamnosus, Lactobacillus sakei, Leuconostoc gelidum, Leuconostoc pseudomesenteroides, Leuconostoc carnosum, Arthrobacter nicotinae, Bacteroides thetaiolaomicran, Bifidobacterium adolescentis, Bifidobacrterium bifidum, Bifudobacterium dentium, Bofdobacterium infantis, Bifidobacterium longum, Bacillus cereus, Bacillus coagulans, Bacillus megaterium. Bacillus subtilis, Bacillus subtilis* ATCC6633, *Brochontrix thermosphacta, Clostridium butylicum, Clostridium acetobutylicum, Clostridium thermoaceticum, Escherichia coli* strain G3110, *Escherichia coli* strain G1/2, *Escherichia coli* strain G4/9, *Escherichia coli* strain G5, *Escherichia coli* strain G6/7, *Escherichia coli* strain G8. *Eubacterium rectale, Eubacterium eligens, Klebsiella pneumoniae, Mycobacterium smegmatis, Nocardia restricta, Nocardia rugosa, Nocardia salmonicida, Pediococcus acidilactici, Pediococcus pentosaceus* FBB61, *Propionibacterium acidipropionici, Propionibacterium freudenreichii, Propionibacterium jensenii. Propionibacterium thoenii, Staphylococcus aureus, Staphylococcus epidermidis, Staphylococcus equorum, Staphylococcus gallinarum, Staphylococcus lugdunensis, Staphylococcus nepalensis, Streptococcus salivarius, Staphylococcus succinus, Staphylococcus xylosus, Streptococcus hyointestinalis* DPC6484, *Streptococcus uberis* strain 42, *Streptococcus thermophilus,* and *Weissella viridescens.*
14) The method of statement 1-12 or 13, wherein the probiotic composition comprises about $10^6$ to about $10^{13}$ CFU protagonist microorganisms, or about $10^7$ to about $10^{12}$ CFU protagonist microorganisms, or about $10^8$ W about $10^{12}$ CPU protagonist microorganisms, or about 109 to about $10^12$ CFU protagonist microorganisms, or about $10^6$ to about $10^{11}$ CFU protagonist microorganisms, or about $10^6$ to about $10^{10}$ CFU protagonist microorganisms, or about $10^6$ to about $10^9$ CFU protagonist microorganisms, or about $10^9$-$10^{11}$ CFU protagonist microorganisms.
15) The method of statement 1-13 or 14, further comprising assaying a fecal sample from a subject to identify classes or types of microorganisms in the fecal sample.
16) The method of statement 1-14 or 15, further comprising performing an assay comprising:
  assaying a fecal sample from a subject to identify classes or types of microorganisms in the fecal sample;
  identifying types of carbohydrate-metabolizing enzymes encoded in genomes of one or more of the classes or types of microorganisms in the fecal sample;

selecting one or more class(es) or type(s) of microorganism(s) to foster or inhibit in the gut of the subject;
making a prebiotic composition that fosters or inhibits the one or more class(es) or type(s) of selected microorganism(s).

17) The method of statement 15 or 16, wherein assaying a fecal sample comprises isolation of nucleic acids from the sample, sequencing sample nucleic acids, isolation of protein from the sample, incubation of one or more antibody with sample proteins, or a combination thereof.

18) The method of statement 15, 16 or 17, wherein assaying a fecal sample comprises polymerase chain reaction, primer extension, nucleic acid sequencing, or a combination thereof.

19) The method of statement 15-17 or 18, wherein assaying a fecal sample comprises determining ribosomal RNA sequences, determining ribosomal DNA sequences, determining carbohydrate-metabolizing enzyme sequences, or a combination thereof.

20) The method of statement 15-18 or 19, wherein assaying a fecal sample comprises sequencing sample ribosomal RNAs, sequencing carbohydrate-metabolizing enzyme gene sequences, or a combination thereof.

21) The method of statement 15-19 or 20 wherein assaying a fecal sample comprises sequencing sample 16S ribosomal RNAs and/or sequencing 23S ribosomal RNAs.

22) The method of statement 15-20 or 21, wherein identifying types of carbohydrate-metabolizing enzymes comprises identifying types of carbohydrate-metabolizing enzyme sequences in one or more of the classes or types of microorganisms in the fecal sample.

23) The method of statement 15-21 or 22, wherein identifying types of carbohydrate-metabolizing enzymes comprises sequencing one or more genomic carbohydrate-metabolizing enzyme sequence(s) of the one or more of the class(es) or type(s) of microorganisms in the fecal sample.

24) The method of statement 15-22 or 23, further comprising identifying one or more condition(s) or disease(s) in the subject.

25) The method of statement 15-23 or 24, wherein selecting one or more class(es) or type(s) of microorganism(s) to foster or inhibit in the gut of the subject comprises identifying whether any of the microorganism can synthesize one or more bacteriocins, short chain fatty acids (SCFAs). vitamins. anti-cancer agents, antibiotics, hydrogen peroxide, neuromodulators. neurotransmitters (e.g. gamma-aminobutyric acid (GABA)), co-factors, or combinations thereof.

26) The method of statement 15-24 or 25, wherein selecting one or more class(es) or type(s) of microorganism(s) to foster or inhibit in the gut of the subject comprises identifying which microorganism(s) can synthesize one or more bacteriocins, short chain fatty acids (SCFAs), vitamins, anti-cancer agents. antibiotics, hydrogen peroxide, neuromodulators, neurotransmitters (e.g. gamma-aminobutyric acid (GABA)), co-factors, or combinations thereof.

27) The method of statement 15-25 or 26, wherein selecting one or more class(es) or type(s) of microorganism(s) to foster or inhibit in the gut of the subject comprises performing an assay or test to determine whether one or more of the microorganism(s) can synthesize one or more bacteriocins, short chain fatty acids (SCFAs), vitamins, anti-cancer agents, antibiotics, hydrogen peroxide, neuromodulators, neurotransmitters (e.g. gamma-aminobutyric acid (GABA)), co-factors, or combinations thereof.

28) The method of statement 15-26 or 27, wherein selecting one or more class(es) or type(s) of microorganism(s) to foster or inhibit in the gut of the subject comprises culturing one or more of the microorganism(s) and testing whether the one or mom of cultured microorganism(s) can synthesize one or more bacteriocins, short chain fatty acids (SCFAs), vitamins, anti-cancer agents, anti-proliferatives, antibiotics, hydrogen peroxide, neuromodulators, neurotransmitters (e.g, gamma-aminobutyric acid (GABA)), co-factors, or a combination thereof in the culture media.

29) The method of statement 15-27 or 28, wherein selecting one or more class(es) or type(s) of microorganism(s) to foster or inhibit in the gut of the subject comprises identifying whether one or more of the microorganism genome(s) encode one or more bacteriocins, anti-cancer agents, anti-proliferatives, antibiotics, hydrogen peroxide, neuromodulators, neurotransmitters (e.g. gamma-aminobutyric acid (GABA)), co-factors, enzymes that make short chain fatty acids (SCFAs), enzymes that make one or more vitamins, or combinations thereof.

30) The method of statement 1-28 or 29, further comprising administering a prebiotic composition to the subject.

31) The method of statement 1-29 or 30, further comprising administering a prebiotic composition comprising one or more compounds of Formula I.

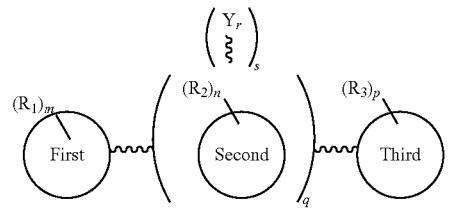

where:
each First, Second, and Third ring is separately a three-atom, four-atom, five-atom, or six-atom heterocyclic ring with one or two oxygen, sulfur, or nitrogen heteroatoms;
each Y is an optional monosaccharide or oligosaccharide with r monosaccharides, where each Y has a linkage ( ᔕᔕᔕ ) to a Second ring;
each ᔕᔕᔕ is separately a linkage between First, Second, and Third ring subunits, as well as linkages between each Y monosaccharide or Y oligosaccharide and a Second ring;
each m, n, and p is an integer separately selected from any of 2-5;
q is an integer selected from any of 1-100;
each r is an integer separately selected from 0-10;
s is an integer selected from 0-20; and
each $R_1$, $R_2$, and $R_3$ is separately selected from any of hydrogen, hydroxy, alkoxy, amino, carboxylate, aldehyde (CHO), phosphate or sulfate.

32) The method of statement 31, wherein one or more of the First. Second, or Third rings of Formula I is selected from a five-atom, or six-atom heterocyclic ring.

33) The method of statement 31 or 32, wherein one or more of the First, Second, or Third rings of Formula I has an oxygen or nitrogen heteroatom.
34) The method of statement 31, 32, or 33, wherein the Third ring of Formula I is a monosaccharide.
35) The method of statement 31-33 or 34, wherein the Third ring of Formula I is glucose.
36) The method of statement 31-34 or 35, wherein one or more linkages ( ∿∿∿ ) between the rings or the monosaccharides Formula I is an alpha or beta linkage.
37) The method of statement 31-35 or 36, wherein one or more linkages ( ∿∿∿ ) between the rings or the monosaccharides Formula I is a 1,2-linkage. 1,3-linkage, 1,4-linkage, 1,5-linkage, 1,6-linkage, 2,1-linkage, 2,2-linkage, 2,3-linkage, 2,4-linkage, 2,5-linkage, 2,6-linkage, 3,1-linkage, 3-2, linkage, 3,3-linkage, or a combination thereof.
38) The method of statement 31-36 or 37, wherein less than 20%, or less than 10%, of the total linkages between the First ring. Second rings, Third rings and Y groups can be cleaved by digestive enzymes in the saliva, stomach and small intestine.
39) The method of statement 31-37 or 38, wherein less than 20%, or less than 10%, of the total linkages between the First ring, Second rings, Third rings and Y groups are alpha-(1,4) linkages.
40) The method of statement 31-38 or 39, wherein at least 10%, or at least 20%, or at least 30%, or at least 40%, or at least 50%, or at least 55° 4, or at least 60%, or at least 65%, or at least 70%, or at least 75% of the total linkages between the First ring, Second rings, Third rings and Y groups are alpha(1,2) linkages or alpha-(1,6) linkages.
41) The method of statement 31-39 or 40, wherein each m, n, or p is an integer separately selected from any of 3-5.
42) The method of statement 31-40 or 41, wherein each m, n, or p is an integer separately selected from any of 4-5.
43) The method of statement 31-41 or 42, wherein q is an integer is selected from any of 1-20, or an integer is selected from any of 1-15, or an integer is selected from any of 1-10.
44) The method of statement 31-42 or 43, wherein q is larger than s.
45) The method of statement 31-43 or 44, wherein q is an integer of from 2 to 15, or an integer of from 2 to 10, or an integer of from 2 to 7.
46) The method of statement 31-44 or 45, wherein s is an integer of from 1 to 5. or of from 1 to 3, or of from 1 to 2.
47) The method of statement 31-45 or 46, wherein r defines the number of monosaccharides in the optional Y monosaccharide or oligosaccharide.
48) The method of statement 31-46 or 47, wherein r varies from about 0 to 10. or from about 0 to 7, or from about 0 to 5, or from about 0 to 3, or from about 0 to 1.
49) The method of statement 1-47 or 48, comprising administering a prebiotic composition comprising maltosyl-isomaltooligosaccharides with a mass average molecular weight distribution greater than about 640 daltons. wherein the prebiotic composition is administered with the probiotic composition or separately from the probiotic composition.
50) The method of statement 49, wherein the prebiotic composition comprises a mass average molecular weight distribution of about 730 to 20.000 daltons.
51) The method of statement 49 or 50, wherein the maltosyl-isomaltooligosaccharides contain more α-(1-6) glucosyl linkages than α-(1,2), α-(1,3), or α-(1,4) glucosyl linkages.
52) The method of statement 49, 50 or 51, wherein the prebiotic composition comprises composition comprising MIMO (DP 3-DP 9); mannitol; fructose; sucrose; maltose; one or more maltodextrins. lactate; glycerol; and acetate.
53) The method of statement 49-51 or 52, wherein the prebiotic composition comprises composition comprising composition 3 in the following table, where the values shown are given as %/brix, or % of refractive dry solids.

| Variable | Composition 3 |
|---|---|
| brix: | 18.7 |
| mannitol | 22.49 |
| fructose | 0.02 |
| sucrose | 1.03 |
| maltose | 2.99 |
| MIMO-DP 3 | 6.88 |
| MIMO-DP 4 | 14.07 |
| 1,4-DP3 | 6.29 |
| MIMO-DP 5 | 12.18 |
| MIMO-DP 6 | 5.90 |
| MIMO-DP 7 | 2.33 |
| MIMO-DP 8 | 1.04 |
| 1,4-DP4 | 5.02 |
| MIMO-DP 9 | 0.00 |
| lactate | 16.03 |
| glycerol | 0.35 |
| formate | 0.00 |
| acetate | 4.39 |
| TOTAL: | 101.52 |
| MIMO, %: | 42.40 |
| Purity, %: | 41.77 |
| MWD: | 745.47 |
| Yield %: | 45.76 | where 1,4-DP3, and 1,4-DP4 are maltodextrins.
54) The method of statement 49-53 or 54, wherein the prebiotic composition comprises composition comprising MIMO (DP 4-DP 9); mannitol; glucose; sucrose; maltose; panose; 1,4-DP 3 oligosaccharide(s); 1,4-DP 4 oligosaccharide(s); lactate; glycerol; formate; and acetate.
55) The method of statement 49-53 or 54, wherein the prebiotic composition comprises composition 4 or composition 5 in the following table, where the values shown are given as %/brix, or % of refractive dry solids.

| %/brix | Composition 4 | Composition 5 |
|---|---|---|
| Brix | 25.5 | 26.2 |
| mannitol | 18.28 | 17.35 |
| glucose | 0.44 | 0.93 |
| fructose | 0.00 | 0.00 |
| sucrose | 2.93 | 2.84 |
| maltose | 1.95 | 2.72 |
| panose | 4.65 | 4.43 |
| MIMO-DP4 | 11.33 | 9.96 |
| 1,4-DP3 | 10.66 | 10.23 |
| MIMO-DP5 | 10.29 | 9.05 |
| MIMO-DP6 | 7.08 | 6.82 |
| MIMO-DP7 | 2.94 | 3.12 |
| MIMO-DP8 | 1.85 | 1.69 |
| 1,4-DP4 | 9.93 | 6.33 |
| MIMO-DP9 | 0.00 | 0.00 |
| MIMO-DP10 | 0.00 | 0.00 |

-continued

| %/brix | Composition 4 | Composition 5 |
|---|---|---|
| lactic acid | 8.30 | 8.08 |
| glycerol | 0.24 | 0.23 |
| formic acid | 0.06 | 0.05 |
| acetic acid | 2.97 | 2.86 |
| MIMO | 38.15 | 35.07 |
| MO | 20.59 | 16.56 |
| Total | 93.86 | 86.70 |
| Purity | 40.64 | 40.45 |
| MWD | 795.82 | 790.16 |
| S/M | n/a | n/a |

56) The method of statement 49-54 or 55, wherein the prebiotic composition comprises the following:
57) The method of statement 1-55 or 56 further comprising treating one or more diseases or conditions in the subject.
58) The method of statement 1-56 or 57, wherein the prebiotic composition comprises IsoThrive™.
59) The method of statement 1-57 or 58, wherein the probiotic composition or the prebiotic composition comprises one or more fructo-oligosaccharides; beta-(2,6) oligofructan (levan); inulin; beta-(2,1) oligofructan; beta-1,2 terminated with glucose; beta-(1,3)-galactooligosaccharides; beta-(1-4)-galactooligosaccharides; beta-(1,6) galactooligosaccharides; beta-(1.4) xylooligosaccharides; hemicelluloses; arabinoxylan; guar gum: acacia gum; arabinogalactan, or combinations thereof.
60) The method of statement 1-58 or 59, wherein the probiotic composition or the prebiotic composition further comprises dietary plant polysaccharides that can be processed by one type of microorganism to foster growth or metabolism of a second type of microorganism.
61) The method of statement 1-59 or 60, wherein the probiotic composition or the prebiotic composition further comprises dietary plant polysaccharides that can be processed by *B. thetaioaomicron* to foster *E. rectale* synthesis of butyrate.
62) The method of statement 1-60 or 61, further comprising treating one or more diseases or conditions in the subject selected from a cancer, a pre-cancerous condition, a pre-cancerous propensity, diabetes, type 2 diabetes, an autoimmune disease, a vitamin deficiency, a mood disorder, degraded mucosal lining, ulcerative colitis, digestive irregularity, irritable bowel syndrome, acid reflux, constipation, or a combination thereof.
63) The method of statement 1-61 or 62, further comprising treating a cancer, a pre-cancerous condition, or a pre-cancerous propensity in the subject.
64) A method comprising administering to a subject a probiotic composition comprising *Lactobacillus gasseri*, *Lactococcus lactis*, or a combination thereof to a subject and administering to the subject a prebiotic composition comprising maltosyl-isomaltooligosaccharides with a mass average molecular weight distribution greater than about 640 daltons, wherein the prebiotic composition is administered with the probiotic composition or separately from the probiotic composition.
65) The method of statement 64, wherein the subject has cancer or may develop cancer.
66) The method of statement 64 or 65, wherein the subject has leukemia, oral squamous cell carcinoma, mouth cancer, head cancer, neck cancer, stomach cancer, colon cancer, bladder cancer, cervical cancer, or esophageal cancer.
67) The method of statement 64, 65, or 66, wherein the subject has metastatic cancer.
68) The method of statement 64-66 or 67, wherein the subject has an infection.
69) The method of statement 64-67 or 68, further comprising administering *Weissella viridescens* to the subject.
70) The method of statement 64-68 or 69, further comprising administering *Weissella viridescens* at the same time as the probiotic composition is administered.
71) The method of statement 64-69 or 70, wherein the probiotic composition further comprises *Weissella viridescens*.
72) The method of statement 64-70 or 71, further comprising administering *Weissella viridescens* at a time different from when the probiotic composition is administered.
73) The method of statement 64-71 or 72, which provides the subject with a therapeutically effective amount of nisin.
74) The method of statement 64-72 or 73, which provides the subject with an amount of nisin that is therapeutically effective to treat cancer.
75) The method of statement 64-73 or 74, which provides the subject with an amount of nisin that is therapeutically effective to treat an infection.
76) A method comprising incubating a protagonist microorganism with a challenger microbe to thereby manufacture greater amounts of a product than are generated when the protagonist is cultured under the same conditions but without the challenger microbe.
77) The method of statement 76, wherein the protagonist microorganism comprises *Lactococcus lactis*, *Lactobacillus* gasseri, or a combination thereof.
78) The method of statement 76 or 77, wherein the challenger microbe comprises *Weissella viridescens*.
79) The method of statement 76, 77, or 78, wherein the protagonist microorganism comprises at least one yeast species.
80) The method of statement 76-78 or 79, wherein the challenger microbe comprises at least one yeast species.
81) The method of statement 76-79 or 80, wherein the method manufactures at least 2-fold, or at least 3-fold, or at least 4-fold, or at least 5-fold, or at least 6-fold, or at least 7-fold, or at least 8-fold, or at least 9-fold, or at least 10-fold more product than is manufactured when the protagonist microorganism is cultured under the same conditions but without the challenger microbe.
82) The method of statement 76-80 or 81, wherein the method manufactures at least 2-fold, or at least 3-fold, or at least 4-fold, or at least 5-fold, or at least 6-fold, or at least 7-fold, or at least 8-fold, or at least 9-fold, or at least 10-fold more nisin than is manufactured when *Lactococcus lactis*, *Lactobacillus gasseri*, or a combination thereof is cultured under the same conditions but without *Weissella viridescens*.
83) The method of statement 76-81 or 82, wherein incubating a protagonist bacteria and/or challenger bacteria is within a culture medium selected from De-Man, Rogosa and Sharpe (MRS) media, LB liquid media, or M17 medium.

84) The method of statement 76-82 or 83, wherein incubating a protagonist bacteria and/or challenger bacteria is within a culture medium comprising peptone, lactose and yeast extract.

85) The method of statement 76-83 or 84, wherein incubating a protagonist bacteria and/or challenger bacteria is within a culture medium comprising peptone (meat, Sigma), bacteriological yeast extract (Marcor), maltosyl-isomaltooligosaccharides (MLMOs)], $MnSO_4$—$H_2O$ (J.T. Baker), $MgSO_4$ (Amresco), $FeSO_4$-$7H_2O$ (Amresco), $KH_2PO_4$ (Alfa Aesar), NaCl (BDH), and $CaCl_2$-$2H_2O$ (Alfa Aesar).

86) The method of statement 76-84 or 85, wherein incubating a protagonist yeast and/or challenger yeast is within a culture medium comprising a rich media, YPD media, or minimum media for yeast.

87) The method of statement 76-85 or 86, wherein incubating a protagonist yeast and/or challenger yeast is within a culture medium comprising about 1% yeast extract, 2% peptone and 2% dextrose.

88) The method of statement 76-86 or 87, wherein incubating a protagonist yeast and/or challenger yeast is within a culture medium comprising about 0.67% of yeast nitrogen base ("YNB") without amino acids supplemented with appropriate amino acids or purine or pyrimidine bases, about 2% sugars selected from glucose (dextrose), galactose, maltose, L-arabinose, or combinations thereof.

89) A method of manufacturing one or more beneficial compound or material product comprising adding a challenger microbe to a culture of manufacturing (e.g., protagonist) microorganisms, and incubating the manufacturing microorganism and challenger microbe together in a culture medium for a time and under conditions sufficient to manufacture the beneficial compound or material product.

90) The method of statement 89, wherein the challenger microbe stimulates the manufacturing microorganisms to manufacture more of at least one product than when the challenger microbe is present than when the challenger microbe is not present.

91) The method of statement 89 or 90, wherein the challenger microbe does not manufacture the product.

92) The method of statement 89, 90, or 91, wherein the manufacturing microorganism is a bacterial species, or a fungal species.

93) The method of statement 89-91 or 92, wherein incubating is performed in a fermentation apparatus.

94) The method of statement 89-92 or 93, wherein the manufacturing microorganism and the challenger microbe is at an initial ratio of:
about 10 manufacturing microorganisms: 1 challenger microbe; or
about 50 manufacturing microorganisms: 1 challenger microbe; or
about 100 manufacturing microorganisms: 1 challenger microbe; or
about 1000 manufacturing microorganisms: 1 challenger microbe; or
about 10 manufacturing microorganisms: 2 challenger microbes; or
about 10 manufacturing microorganisms: 3 challenger microbes; or
about 10 manufacturing microorganisms: 4 challenger microbes; or
about 10 manufacturing microorganisms: 5 challenger microbes; or
about 10 manufacturing microorganisms: 6 challenger microbes; or
about 10 manufacturing microorganisms: 7 challenger microbes; or
about 10 manufacturing microorganisms: 8 challenger microbes; or
about 10 manufacturing microorganisms: 9 challenger microbes; or
about 1 manufacturing microorganism: 1 challenger microbes; or
about 1 manufacturing microorganism: 2 challenger microbes.

95) The method of statement 89-93 or 94, wherein an inoculum of late-log challenger microbes is added to the culture of manufacturing microorganisms at about 1-2% of the protagonist broth, or about 1.3% of the protagonist broth volume.

96) The method of statement 89-94 or 95, wherein the challenger microbe(s) are added to a late log-phase protagonist culture.

97) The method of statement 89-95 or 96, wherein the manufacturing microorganisms with or without the challenger microbes is incubated for at least 6 hours, or at least 8 hours, or at least 10 hours, or at least 12 hours, or at least 14 hours, or at least 16 hours, or at least 20 hours, or at least 24 hours, or at least 48 hours.

98) The method of statement 89-96 or 97, wherein incubating is continuous, with fresh nutrients added periodically and product removed at various intervals.

99) The method of statement 89-97 or 98, wherein the culture medium is cycled over immobilized manufacturing microorganisms.

100) The method of statement 89-98 or 99, wherein the manufacturing microorganisms comprise *Lactococcus lactis*.

101) The method of statement 89-99 or 100, wherein the challenger microbes comprise *Weissella viridescens*.

102) The method of statement 89-100 or 101, wherein the conditions comprise a temperature of about 20° C. to about 42° C., or of about 35° C. to about 37° C.

103) The method of statement 89-101 or 102, wherein the conditions comprise prebiotics in the culture medium.

104) The method of statement 89-102 or 103, wherein the culture medium comprises a carbon source selected from one or more types of maltosyl-isomaltooligosaccharides (MIMOs), fructo-oligosaccharides; beta-(2,6) oligofructan (levan); inulin; beta-(2,1) oligofructan; beta-1,2 terminated with glucose; beta-(1,3)-galactooligosaccharides; beta-(1-4)-galactooligosaccharides; beta-(1,6) galactooligosaccharides: beta-(1,4) xylooligosaccharides; hemicelluloses; arabinoxylan; guar gum; acacia gum; arabinogalactan, or combinations thereof.

105) The method of statement 89-103 or 104, wherein the culture medium comprises maltosyl-isomaltooligosaccharides (MIMOs).

106) The method of statement 89-104 or 105, wherein the manufacturing microorganism is incubated for 6 hours. 8 hours, 10 hours, 12 hours, 14 hours, 16 hours, 18 hours, 20 hours, 22 hours, or 24 hours in a culture medium with a defined carbon source before addition of the challenger microbe.

107) The method of statement 89-105 or 106, wherein the manufacturing microorganism is incubated for 6 hours, 8 hours, 10 hours, 12 hours, 14 hours, 16 hours, 18 hours. 20 hours. 22 hours, or 24 hours in a culture medium with a defined limiting carbon source before addition of the challenger microbe.
108) The method of statement 89-106 or 107, wherein the manufacturing microorganisms deplete the media by 6 hours, 8 hours. 10 hours, 12 hours, 14 hours, 16 hours. 18 hours, 20 hours, 22 hours, or 24 hours of incubation.
109) The method of statement 89-107 or 108, wherein the culture medium is replenished with additional carbon source after depletion of a first carbon source.
110) The method of statement 109, wherein the additional carbon source is selected from one or more type of maltosyl-isomaltooligosaccharides (MIMOs), fructo-oligosaccharides; beta-(2,6) oligofructan (levan); inulin; beta-(2,1) oligofructan; beta-1,2 terminated with glucose; beta-(1,3)-galactooligosaccharides; beta-(1-4)-galactooligosaccharides; beta-(1,6) galactooligosaccharides; beta-(1,4) xylooligosaccharides; hemicelluloses; arabinoxylan; guar gum; acacia gum; arabinogalactan, or combinations thereof.
111) The method of statement 109 or 110, wherein the additional carbon source is selected from one or more type of maltosyl-isomaltooligosaccharides (MIMOs).
112) The method of statement 109, 110, or 111, wherein the additional carbon source stimulates growth of the manufacturing microorganisms for another 0.5-6 hours, for another 1.5 hours, or for another 2-4 hours.
113) The method of statement 109-111 or 112, wherein the challenger microbes are added at about 0.5-6 hours, for another 1-5 hours, or for another 2-4 hours after the culture medium is replenished with additional carbon source.
114) The method of statement 109-112 or 113, wherein the manufacturing microorganism is incubated with the challenger microbes for about 12 hours, or about 16 hours, or about 18 hours, or about 20 hours, or about 24 hours, or about 27 hours, or about 30 hours, or about 36 hours, or about 48 hours.
115) The method of statement 109-113 or 114, wherein at least 2-fold, or at least 3-fold, or at least 5-fold, or at least 7-fold, or at least 10-fold more of the beneficial compound(s) or material(s) are manufactured than when the challenger microbe is not present.
116) The method of statement 109-114 or 115, wherein at least 5-fold more of the beneficial compound(s) or material(s) are manufactured than when the challenger microbe is not present.
117) The method of statement 109-115 or 116, wherein the manufacturing microorganisms are immobilized to a solid surface.
118) The method of statement 109-116 or 117, wherein the manufacturing microorganisms are immobilized to a solid surface selected from beads, a column matrix, a culture plate, a culture flask, a solid surface within a fermentation apparatus, or a combination thereof.
119) The method of statement 109-117 or 118, wherein the manufacturing microorganisms are immobilized to a column matrix or a solid surface in a fermentation apparatus.
120) The method of statement 117, 118, or 119, wherein the culture medium is circulated across or through the solid surface.
121) The method of statement 117-119, or 120, wherein at least one component of the culture medium is replenished periodically.
122) The method of statement 117-120, or 121, wherein the challenger microbes are added to the culture medium and circulated with the culture medium.
123) The method of statement 117-121, or 122, wherein culture medium from incubation of the challenger microbes is added to the culture medium and circulated with the culture medium.
124) The method of statement 109-122 or 123, wherein one or more types of the challenger microbes are immobilized to a solid surface.
125) The method of statement 109-123 or 124, wherein the challenger microbes are immobilized to a solid surface selected from beads, a column matrix, a culture plate, a culture flask, a solid surface within a fermentation apparatus, or a combination thereof.
126) The method of statement 109-124 or 125, wherein the manufacturing microorganisms are immobilized to a different solid surface than the challenger microbes.
127) The method of statement 109-125 or 126, wherein the beneficial compound or material product is removed from circulating media either continuously or periodically.
128) The method of statement 89-126 or 127, wherein manufacture of one or more of the beneficial compound or material products is automated.
129) The method of statement 89-127 or 128. further comprising isolation or purification of one or more of the beneficial compound or material products.
130) The method of statement 89-128 or 129, further comprising isolation or purification of one or more of the beneficial compound or material products by separation methods based on one or more chemical property, physical property, or molecular size difference in beneficial compound or material products and/or impurities.
131) The method of statement 89-129 or 130. further comprising isolation or purification of one or more of the beneficial compound or material products by separation methods selected from ammonium sulfate precipitation, dialysis, filtration, size exclusion chromatography, ion exchange chromatography, high pressure liquid chromatography (HPLC), hydrophilic interaction liquid chromatography (HILIC), or combinations thereof.
132) The method of statement 89-130 or 131, further comprising characterization of one or more of the beneficial compound or material products by use of MALDI-MS, LC-MS/MS, NMR, and/or fluorescent monoclonal antibodies.
133) The method of statement 89-131 or 132, further comprising assaying an antibacterial, anti-proliferative, and/or anti-cancer activity of one or more of the beneficial compound or material products.

The specific compositions and methods described herein are representative, exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features. modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a compound" or "a catalyst" or "a ligand" includes a plurality of such compounds, catalysts or ligands, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

---

What is claimed:

1. A method of manufacturing one or more bacteriocin product comprising adding at least one type of antagonist to a liquid culture of manufacturing microorganisms selected from at least one lactic acid bacteria or a combination thereof, and incubating the manufacturing microorganisms and the at least one type of challenger microbe together in a liquid culture medium suitable for growth of all bacterial types involved to manufacture the bacteriocin product, wherein the amount of the bacteriocin product produced by the manufacturing organisms in the presence of the antagonist is at least 5-fold greater than the amount of the bacteriocin product produced by the manufacturing organisms in the absence of the antagonist.

2. The method of claim 1, wherein at least one type of antagonist stimulates the manufacturing microorganisms to manufacture more of at least one bacteriocin than when the challenger microbes are not present.

3. The method of claim 1, wherein the at least one type of antagonist is *Weissella viridescens* NRRL B-1951.

4. The method of claim 1, further comprising generating a cell-free broth comprising at least one bacteriocin.

5. A composition comprising at least one type of bacteriocin product made by the method of claim 1.

6. The composition of claim 5, formulated for local administration to a portion of the gastrointestinal system.

7. The method of claim 1, wherein the at least one type of challenger microbe is in log phase when added to the liquid culture of manufacturing.

8. The method of claim 1, wherein the at least one type of challenger microbe is added to the liquid culture of manufacturing microorganisms in log phase.

9. The method of claim 7, wherein the at least one type of challenger microbe is added to the liquid culture of manufacturing microorganisms in log phase.

10. The method of claim 1, wherein the liquid culture of manufacturing microorganisms is replenished with a carbon source before adding the at least one type of antagonist.

11. The method of claim 10, wherein the liquid culture of manufacturing microorganisms reaches log phase before adding the at least one type of antagonist.

* * * * *